United States Patent

Toriyabe et al.

Patent Number: 5,728,699
Date of Patent: Mar. 17, 1998

[54] BENZYLSULFIDE DERIVATIVE, PROCESS FOR ITS PRODUCTION AND PESTICIDE

[75] Inventors: Keiji Toriyabe; Hideharu Sasaki; Naoshi Masuyama; Akihide Nagai; Hiroyuki Yano; Mieko Kawashima, all of Shizuoka; Yutaka Kurihara, Nagoya; Tomonori Shimazu, Hamamatsu, all of Japan

[73] Assignees: Kumiai Chemical Industry Co., Ltd.; Ihara Chemical Industry Co., Ltd., both of Tokyo, Japan

[21] Appl. No.: 750,774

[22] PCT Filed: Apr. 18, 1996

[86] PCT No.: PCT/JP96/01055

§ 371 Date: Dec. 19, 1996

§ 102(e) Date: Dec. 19, 1996

[87] PCT Pub. No.: WO96/33168

PCT Pub. Date: Oct. 24, 1996

[30] Foreign Application Priority Data

Apr. 19, 1995 [JP] Japan ................... 7-117838

[51] Int. Cl.$^6$ ............ A01N 43/58; A01N 43/40; C07D 237/02; C07C 335/00

[52] U.S. Cl. ............ 514/247; 514/354; 514/357; 514/639; 514/247; 544/239; 544/240; 544/224; 544/241; 546/343; 564/31; 564/32; 564/38; 564/42

[58] Field of Search ............ 544/239, 240, 544/241, 224; 546/343; 564/251, 313; 568/31, 32, 38, 42; 514/247, 354, 357, 639

[56] References Cited

U.S. PATENT DOCUMENTS 3,732,307  5/1973  Middleton et al. ............ 260/566

OTHER PUBLICATIONS

Kornblum et al., Journal of the American Chemical Society, vol. 101, No. 3, pp. 647–657, 1979.

*Primary Examiner*—Deborah Lambkin
*Attorney, Agent, or Firm*—Oblon, Spivak, McClelland, Maier & Neustadt, P.C.

[57] ABSTRACT

The present invention presents a benzylsulfide derivative of the formula (I) or its salt:

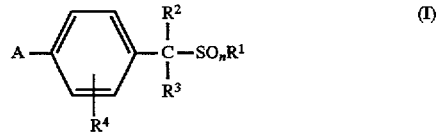

wherein $R^1$ is a $C_{1-6}$ alkyl group, a $C_{1-6}$ haloalkyl group, a $C_{2-4}$ alkenyl group, a cyano group, etc., and each of $R^2$ and $R^3$ is a hydrogen atom, a halogen atom, a cyano group, a $C_{1-4}$ alkyl group, a $C_{1-3}$ haloalkyl group, etc., $R^4$ is a hydrogen atom, a halogen atom, a $C_{1-4}$ alkyl group, etc., A is a hydrazinoaralkyl group or hydrazonoaralkyl group, and n is 0, 1 or 2; a process for its production; and a pesticide containing such a benzylsulfide derivative as an active ingredient. The benzylsulfide derivative of the present invention is capable of controlling various pests without adversely affecting crop plants.

7 Claims, No Drawings

BENZYLSULFIDE DERIVATIVE, PROCESS FOR ITS PRODUCTION AND PESTICIDE

TECHNICAL FIELD

The present invention relates to a novel benzylsulfide derivative, a process for its production and a pesticide containing it as an active ingredient.

BACKGROUND ART

Heretofore, it has been reported, for example, in U.S. Pat. No. 3,732,307 and Japanese Unexamined Patent Publications No. 122261/1979 and No. 45452/1981 that benzohydrazonophenylsulfide derivatives are useful as insecticides. However, the benzylsulfide derivative of the present invention has not been known.

In recent years, some of conventional commercial insecticides have been restricted in their use in view of problems such as the residual effects, accumulation or environmental pollution, and some have become not so effective as the pests have acquired resistance during their use for a long period of time. Therefore, it has been desired to develop a new insecticide which is highly effective at a low dose and which is excellent in safety.

The present inventors have synthesized various benzylsulfide derivatives and have studied their physiological activities. As a result, it has been found that the compound of the present invention exhibits outstanding pesticidal activities against various pests, particularly against agricultural and horticultural pests including lepidopteran injurious insects represented by diamond back (*Plutella xylostella*), Asiatic rice borer (*Chio suppressalis*) and beat armyworm (*Spodoptera exigua*), hemipteran injurious insects represented by brown planthopper (*Nilaparvata lugens*), green rice leafhopper (*Nephotetlix cincticeps*) and cotton aphid (*Aphis gossypii*) and elytron injurious insects represented by adzuki bean weevil (*Callosobrunchus chinensis*). The present invention has been accomplished on the basis of this discovery.

DISCLOSURE OF INVENTION

That is, the present invention provides (1) a benzylsulfide derivative of the formula (I) or its salt:

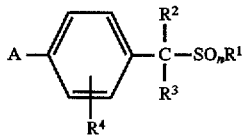

wherein $R^1$ is a $C_{1-6}$ alkyl group, a $C_{1-4}$ cyanoalkyl group, a $C_{1-4}$ hydroxyalkyl group, a $C_{3-6}$ cycloalkyl group, a $C_{1-6}$ haloalkyl group, a $C_{2-4}$ alkenyl group, a $C_{2-4}$ alkynyl group, a phenyl group (which may be substituted by a halogen atom or a $C_{1-4}$ alkyl group), a cyano group, a benzyl group (which may be substituted by a halogen atom), a thiazolyl group, a $C_{1-4}$ alkylcarbamoyl group or a group of the formula $-N(R^5)R^6$; each of $R^2$ and $R^3$ which are independent of each other, is a hydrogen atom, a halogen atom, a cyano group, a $C_{1-4}$ alkyl group, a $C_{1-3}$ haloalkyl group, a $C_{1-4}$ alkylthio group, a $C_{1-4}$ alkylcarbonyl group, a carboxyl group, or a $C_{1-4}$ alkoxycarbonyl group; or $R^2$ and $R^3$ may form a 3- to 6-membered ring together with the carbon atom to which they are bonded; or $R^1$ and $R^2$ may form a 3- to 8-membered ring having one or more hetero atoms, together with the sulfur and carbon atoms to which they are respectively bonded; $R^4$ is a hydrogen atom, a halogen atom, a $C_{1-4}$ alkyl group, a $C_{1-4}$ haloalkyl group, a $C_{1-4}$ alkoxy group or a $C_{1-4}$ haloalkoxy group; each of $R^5$ and $R^6$ which are independent of each other, is a hydrogen atom, a $C_{1-6}$ alkyl group or a $C_{1-4}$ haloalkyl group; or $R^5$ and $R^6$ may together form a group of the formula $=CR^7R^8$; or $R^5$ and $R^6$ may form a 4- to 8-membered ring having one or more hetero atoms, together with the nitrogen atom to which they are bonded; $R^7$ is a hydrogen atom, a $C_{1-3}$ alkyl group or a $C_{1-3}$ alkylthio group; $R^8$ is a $C_{1-3}$ alkylthio group or a $C_{1-3}$ alkylamino group; or $R^7$ and $R^8$ may form a saturated or unsaturated 4- to 8-membered ring together with the carbon atom to which they are bonded; A is a hydrazinoaralkyl or hydrazonoaralkyl group of the formula (A1) or (A2):

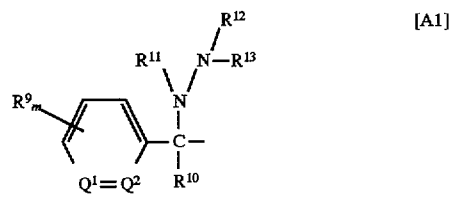

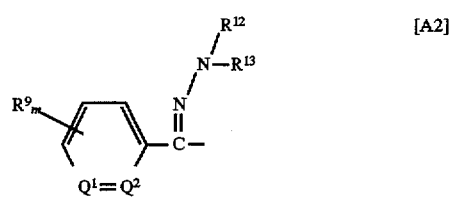

$R^9$ is a hydrogen atom, a halogen atom, a nitro group, a cyano group, a $C_{1-4}$ alkyl group, a $C_{1-4}$ haloalkyl group, a $C_{1-4}$ alkoxy group, a $C_{1-4}$ haloalkoxy group, a $C_{1-4}$ alkylthio group, a $C_{1-4}$ haloalkylthio group, a $C_{1-4}$ alkylsulfonyl group, a $C_{2-4}$ alkylsulfonylmethyl group, a $C_{1-4}$ haloalkylsulfonyloxy group, a phenyl group (which may be substituted by a halogen atom) or a phenoxy group (which may be substituted by a halogen atom); or two $R^9$ may together form a 5- or 6-membered ring; $R^{10}$ is a hydrogen atom or a $C_{1-4}$ alkyl group; each of $R^{11}$, $R^{12}$ and $R^{13}$ which are independent of one another, is a hydrogen atom, a cyano group, a $C_{1-6}$ alkyl group, a $C_{1-4}$ haloalkyl group, a $C_{2-10}$ alkoxyalkyl group, a $C_{3-8}$ alkoxyalkoxyalkyl group, a $C_{2-6}$ alkylthioalkyl group, a $C_{2-6}$ alkenyl group, a $C_{2-4}$ alkynyl group, a $C_{1-4}$ cyanoalkyl group, a benzyl group (which may be substituted by a halogen atom, a $C_{1-4}$ haloalkyl group or a $C_{1-4}$ alkyl group), a group of the formula $-COR^{14}$, a group of the formula $-CSR^{14}$, a group of the formula $-COOR^{15}$, a group of the formula $-COSR^{15}$, a group of the formula $-CON(R^{16})R^{17}$, a group of the formula $-CSN(R^{16})R^{17}$ a group of the formula $-SN(R^{18})R^{19}$, a group of the formula $-SO_2R^{20}$ or a group of the formula $-C(R^{21})=CHR^{22}$; or $R^{12}$ and $R^{13}$ may together form a group of the formula $=CR^{23}R^{24}$; or $R^{12}$ and $R^{13}$ may form a 4- to 8-membered ring having one or more hetero atoms, together with the nitrogen atom to which they are bonded; $R^{14}$ is a hydrogen atom, a $C_{1-20}$ alkyl group, a $C_{1-8}$ haloalkyl group, a $C_{2-12}$ alkoxyalkyl group, a $C_{2-10}$ haloalkoxyalkyl group, a $C_{3-16}$ alkoxyalkoxyalkyl group, a $C_{4-22}$ alkoxyalkoxyalkoxyalkyl group, a $C_{2-6}$ alkylthioalkyl group, a $C_{3-5}$ cycloalkyl group, a $C_{1-6}$ hydroxyalkyl group, a $C_{1-6}$ aminoalkyl group, a $C_{1-6}$ amidoalkyl group, a $C_{1-8}$ cyanoalkyl group, a $C_{3-12}$ alkoxycarbonylalkyl group, a $C_{2-6}$ alkenyl group, a $C_{2-4}$ alkynyl group, a phenyl group (which may be substituted by a halogen atom, a nitro group, a $C_{1-4}$ alkyl group, a $C_{1-4}$ haloalkyl group, a phenoxy group or a $C_{1-4}$ alkoxy group), a naphthyl group (which may be substituted by a halogen atom or a $C_{1-4}$ alkyl group) or a hetero aromatic ring group (which may be substituted by a halogen atom or a $C_{1-4}$ alkyl group); $R^{15}$ is a $C_{1-20}$ alkyl group, a $C_{2-8}$ haloalkyl group, a $C_{2-12}$ alkoxyalkyl group, a $C_{2-6}$ alkenyl group, $C_{2-4}$ alkynyl group, a benzyl group (which may be substituted by a halogen atom, a $C_{1-4}$ alkoxy group or a $C_{1-4}$ alkyl group) or a phenyl group (which may be substituted by a halogen atom); $R^{16}$ is a hydrogen atom or a $C_{1-4}$ alkyl group; $R^{17}$ is a hydrogen atom, a $C_{1-6}$ alkyl group or a phenyl group (which may be substituted by a halogen atom, a $C_{1-4}$ haloalkoxy group or a $C_{1-4}$ alkyl group); each of $R^{18}$ and $R^{19}$ which are independent of each other, is a $C_{1-4}$ alkyl group (which may be substituted by a $C_{1-4}$ alkoxycarbonyl group), or a $C_{2-5}$ alkoxyalkyl group; or $R^{18}$ and $R^{19}$ may form a 5- or 6-membered ring together with the nitrogen atom to which they are bonded; $R^{20}$ is a $C_{1-4}$ alkyl group, a $C_{1-4}$ haloalkyl group or a $C_{2-4}$ dialkylamino group; $R^{21}$ is a hydrogen atom or a $C_{1-6}$ alkyl group; $R^{22}$ is a $C_{2-4}$ acyl group or a $C_{2-6}$ alkoxycarbonyl group; each of $R^{23}$ and $R^{24}$ which are independent of each other, is a hydrogen atom, a halogen atom, a $C_{1-6}$ alkyl group or a group of the formula $-N(R_{25})R_{26}$; each of $R^{25}$ and $R^{26}$ which are independent of each other, is a hydrogen atom, a $C_{1-4}$ alkyl group, a $C_{1-4}$ alkoxy group, a $C_{2-12}$ alkoxyalkyl group or a group of the formula $-SO_2R^{27}$; or $R^{25}$ and $R^{26}$ may form a 5- or 6-membered ring together with the nitrogen atom to which they are bonded; $R^{27}$ is a $C_{1-8}$ alkyl group or a phenyl group (which may be substituted by a halogen atom or a $C_{1-4}$ alkyl group); each of $Q^1$ and $Q^2$ is a nitrogen atom or a group of the formula $-CR^9$; m is an integer of from 1 to 3; and n is 0, 1 or 2;

(2) a benzylsulfide derivative of the formula (II):

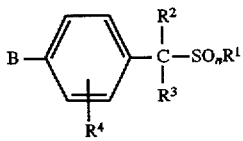

wherein $R^1$, $R^2$, $R^3$, $R^4$ and n are as defined in Claim 1; and B is an aralkyl or arylcarbonyl group of the formula (B1) or (B2):

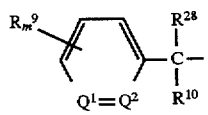

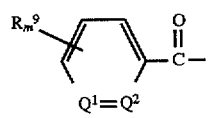

wherein $R^9$, $R^{10}$, $Q^1$ and $Q^2$ are as defined in Claim 1, and $R^{28}$ is a halogen atom or a hydroxyl group;

(3) a benzophenonehydrazone derivative of the formula (III):

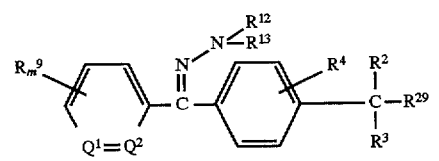

wherein $R^4$, $R^9$, $R^{12}$, $R^{13}$, m, $Q^1$ and $Q^2$ are as defined in Claim 1; each of $R^2$ and $R^3$ which are independent of each other, is a hydrogen atom or a $C_{1-4}$ alkyl group, and $R^{29}$ is a halogen atom, a mercapto group or a hydroxyl group;

(4) a process for producing a benzylsulfide derivative wherein A is a group of the formula (A2) as defined in Claim 1, which comprises reacting a compound of the formula (IV):

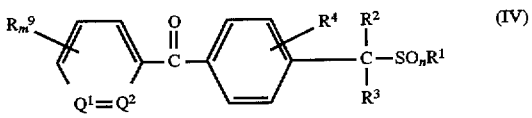

wherein $R^1$, $R^2$, $R^3$, $R^4$, $R^9$, m, n, and are as defined $Q^1$, and $Q^2$ are as defined in Claim 1, with a compound of the formula (V1):

wherein $R^{12}$ and $R^{13}$ are as defined in Claim 1;

(5) a process for producing a benzylsulfide derivative wherein A is a group, of the formula (A2) as defined in Claim 1, which comprises reacting a compound of the formula (III);

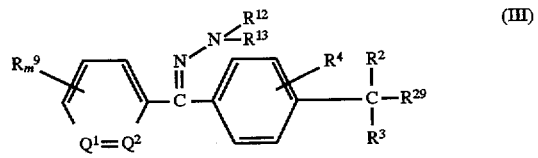

wherein $R^2$, $R^3$, $R^4$, $R^9$, $R^{12}$, $R^{13}$, $R^{29}$, m, $Q^1$ and $Q^2$ are as defined in Claim 3, with a compound of the formula (V2):

wherein Z is a halogen atom, a $C_{1-4}$ alkylsulfonyl group or a benzenesulfonyloxy group (which may be substituted by a methyl group) when $R^{29}$ is a mercapto group, or a group of the formula $-S(O)_nM$ when $R^{29}$ is a halogen atom, or a group of the formula $-SSR^1$ when $R^{29}$ is a hydroxyl group; $R^1$ is a $C_{1-6}$ alkyl group, a $C_{1-4}$ cyanoalkyl group, a $C_{3-6}$ cycloalkyl group, a $C_{1-6}$ haloalkyl group, a $C_{2-4}$ alkenyl group or a benzyl group (which may be substituted by a halogen atom); M is an alkali metal; and n is 0 or 2;

(6) a process for producing a benzylsulfide derivative wherein A is a group of the formula (A1) as defined in Claim 1, which comprises reacting a compound of the formula (VI):

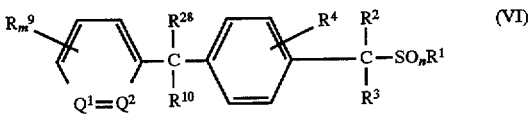

wherein $R^1$, $R^2$, $R^3$, $R^4$, $R^9$, $R^{10}$, m, n, $Q^1$ and $Q^2$ are as defined in Claim 1, and $R^{28}$ is a halogen atom, with a compound of the formula (V1):

wherein $R^{12}$ and $R^{13}$ are as defined in Claim 1; and (7) a pesticide containing a benzylsulfide derivative as defined in Claim 1, as an active ingredient.

In the present invention, the halogen atom represents a fluorine atom, a chlorine atom, a bromine atom or an iodine atom.

The alkyl group means a linear or branched $C_{1-20}$ alkyl group such as a methyl group, an ethyl group, a n-propyl group, an isopropyl group, a n-butyl group, an isobutyl group, a sec-butyl group, a tert-butyl group, a n-pentyl group, an isoamyl group, a neopentyl group, a n-hexyl group, an isohexyl group, a 3,3-dimethylbutyl group, a n-heptyl group, a n-octyl group, a n-nonyl group or a n-decyl group.

The cycloalkyl group represents a $C_{3-6}$ cycloalkyl group such as a cyclopropyl group, a cyclopentyl group or a cyclohexyl group.

The alkenyl group represents a linear or branched $C_{1-6}$ alkenyl group such as an ethenyl group or a 2-propenyl group.

The haloalkyl group represents a linear or branched $C_{1-8}$ alkyl group which is substituted from 1 to 10 halogen atoms which may be the same or different such as a chloromethyl group, a trifluoromethyl group or a tetrafluoroethyl group.

The cyanoalkyl group represents a linear or branched $C_{1-8}$ alkyl group which is substituted by a cyano group.

The hydroxyalkyl group represents a linear or branched $C_{1-8}$ alkyl group which is substituted by a hydroxyl group.

The alkoxy group represents an alkyl-O- group wherein the alkyl moiety is as defined above, and it may, for example, be a methoxy group or an ethoxy group.

The haloalkoxy group represents a haloalkyl-O- group wherein the haloalkyl moiety is as defined above, and it may, for example, be a trifluoromethoxy group or a 2-chloroethoxy group.

The alkylthio group represents an alkyl-S- group wherein the alkyl moiety is as defined above, and it may, for example, be a methylthio group or an ethylthio group.

The haloalkylthio group represents a haloalkyl-S- group wherein the haloalkyl moiety is as defined above, and it may, for example, be a trifluoromethylthio group or a 2-chloroethylthio group.

The alkylsulfonyl group represents an alkyl-SO$_2$- group wherein the alkyl moiety is as defined above, and it may, for example, be a methylsulfonyl group or an ethylsulfonyl group.

The alkylsulfonylmethyl group represents an alkyl-SO$_2$CH$_2$- group wherein the alkyl moiety is as defined above, and it may, for example, be a methylsulfonylmethyl group or an ethylsulfonylmethyl group.

The alkylene group means a linear $C_{1-8}$ alkylene group such as a methylene group, an ethylene group, a trimethylene group or a tetramethylene group.

The alkoxyalkyl group represents an alkyl-O-alkylene group wherein the alkyl moiety and the alkylene moiety are as defined above, and it may, for example, be a methoxymethyl group or an ethoxymethyl group.

The alkylthioalkyl group represents an alkyl-S-alkylene group wherein the alkyl moiety and the alkylene moiety are as defined above, and it may, for example, be a methylthiomethyl group or an ethythiomethyl group.

The alkoxyalkoxyalkyl group represents an alkyl-O-alkylene-O-alkylene group wherein the alkyl moiety and each alkylene moiety are as defined above.

The alkoxyalkoxyalkoxyalkyl group represents an alkyl-O-alkylene-O-alkylene-O-alkylene group, wherein the alkyl and each alkylene group are as defined above.

The aminoalkyl group represents a linear or branched $C_{1-8}$ alkyl group which is substituted by an amino group, a monoalkylamino group or a dialkylamino group.

The amidealkyl group represents a linear or branched $C_{1-8}$ alkyl group which is substituted by an acylamino group or an N-alkyl-N-acylamino group.

The alkynyl group represents a linear $C_{1-4}$ alkynyl group.

The hetero aromatic ring group represents a 5-membered aromatic ring group containing from 1 to 4 nitrogen, oxygen or sulfur atoms or a fused ring thereof with a benzene ring, or a 6-membered aromatic ring group containing from 1 to 3 nitrogen atoms or a fused ring thereof with a benzene ring, and it may, for example, be a furyl group, a thienyl group, a pyrazolyl group, an imidazolyl group, a benzofuranyl group, a benzothiazolyl group, a pyridyl group, a pyrimidinyl group, a pyridazinyl group, a triazinyl group, a quinolyl group or a quinoxalinyl group.

In the compound of the present invention, the salt is a salt of the compound of the formula (I) with an acid, or a salt of the compound of the formula (I) wherein $R^2$ or $R^3$ is a carboxyl group, with a metal or an amine. The acid may, for example, be a hydrogen halide acid such as hydrochloric acid or hydrobromic acid, or a sulfonic acid such as methane sulfonic acid. The metal may, for example, be an alkali metal such as sodium or potassium, or an alkaline earth metal such as magnesium or calcium. The amine may, for example, be ammonia, isopropylamine or triethylamine.

A preferred group of compounds of the above formula (I) is a group of compounds wherein:

$R^1$ is a $C_{1-4}$ alkyl group, a $C_{1-2}$ cyanoalkyl group, a hydroxyethyl group, a cyclopentyl group, a $C_{1-2}$ haloalkyl group, a phenyl group (which may be substituted by a halogen atom), a cyano group, a $C_{1-4}$ alkylcarbamoyl group or a thiazolyl group;

each of $R^2$ and $R^3$ which are independent of each other, is a hydrogen atom, a methyl group or a $C_{1-2}$ alkoxycarbonyl group; or $R^1$ and $R^2$ may form a 5-membered ring together with the sulfur and carbon atoms to which they are respectively bonded;

$R^4$ is a hydrogen atom or a fluorine atom;

A is a hydrazinoaralkyl or hydrazonoaralkyl group of the formula (A1) or (A2);

$R^9$ is a hydrogen atom, a halogen atom, a nitro group, a cyano group, a methyl group, a trifluoromethyl group, a methoxy group, a $C_{1-2}$ haloalkoxy group, a methylthio group, a difluoromethylthio group, a methylsulfonyl group, a methylsulfonylmethyl group, a trifluoromethylsulfonyloxy group, a phenyl group, a phenoxy group which may be substituted by a halogen atom, or a methylene dioxy group;

$R^{10}$ is a hydrogen atom;

$R^{11}$ is a hydrogen atom, a group of the formula —COR$^{14}$ or a group of the formula —COOR$^{15}$;

each of $R^{12}$ and $R^{13}$ which are independent of each other, is a hydrogen atom, a $C_{1-4}$ alkyl group, a $C_{1-4}$ haloalkyl group, a $C_{2-10}$ alkoxyalkyl group, a $C_{3-8}$ alkoxyalkoxyalkyl group, a $C_{2-6}$ alkylthioalkyl group, a cyanomethyl group, a benzyl group (which may be substituted by a halogen atom or a trifluoromethyl group), a group of the formula —COR$^{14}$, a group of the formula —COOR$^{15}$, a group of the formula —CONHR$^{17}$, a group of the formula —SO$_2$R$^{20}$ or a group of the formula —C(R$^{21}$)=CHR$^{22}$; or $R^{12}$ and $R^{13}$ may together form a group of the formula =CR$^{23}$R$^{24}$; or $R^{12}$ and $R^{13}$ may form a 5-membered ring together with the nitrogen atom to which they are bonded;

$R^{14}$ is a $C_{1-10}$ alkyl group, a $C_{1-4}$ haloalkyl group, a $C_{2-6}$ alkoxyalkyl group, a $C_{2-4}$ haloalkoxyalkyl group, a $C_{3-10}$ alkoxyalkoxyalkyl group, a $C_{4-12}$ alkoxyalkoxyalkoxyalkyl group, a cyclopropyl group, a $C_{1-4}$ cyanoalkyl group, a $C_{3-6}$ alkoxycarbonylalkyl group, a phenyl group (which may be substituted by a halogen atom, a nitro group, a $C_{1-4}$ alkyl group, a trifluoromethyl group, a phenoxy group or a methoxy group), a naphthyl group, a pyridyl group, a thienyl group or a 2-furyl group;

$R^{15}$ is a $C_{1-10}$ alkyl group, a $C_{2-6}$ haloalkyl group, a $C_{2-6}$ alkoxyalkyl group or a phenyl group;

$R^{16}$ is a hydrogen atom or a methyl group;

$R^{17}$ is a hydrogen atom, a $C_{1-6}$ alkyl group or a phenyl group (which may be substituted by a chlorine atom, a methyl group or a trifluoromethoxy group);

$R^{20}$ is a methyl group or a trifluoromethyl group;

$R^{21}$ is a hydrogen atom or a methyl group;

$R^{22}$ is an acetyl group or a methoxycarbonyl group;

each of $R^{23}$ and $R^{24}$ which are independent of each other, is a hydrogen atom, a chlorine atom, a $C_{1-4}$ alkyl group, a 1-triazolyl group or a group of the formula —$N(R^{25})R^{26}$;

each of $R^{25}$ and $R^{26}$ which are independent of each other, is a hydrogen atom, a $C_{1-4}$ alkyl group, a methoxy group or a $C_{2-4}$ alkoxyalkyl group;

$R^{27}$ is a $C_{1-4}$ alkyl group or a phenyl group (which may be substituted by a halogen atom or a methyl group);

each of $Q^1$ and $Q^2$ is a nitrogen atom or a group of the formula —$CR^9$;

m is an integer of 1 to 3; and n is 0 when $R^1$ is a cyano group or a $C_{1-4}$ alkylcarbamoyl group, or 0, 1 or 2 in other cases.

A preferred group of compounds of the above formula (II) may, for example, be a group of compounds wherein:

$R^1$ is a $C_{1-4}$ alkyl group, a cyanomethyl group, a hydroxyethyl group, a cyclopentyl group, a $C_{1-3}$ haloalkyl group, a phenyl group (which may be substituted by a halogen atom), a cyano group, a $C_{1-4}$ alkylcarbamoly group or a thiazolyl group;

each of $R^2$ and $R^3$ which are independent of each other, is a hydrogen atom, a methyl group or a $C_{1-2}$ alkoxycarbonyl group; or $R^1$ and $R^2$ may form a 5-membered ring together with the sulfur and carbon atoms to which they are respectively bonded;

$R^4$ is a hydrogen atom or a fluorine atom;

B is an aralkyl or arylcarbonyl group of the formula (B1) or (B2);

$R^9$ is a halogen atom, a trifluoromethyl group, a methoxy group, a $C_{1-2}$ fluoroalkoxy group or a phenoxy group (which may be substituted by a halogen atom);

$R^{10}$ is a hydrogen atom;

$R^{28}$ is a chlorine atom or a hydroxyl group;

each of $Q^1$ and $Q^2$ is a nitrogen atom or a group of the formula —$CR^9$;

m is an integer of 1 or 2; and n is 0 when $R^1$ is a cyano group or a $C_{1-4}$ alkylcarbamoyl group, or 0, 1 or 2 in other cases.

A preferred group of compounds of the above formula (III) may, for example be a compound wherein:

each of $R^2$, $R^3$ and $R^4$ is a hydrogen atom;

$R^9$ is a chlorine atom substituted at the 4-position;

each of $R^{12}$ and $R^{13}$ is a hydrogen atom, a group of the formula —$COR^{14}$ or a group of the formula —$COOR^{15}$;

$R^{14}$ is a $C_{1-4}$ alkyl group;

$R^{15}$ is a $C_{1-4}$ alkyl group;

$R^{29}$ is a chlorine atom, a mercapto group or a hydroxyl group;

each of $Q^1$ and $Q^2$ is a methine group; and m is 1.

Now, typical specific examples of the compounds of the formulas (I), (II) and (III) of the present invention will be given in Tables 1 to 35. The compound numbers used in the tables will be referred to in the subsequent description.

The compound of the formula (I) has a C=N bond and accordingly has two geometrical isomers i.e. entgegen (E) isomer and zusammen (Z) isomer. As the compound of the present invention, the E isomer and the Z isomer may be used alone, or a mixture thereof may be employed.

Further, the compound of the formula (I) of the present invention may have tautomers in some cases. For example, when the group of the formula =$CR^{23}R^{24}$ is represented by =$C(R^{23})$—$N(R^{25})R^{26}$, if $R^{25}$ is a hydrogen atom, a compound having a partial structure of —N=C($R^{23}$)NH—$R^{26}$ will be present in an equilibrium state with a tautonomer having a partial structure of —NH— C($R^{23}$)=N—$R^{26}$. Accordingly, it should be understood that among the compounds of the present invention, those which are capable of having tautonomers, have such corresponding tautonomers even if such tautonomers are not specifically mentioned.

TABLE 1

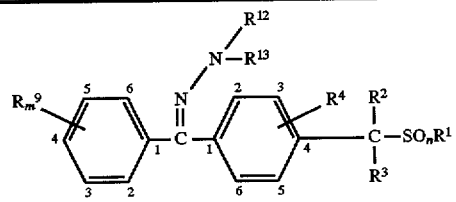

| Comp. No. | $R^9m$ | $R^1$ | $R^2$ | $R^3$ | $R^4$ | $R^{12}$ | $R^{13}$ | n | m.p. (°C.) or refractive index ($n_D^{30}$) |
|---|---|---|---|---|---|---|---|---|---|
| I-1 | 4-Cl | $CH_3$ | H | H | H | H | H | 0 | 1.6503 |
| I-2 | 4-Cl | $CH_3$ | H | H | H | H | H | 2 | 52–54 |
| I-3 | 4-Cl | $CH_3$ | H | H | H | H | $C(CH_3)=NSO_2CH_3$ | 2 | |
| I-4 | 4-Cl | $CH_3$ | H | H | H | H | $CH=NSO_2CH_3$ | 2 | |
| I-5 | 4-Cl | $CH_3$ | H | H | H | H | $CH=NSO_2C_4H_9$ | 2 | |
| I-6 | 4-Cl | $CH_3$ | H | H | H | H | $C(C_2H_5)=NSO_2CH_3$ | 0 | |
| I-7 | 4-Cl | $CH_3$ | H | H | H | H | $C(C_2H_5)=NSO_2CH_3$ | 1 | |
| I-8 | 4-Cl | $CH_3$ | H | H | H | H | $C(C_2H_5)=NSO_2CH_3$ | 2 | |
| I-9 | 4-Cl | $CH_3$ | H | H | H | $CH_3$ | $CH=NSO_2CH_3$ | 2 | |
| I-10 | 4-Cl | $CH_3$ | H | H | H | $COCH_3$ | H | 2 | 214–217 |
| I-11 | 4-Cl | $CH_3$ | H | H | H | $COC_2H_5$ | H | 0 | 91–93 |
| I-12 | 4-Cl | $CH_3$ | H | H | H | $COC_2H_5$ | $CH_3$ | 0 | 1.6319 |
| I-13 | 4-Cl | $CH_3$ | H | H | H | $COC_2H_5$ | $CH_3$ | 1 | 141–143 |
| I-14 | 4-Cl | $CH_3$ | H | H | H | $COC_2H_5$ | H | 1 | 153–156 |
| I-15 | 4-Cl | $CH_3$ | H | H | H | $COC_2H_5$ | H | 2 | 159–160 |
| I-16 | 4-Cl | $CH_3$ | H | H | H | $COC_3H_7$ | H | 2 | 173–175 |
| I-17 | 4-Cl | $CH_3$ | H | H | H | $COC_4H_9$ | H | 2 | 147–149 |

TABLE 1-continued

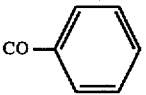

| Comp. No. | $R^9_m$ | $R^1$ | $R^2$ | $R^3$ | $R^4$ | $R^{12}$ | $R^{13}$ | n | m.p. (°C.) or refractive index ($n_D^{30}$) |
|---|---|---|---|---|---|---|---|---|---|
| I-18 | 4-Cl | $CH_3$ | H | H | H | $COC_5H_{11}$ | H | 0 | 93–96 |
| I-19 | 4-Cl | $CH_3$ | H | H | H | $COC_5H_{11}$ | $CH_3$ | 0 | 1.6097 |
| I-20 | 4-Cl | $CH_3$ | H | H | H | $COC_5H_{11}$ | $CH_3$ | 1 | 93–96 |
| I-21 | 4-Cl | $CH_3$ | H | H | H | $COC_5H_{11}$ | H | 1 | 1.6009 |
| I-22 | 4-Cl | $CH_3$ | H | H | H | $COC_5H_{11}$ | H | 2 | 110–113 |
| I-23 | 4-Cl | $CH_3$ | H | H | H | $COC_5H_{11}$ | $CH_3$ | 2 | 115–117 |
| I-24 | 4-Cl | $CH_3$ | H | H | H | $CHOC_5H_{11}$ | $CH_2OC_2H_5$ | 2 | 1.5722 |
| I-25 | 4-Cl | $CH_3$ | H | H | H | $COC_6H_{13}$ | H | 2 | 127–129 |
| I-26 | 4-Cl | $CH_3$ | H | H | H | $COC_8H_{17}$ | H | 2 | 116–118 |

TABLE 2

| Comp. No. | $R^9_m$ | $R^1$ | $R^2$ | $R^3$ | $R^4$ | $R^{12}$ | $R^{13}$ | n | m.p. (°C.) or refractive index ($n_D^{30}$) |
|---|---|---|---|---|---|---|---|---|---|
| I-27 | 4-Cl | $CH_3$ | H | H | H | $COCF_3$ | H | 2 | |
| I-28 | 4-Cl | $CH_3$ | H | H | H | 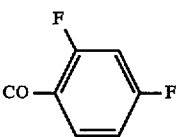 | H | 2 | |
| I-29 | 4-Cl | $CH_3$ | H | H | H | 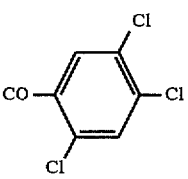 | H | 2 | |
| I-30 | 4-Cl | $CH_3$ | H | H | H | 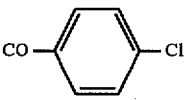 | H | 2 | |
| I-31 | 4-Cl | $CH_3$ | H | H | H |  | H | 2 | 174–176 |
| I-32 | 4-Cl | $CH_3$ | H | H | H |  | H | 2 | 209–211 |
| I-33 | 4-Cl | $CH_3$ | H | H | H |  | H | 0 | |
| I-34 | 4-Cl | $CH_3$ | H | H | H | $COCH_2CH_2CH_2Cl$ | H | 2 | 180–182 |
| I-35 | 4-Cl | $CH_3$ | H | H | H | $COCH_2COOC_2H_5$ | H | 0 | 1.6149 |
| I-36 | 4-Cl | $CH_3$ | H | H | H | $COCH_2CH_2OH$ | H | 2 | |
| I-37 | 4-Cl | $CH_3$ | H | H | H | $COCH_2CN$ | H | 2 | |
| I-38 | 4-Cl | $CH_3$ | H | H | H | $COCH_2OCH_2CF_3$ | H | 2 | |
| I-39 | 4-Cl | $CH_3$ | H | H | H | $COCH_2OCH_3$ | H | 2 | |

TABLE 2-continued

| Comp. No. | $R^9m$ | $R^1$ | $R^2$ | $R^3$ | $R^4$ | $R^{12}$ | $R^{13}$ | n | m.p. (°C.) or refractive index ($n_D^{30}$) |
|---|---|---|---|---|---|---|---|---|---|
| I-40 | 4-Cl | $CH_3$ | H | H | H | $CONH_2$ | H | 0 | Unmeasurable |
| I-41 | 4-Cl | $CH_3$ | H | H | H | $CONH_2$ | H | 1 | 195–197 |
| I-42 | 4-Cl | $CH_3$ | H | H | H | $CONH_2$ | H | 2 | 189–191 |
| I-43 | 4-Cl | $CH_3$ | H | H | H | COO—C$_6$H$_5$ | H | 2 | 94–96 |
| I-44 | 4-Cl | $CH_3$ | H | H | H | $COOC_2H_5$ | H | 2 | 164–166 |
| I-45 | 4-Cl | $CH_3$ | H | H | H | $COOC_2H_5$ | H | 0 | 1.6148 |
| I-46 | 4-Cl | $CH_3$ | H | H | H | $COOC_2H_5$ | H | 1 | 41–43 |
| I-47 | 4-Cl | $CH_3$ | H | H | H | $COOC_2H_5$ | $CH_3$ | 0 | 1.6042 |
| I-48 | 4-Cl | $CH_3$ | $CH_3$ | H | H | $COOC_2H_5$ | H | 2 | 162–165 |
| I-49 | 4-Cl | $CH_3$ | $CH_3$ | $CH_3$ | H | $COOC_2H_5$ | H | 2 | |

TABLE 3

| Comp. No. | $R^9m$ | $R^1$ | $R^2$ | $R^3$ | $R^4$ | $R^{12}$ | $R^{13}$ | n | m.p. (°C.) or refractive index ($n_D^{30}$) |
|---|---|---|---|---|---|---|---|---|---|
| I-50 | 4-Cl | $CH_3$ | H | H | H | $COOC_2H_5$ | $CH_2OC_2H_5$ | 2 | 125–128 |
| I-51 | 4-Cl | $CH_3$ | H | H | H | $COOC_2H_5$ | $CH_2OC_2H_5$ | 0 | 1.5853 |
| I-52 | 4-Cl | $CH_3$ | H | H | H | $COOC_3H_7$ | H | 0 | 1.6152 |
| I-53 | 4-Cl | $CH_3$ | H | H | H | $COOC_3H_7$ | H | 1 | 43–45 |
| I-54 | 4-Cl | $CH_3$ | H | H | H | $COOC_3H_7$ | H | 2 | 167–169 |
| I-55 | 4-Cl | $CH_3$ | H | H | H | $COOC_3H_7$-i | H | 2 | 159–160 |
| I-56 | 4-Cl | $CH_3$ | H | H | H | $COOC_4H_9$ | H | 2 | 68–70 |
| I-57 | 4-Cl | $CH_3$ | H | H | H | $COOC_4H_9$-t | H | 0 | 132–134 |
| I-58 | 4-Cl | $CH_3$ | H | H | H | $COOC_4H_9$-t | H | 1 | 89–93 |
| I-59 | 4-Cl | $CH_3$ | H | H | H | $COOC_4H_9$-t | H | 2 | 193–195 |
| I-60 | 4-Cl | $CH_3$ | H | H | H | $COOCH_2CH_2Cl$ | H | 2 | 65–67 |
| I-61 | 4-Cl | $CH_3$ | H | H | H | $COOCH_2CH_2OC_2H_5$ | H | 0 | 1.5822 |
| I-62 | 4-Cl | $CH_3$ | H | H | H | $COOCH_2CH_2OC_2H_5$ | H | 1 | 56–58 |
| I-63 | 4-Cl | $CH_3$ | H | H | H | $COOCH_2CH_2OC_2H_5$ | H | 2 | 47–49 |
| I-64 | 4-Cl | $CH_3$ | H | H | H | $COOCH_2CH_2OCH_3$ | H | 0 | 1.6179 |
| I-65 | 4-Cl | $CH_3$ | H | H | H | $COOCH_2CH_2OCH_3$ | H | 1 | 63–65 |
| I-66 | 4-Cl | $CH_3$ | H | H | H | $COOCH_2CH_2OCH_3$ | H | 2 | 70–72 |
| I-67 | 4-Cl | $CH_3$ | H | H | H | $COOCH_3$ | H | 0 | 40–42 |
| I-68 | 4-Cl | $CH_3$ | H | H | H | $COOCH_3$ | H | 1 | 176–177 |
| I-69 | 4-Cl | $CH_3$ | H | H | H | $COOCH_3$ | H | 2 | 197–199 |
| I-70 | 4-Cl | $CH_3$ | H | H | H | $COOCH_3$ | $CH_3$ | 0 | 1.6238 |
| I-71 | 4-Cl | $CH_3$ | H | H | H | $COOCH_3$ | $CHF_2$ | 0 | 1.5888 |
| I-72 | 4-Cl | $CH_3$ | H | H | H | $COOCH_3$ | $CH_3$ | 1 | 1.6082 |
| I-73 | 4-Cl | $CH_3$ | H | H | H | $COOCH_3$ | $CH_2OC_2H_5$ | 0 | 1.5911 |
| I-74 | 4-Cl | $CH_3$ | H | H | H | $COOCH_3$ | $CH_2SCH_3$ | 0 | 1.6187 |
| I-75 | 4-Cl | $CH_3$ | H | H | H | $COOCH_3$ | $CH_2OC_2H_5$ | 1 | 1.5949 |
| I-76 | 4-Cl | $CH_3$ | H | H | H | $COOCH_3$ | $CH_2OC_2H_5$ | 2 | 61–63 |
| I-77 | 4-Cl | $CH_3$ | H | H | H | $COOCH_3$ | $CH_3$ | 2 | 64–66 |
| I-78 | 4-Cl | $CH_3$ | H | H | H | $COOCH_3$ | $CH_2$—C$_6$H$_4$—Cl(4) | 0 | 1.6199 |
| I-79 | 4-Cl | $CH_3$ | H | H | H | $SO_2CH_2CF_3$ | H | 2 | |
| I-80 | 4-Cl | $CH_3$ | H | H | H | $SO_2CH_2Cl$ | H | 2 | |

TABLE 4

| Comp. No. | $R^9_m$ | $R^1$ | $R^2$ | $R^3$ | $R^4$ | $R^{12}$ | $R^{13}$ | n | m.p. (°C.) or refractive index ($n_D^{20}$) |
|---|---|---|---|---|---|---|---|---|---|
| I-81 | 4-Cl | $C_2H_5$ | H | H | H | H | H | 2 | 45–47 |
| I-82 | 4-Cl | $C_2H_5$ | H | H | H | $C(C_2H_5)=NSO_2CH_3$ | H | 0 | 1.6358 |
| I-83 | 4-Cl | $C_2H_5$ | H | H | H | $C(C_2H_5)=NSO_2CH_3$ | H | 1 | 45–47 |
| I-84 | 4-Cl | $C_2H_5$ | H | H | H | $C(C_2H_5)=NSO_2CH_3$ | H | 2 | 180–181 |
| I-85 | 4-Cl | $C_2H_5$ | H | H | H | $C(C_2H_5)=NSO_2CH_2CH_3$ | H | 0 | |
| I-86 | 4-Cl | $C_2H_5$ | H | H | H | $C(C_2H_5)=NSO_2CH_2CH_3$ | H | 1 | |
| I-87 | 4-Cl | $C_2H_5$ | H | H | H | $C(C_2H_5)=NSO_2CH_2CH_3$ | H | 2 | |
| I-88 | 4-Cl | $C_2H_5$ | H | H | H | $COCH_3$ | H | 2 | 193–195 |
| I-89 | 4-Cl | $C_2H_5$ | H | H | H | $COC_2H_5$ | H | 0 | 1.6025 |
| I-90 | 4-Cl | $C_2H_5$ | H | H | H | $COC_2H_5$ | H | 1 | 49–51 |
| I-91 | 4-Cl | $C_2H_5$ | H | H | H | $COC_2H_5$ | H | 0 | 43–45 |
| I-92 | 4-Cl | $C_2H_5$ | H | H | H | $COC_5H_{11}$ | H | 0 | 43–45 |
| I-93 | 4-Cl | $C_2H_5$ | H | H | H | $COC_5H_{11}$ | H | 1 | 98–100 |
| I-94 | 4-Cl | $C_2H_5$ | H | H | H | $COC_5H_{11}$ | H | 2 | 105–107 |
| I-95 | 4-Cl | $C_2H_5$ | H | H | H | $COCH_2COOC_2H_5$ | H | 2 | 1.5988 |
| I-96 | 4-Cl | $C_2H_5$ | H | H | H | $COOCH_3$ | H | 0 | 1.6269 |
| I-97 | 4-Cl | $C_2H_5$ | H | H | H | $COOCH_3$ | H | 1 | 145–147 |
| I-98 | 4-Cl | $C_2H_5$ | H | H | H | $COOCH_3$ | H | 2 | 160–162 |
| I-99 | 4-Cl | $C_2H_5$ | H | H | H | $COOCH_3$ | $CH_3$ | 0 | 1.6113 |
| I-100 | 4-Cl | $C_2H_5$ | H | H | H | $COOCH_3$ | $CH_3$ | 1 | 1.6059 |
| I-101 | 4-Cl | $C_2H_5$ | H | H | H | $COOCH_3$ | $CH_3$ | 2 | 1.5996 |
| I-102 | 4-Cl | $C_2H_5$ | H | H | H | $COOCH_3$ | $CHF_2$ | 0 | 1.5838 |
| I-103 | 4-Cl | $C_2H_5$ | H | H | H | $COOCH_3$ | $CHF_2$ | 1 | |
| I-104 | 4-Cl | $C_2H_5$ | H | H | H | $COOCH_3$ | $CHF_2$ | 2 | |
| I-105 | 4-Cl | $C_2H_5$ | H | H | H | $COOCH_3$ | $COOCH_3$ | 2 | |
| I-106 | 4-Cl | $C_2H_5$ | H | H | H | $COOCH_3$ | $COOCH_3$ | 0 | 1.5988 |
| I-107 | 4-Cl | $C_2H_5$ | H | H | H | $COOCH_3$ | $CONH_2$ | 2 | |
| I-108 | 4-Cl | $C_2H_5$ | H | H | H | $COOCH_3$ | $C_2H_5$ | 2 | |
| I-109 | 4-Cl | $C_2H_5$ | H | H | H | $COOCH_3$ | $CH_2OCH_3$ | 2 | |
| I-110 | 4-Cl | $C_2H_5$ | H | H | H | $COOCH_3$ | $COC_2H_5$ | 2 | |
| I-111 | 4-Cl | $C_2H_5$ | H | H | H | $COOCH_3$ | $CH_2SCH_3$ | 2 | |

TABLE 5

| Comp. No. | $R^9_m$ | $R^1$ | $R^2$ | $R^3$ | $R^4$ | $R^{12}$ | $R^{13}$ | n | m.p. (°C.) or refractive index ($n_D^{30}$) |
|---|---|---|---|---|---|---|---|---|---|
| I-112 | 4-Cl | $C_2H_5$ | H | H | H | $COOCH_3$ | $CH_2$–C$_6$H$_5$ | 2 | |
| I-113 | 4-Cl | $C_2H_5$ | H | H | H | $COOCH_3$ | $CHF_2$ | 2 | |
| I-114 | 4-Cl | $C_2H_5$ | H | H | H | $COOC_2H_5$ | H | 0 | 1.6198 |
| I-115 | 4-Cl | $C_2H_5$ | H | H | H | $COOC_2H_5$ | H | 1 | 58–61 |
| I-116 | 4-Cl | $C_2H_5$ | H | H | H | $COOC_2H_5$ | H | 2 | 68–70 |
| I-117 | 4-Cl | $C_2H_5$ | H | H | H | $COOC_3H_7$ | H | 2 | 152–155 |
| I-118 | 4-Cl | $C_2H_5$ | H | H | H | $COOC_4H_9$ | H | 2 | 127–130 |
| I-119 | 4-Cl | $C_2H_5$ | H | H | H | $COOC_4H_9$-t | H | 2 | 173–176 |
| I-120 | 4-Cl | $C_2H_5$ | H | H | H | $COOC_4H_9$-t | H | 1 | |
| I-121 | 4-Cl | $C_2H_5$ | H | H | H | $COOCH_2CH_2OC_2H_5$ | H | 2 | 1.5748 |
| I-122 | 4-Cl | $C_2H_5$ | H | H | H | $SO_2CH_3$ | H | 2 | 86–88 |
| I-123 | 4-Cl | $C_3H_7$ | H | H | H | $COCH_3$ | H | 2 | |
| I-124 | 4-Cl | $C_3H_7$ | H | H | H | $COC_2H_5$ | H | 2 | 120–122 |
| I-125 | 4-Cl | $C_3H_7$ | H | H | H | $COC_5H_{11}$ | H | 2 | 116–117 |
| I-126 | 4-Cl | $C_3H_7$ | H | H | H | $COOC_2H_5$ | H | 0 | |
| I-127 | 4-Cl | $C_3H_7$ | H | H | H | $COOC_2H_5$ | H | 1 | |
| I-128 | 4-Cl | $C_3H_7$ | H | H | H | $COOC_2H_5$ | H | 2 | 132–134 |
| I-129 | 4-Cl | $C_3H_7$ | H | H | H | H | H | 2 | 88–90 |
| I-130 | 4-Cl | $C_3H_7$-i | H | H | H | $COC_2H_5$ | H | 2 | 130–132 |
| I-131 | 4-Cl | $C_3H_7$-i | H | H | H | $COOC_2H_5$ | H | 2 | |
| I-132 | 4-Cl | $C_3H_7$-i | H | H | H | $COOC_2H_5$ | H | 2 | 82–84 |
| I-133 | 4-Cl | $C_3H_7$-i | H | H | H | H | H | 2 | 68–70 |
| I-134 | 4-Cl | $C_4H_9$ | H | H | H | $COOC_2H_5$ | H | 2 | 114–116 |
| I-135 | 4-Cl | $CF_3$ | H | H | H | H | H | 0 | 1.5969 |
| I-136 | 4-Cl | $CF_3$ | H | H | H | H | H | 2 | 1.5871 |

TABLE 5-continued

| Comp. No. | $R^9m$ | $R^1$ | $R^2$ | $R^3$ | $R^4$ | $R^{12}$ | $R^{13}$ | n | m.p. (°C.) or refractive index ($n_D^{30}$) |
|---|---|---|---|---|---|---|---|---|---|
| I-137 | 4-Cl | $CF_3$ | H | H | H | $CH=NSO_2CH_3$ | H | 2 | 63–65 |
| I-138 | 4-Cl | $CF_3$ | H | H | H | $CH=NSO_2$—C$_6$H$_5$ | H | 2 | 74–78 |
| I-139 | 4-Cl | $CF_3$ | H | H | H | $CH=NSO_2CH_3$ | H | 0 |  |

TABLE 6

| Comp. No. | $R^9m$ | $R^1$ | $R^2$ | $R^3$ | $R^4$ | $R^{12}$ | $R^{13}$ | n | m.p. (°C.) or refractive index ($n_D^{30}$) |
|---|---|---|---|---|---|---|---|---|---|
| I-140 | 4-Cl | $CF_3$ | H | H | H | $C(CH_3)=CHCOCH_3$ | H | 2 | 121–123 |
| I-141 | 4-Cl | $CF_3$ | H | H | H | $C(CH_3)=CHCOOCH_3$ | H | 2 | 96–98 |
| I-142 | 4-Cl | $CF_3$ | H | H | H | $CH=CHCOCH_3$ | H | 2 |  |
| I-143 | 4-Cl | $CF_3$ | H | H | H | $CH=CHCOCH_3$ | H | 1 |  |
| I-144 | 4-Cl | $CF_3$ | H | H | H | $C(C_2H_5)=NSO_2CH_3$ | H | 0 |  |
| I-145 | 4-Cl | $CF_3$ | H | H | H | $C(C_2H_5)=NSO_2CH_3$ | H | 1 |  |
| I-146 | 4-Cl | $CF_3$ | H | H | H | $C(C_2H_5)=NSO_2CH_3$ | H | 2 |  |
| I-147 | 4-Cl | $CF_3$ | H | H | H | $CH_2CF_3$ | H | 0 |  |
| I-148 | 4-Cl | $CF_3$ | H | H | H | $CH_2CF_3$ | H | 2 | 1.5539 |
| I-149 | 4-Cl | $CF_3$ | H | H | H | $COC_2H_5$ | H | 2 | 130–132 |
| I-150 | 4-Cl | $CF_3$ | H | H | H | $COC_2H_5$ | H | 0 | 121–123 |
| I-151 | 4-Cl | $CF_3$ | H | H | H | $COC_2H_5$ | H | 1 | 152–154 |
| I-152 | 4-Cl | $CF_3$ | H | H | H | $COC_2H_5$ | H | 2 |  |
| I-153 | 4-Cl | $CF_3$ | H | H | H | $COC_3H_7$ | H | 2 | 125–126 |
| I-154 | 4-Cl | $CF_3$ | H | H | H | $COC_4H_9$ | H | 0 | 59–61 |
| I-155 | 4-Cl | $CF_3$ | H | H | H | $COC_4H_9$ | H | 2 | 153–156 |
| I-156 | 4-Cl | $CF_3$ | H | H | H | $COC_5H_{11}$ | H | 2 | 122–124 |
| I-157 | 4-Cl | $CF_3$ | H | H | H | $COCF_3$ | H | 2 | 54–56 |
| I-158 | 4-Cl | $CF_3$ | H | H | H | $COCF_3$ | H | 0 | 1.5659 |
| I-159 | 4-Cl | $CF_3$ | H | H | H | $COCH_2OC_2H_4OC_2H_4OC_2H_5$ | H | 2 | 78–80 |
| I-160 | 4-Cl | $CF_3$ | H | H | H | $COCH_2OC_2H_4OC_2H_5$ | H | 2 | 101–103 |
| I-161 | 4-Cl | $CF_3$ | H | H | H | $COCH_2OC_2H_5$ | H | 2 | 126–128 |
| I-162 | 4-Cl | $CF_3$ | H | H | H | $COCH_2OCH_2CF_3$ | H | 2 | 120–122 |
| I-163 | 4-Cl | $CF_3$ | H | H | H | $COCH_3$ | H | 0 | 1.5972 |
| I-164 | 4-Cl | $CF_3$ | H | H | H | $COCH_3$ | H | 1 | 129–130 |
| I-165 | 4-Cl | $CF_3$ | H | H | H | $COCH_3$ | H | 2 | 112–114 |
| I-166 | 4-Cl | $CF_3$ | H | H | H | $CONH$—C$_6$H$_5$ | H | 2 | 81–83 |
| I-167 | 4-Cl | $CF_3$ | H | H | H | $CONH$—C$_6$H$_3$F$_2$ (2,4-difluorophenyl) | H | 2 |  |

TABLE 7

| Comp. No. | $R^9m$ | $R^1$ | $R^2$ | $R^3$ | $R^4$ | $R^{12}$ | $R^{13}$ | n | m.p. (°C.) or refractive index ($n_D^{30}$) |
|---|---|---|---|---|---|---|---|---|---|
| I-168 | 4-Cl | $CF_3$ | H | H | H | CONH-(2,6-diCl-phenyl) | H | 2 | 132–134 |
| I-169 | 4-Cl | $CF_3$ | H | H | H | CONH-(4-$CH_3$-phenyl) | H | 2 | 193–195 |
| I-170 | 4-Cl | $CF_3$ | H | H | H | $CONH_2$ | H | 2 | |
| I-171 | 4-Cl | $CF_3$ | H | H | H | $CONHC_4H_9$ | H | 2 | 179–181 |
| I-172 | 4-Cl | $CF_3$ | H | H | H | $CONHCH_3$ | H | 2 | |
| I-173 | 4-Cl | $CF_3$ | H | H | H | $COOC_2H_5$ | H | 0 | 75–76 |
| I-174 | 4-Cl | $CF_3$ | H | H | H | $COOC_2H_5$ | H | 1 | 178–180 |
| I-175 | 4-Cl | $CF_3$ | H | H | H | $COOC_2H_5$ | H | 2 | 148–150 |
| I-176 | 4-Cl | $CF_3$ | H | H | H | $COOCH_3$ | H | 0 | 1.5921 |
| I-177 | 4-Cl | $CF_3$ | H | H | H | $COOCH_3$ | H | 1 | 181–183 |
| I-178 | 4-Cl | $CF_3$ | H | H | H | $COOCH_3$ | H | 2 | 151–153 |
| I-179 | 4-Cl | $CF_3$ | H | H | H | $COOCH_3$ | $CH_3$ | 0 | 1.5802 |
| I-180 | 4-Cl | $CF_3$ | H | H | H | $COOCH_3$ | $CH_3$ | 1 | 1.5820 |
| I-181 | 4-Cl | $CF_3$ | H | H | H | $SO_2CF_3$ | H | 2 | 32–34 |
| I-182 | 4-Cl | $CF_3$ | H | H | H | $SO_2CH_3$ | H | 2 | 64–65 |
| I-183 | 4-Cl | $CHF_2$ | H | H | H | $COC_2H_5$ | H | 0 | 1.6203 |
| I-184 | 4-Cl | $CHF_2$ | H | H | H | $COC_2H_5$ | H | 2 | 158–160 |
| I-185 | 4-Cl | $CHF_2$ | H | H | H | $COOC_2H_5$ | H | 2 | 197–199 |
| I-186 | 4-Cl | $CHF_2$ | H | H | H | $COOCH_3$ | $CH_3$ | 0 | 1.5981 |
| I-187 | 4-Cl | $CHF_2$ | H | H | H | $COOCH_3$ | H | 0 | 1.6213 |
| I-188 | 4-Cl | $CHF_2$ | H | H | H | $COOCH_3$ | H | 1 | 71–73 |
| I-189 | 4-Cl | $CHF_2$ | H | H | H | $COOCH_3$ | H | 2 | 171–173 |
| I-190 | 4-Cl | $CHF_2$ | H | H | H | H | H | 0 | 1.6273 |
| I-191 | 4-Cl | $C_2F_5$ | H | H | H | $COOCH_3$ | H | 2 | 166–168 |
| I-192 | 4-Cl | $CF_2CHF_2$ | H | H | H | $COOCH_3$ | H | 0 | 1.5801 |
| I-193 | 4-Cl | $C_2F_5$ | H | H | H | $COOCH_3$ | H | 0 | 1.5649 |
| I-194 | 4-Cl | $C_2F_5$ | H | H | H | $COOC_2H_5$ | H | 0 | 1.5629 |

TABLE 8

| Comp. No. | $R^9m$ | $R^1$ | $R^2$ | $R^3$ | $R^4$ | $R^{12}$ | $R^{13}$ | n | m.p. (°C.) or refractive index ($n_D^{30}$) |
|---|---|---|---|---|---|---|---|---|---|
| I-195 | 4-Cl | $C_2F_5$ | H | H | H | $COOC_2H_5$ | H | 2 | 94–97 |
| I-196 | 4-Cl | $CF_2CHF_2$ | H | H | H | $COOC_2H_5$ | H | 2 | 136–137 |
| I-197 | 4-Cl | $CF_2CHF_2$ | H | H | H | $COOCH_3$ | H | 2 | 145–148 |
| I-198 | 4-Cl | $C_3F_7$ | H | H | H | $COOC_2H_5$ | H | 2 | |
| I-199 | 4-Cl | $C_3F_7$-i | H | H | H | $COOC_2H_5$ | H | 2 | |
| I-200 | 4-Cl | $CF_2CHFCF_3$ | H | H | H | $COOC_2H_5$ | H | 0 | |
| I-201 | 4-Cl | $CF_2CHFCF_3$ | H | H | H | $COOC_2H_5$ | H | 1 | |
| I-202 | 4-Cl | $CF_2CHFCF_3$ | H | H | H | $COOC_2H_5$ | H | 2 | |
| I-203 | 4-Cl | $CH_2$-phenyl | H | H | H | $COOC_2H_5$ | H | 0 | |
| I-204 | 4-Cl | $CH_2Br$ | H | H | H | $COC_2H_5$ | H | 2 | |
| I-205 | 4-Cl | $CH_2Br$ | H | H | H | $COOC_2H_5$ | H | 2 | |
| I-206 | 4-Cl | $CH_2CF_3$ | H | H | H | $COOC_2H_5$ | H | 2 | Unmeasurable |
| I-207 | 4-Cl | $CH_2CF_3$ | H | H | H | $COOCH_3$ | H | 2 | 154–156 |
| I-208 | 4-Cl | $CHCl_2$ | H | H | H | $COOC_2H_5$ | H | 2 | |
| I-209 | 4-Cl | $CH_2CH_2OH$ | H | H | H | $COOC_2H_5$ | H | 0 | 1.6141 |
| I-210 | 4-Cl | $CH_2CH_2OH$ | H | H | H | $COOC_2H_5$ | H | 2 | 75–78 |

TABLE 8-continued

| Comp. No. | R⁹m | R¹ | R² | R³ | R⁴ | R¹² | R¹³ | n | m.p. (°C.) or refractive index ($n_D^{30}$) |
|---|---|---|---|---|---|---|---|---|---|
| I-211 | 4-Cl | $CH_2Cl$ | H | H | H | CO—△ | H | 2 | 176–178 |
| I-212 | 4-Cl | $CH_2Cl$ | H | H | H | $COC_2H_5$ | H | 2 | 63–65 |
| I-213 | 4-Cl | $CH_2Cl$ | H | H | H | $COC_3H_7$ | H | 2 | 112–114 |
| I-214 | 4-Cl | $CH_2Cl$ | H | H | H | $COC_5H_{11}$ | H | 2 | 91–93 |
| I-215 | 4-Cl | $CH_2Cl$ | H | H | H | $COCH_2Cl$ | H | 2 | 180–181 |
| I-216 | 4-Cl | $CH_2Cl$ | H | H | H | $COCH_2CN$ | H | 2 | 68–70 |
| I-217 | 4-Cl | $CH_2Cl$ | H | H | H | $COCH_3$ | H | 2 | 185–187 |
| I-218 | 4-Cl | $CH_2Cl$ | H | H | H | $COOC_2H_5$ | H | 2 | 166–168 |
| I-219 | 4-Cl | $CH_2Cl$ | H | H | H | $COOC_3H_7$ | H | 2 | |
| I-220 | 4-Cl | $CH_2Cl$ | H | H | H | $COOCH_2CH_2OCH_3$ | H | 2 | 56–58 |
| I-221 | 4-Cl | $CH_2Cl$ | H | H | H | $COOCH_2CH_2OC_2H_5$ | H | 2 | 60–62 |
| I-222 | 4-Cl | $CH_2Cl$ | H | H | H | $COOC_3H_7$ | H | 2 | 105–107 |

TABLE 9

| Comp. No. | R⁹m | R¹ | R² | R³ | R⁴ | R¹² | R¹³ | n | m.p. (°C.) or refractive index ($n_D^{30}$) |
|---|---|---|---|---|---|---|---|---|---|
| I-223 | 4-Cl | $CH_2Cl$ | H | H | H | $COOCH_3$ | H | 2 | 160–162 |
| I-224 | 4-Cl | $CH_2Cl$ | H | H | H | H | H | 2 | 1.6258 |
| I-225 | 4-Cl | $CH_2CN$ | H | H | H | $COOC_2H_5$ | H | 0 | 89–91 |
| I-226 | 4-Cl | $CH_2CN$ | H | H | H | $COOC_2H_5$ | H | 2 | 81–83 |
| I-227 | 4-Cl | $CH_2CH_2CN$ | H | H | H | $COOC_2H_5$ | H | 0 | |
| I-228 | 4-Cl | $CH_2CN$ | H | H | H | $COOC_2H_5$ | H | 1 | |
| I-229 | 4-Cl | $CH_2CH_2CN$ | H | H | H | $COOC_2H_5$ | H | 1 | |
| I-230 | 4-Cl | $CH_2CH_2CN$ | H | H | H | $COOC_2H_5$ | H | 2 | |
| I-231 | 4-Cl | $CH_2$—C₆H₄—Cl | H | H | H | $COOC_2H_5$ | H | 0 | |
| I-232 | 4-Cl | CN | H | H | H | $COOC_2H_5$ | H | 0 | 1.6228 |
| I-233 | 4-Cl | CN | H | H | H | $COOC_2H_5$ | H | 1 | |
| I-234 | 4-Cl | 2-Cl-C₆H₄ | H | H | H | $COOC_2H_5$ | H | 2 | |
| I-235 | 4-Cl | 4-CH₃-C₆H₄ | H | H | H | $COOC_2H_5$ | H | 2 | 176–179 |
| I-236 | 4-Cl | 4-CH₃-C₆H₄ | H | H | H | $COOC_2H_5$ | H | 1 | |
| I-237 | 4-Cl | thiazolyl | H | H | H | $COOC_2H_5$ | H | 2 | |
| I-238 | 4-Cl | thiazolyl | H | H | H | $COOC_2H_5$ | H | 0 | 1.6524 |

TABLE 9-continued

| Comp. No. | R⁹m | R¹ | R² | R³ | R⁴ | R¹² | R¹³ | n | m.p. (°C.) or refractive index ($n_D^{30}$) |
|---|---|---|---|---|---|---|---|---|---|
| I-239 | 4-Cl | cyclopropyl | H | H | H | COOC₂H₅ | H | 0 | |
| I-240 | 4-Cl | cyclopropyl | H | H | H | COOC₂H₅ | H | 1 | |
| I-241 | 4-Cl | cyclopropyl | H | H | H | COOC₂H₅ | H | 2 | |
| I-242 | 4-Cl | cyclobutyl | H | H | H | COOC₂H₅ | H | 0 | |

TABLE 10

| Comp. No. | R⁹m | R¹ | R² | R³ | R⁴ | R¹² | R¹³ | n | m.p. (°C.) or refractive index ($n_D^{30}$) |
|---|---|---|---|---|---|---|---|---|---|
| I-243 | 4-Cl | cyclobutyl | H | H | H | COOC₂H₅ | H | 1 | |
| I-244 | 4-Cl | cyclobutyl | H | H | H | COOC₂H₅ | H | 2 | |
| I-245 | 4-Cl | cyclopentyl | H | H | H | COOC₂H₅ | H | 0 | |
| I-246 | 4-Cl | cyclopentyl | H | H | H | COOC₂H₅ | H | 1 | |
| I-247 | 4-Cl | cyclopentyl | H | H | H | COOC₂H₅ | H | 2 | 76–79 |
| I-248 | 4-Cl | CH₃ | CH₃ | CH₃ | H | COC₅H₁₁ | CH3 | 2 | 94–96 |
| I-249 | H | CH₃ | H | H | H | COOC₂H₅ | H | 2 | 143–144 |
| I-250 | H | CF₃ | H | H | H | COC₂H₅ | H | 2 | 107–109 |
| I-251 | H | CF₃ | H | H | H | H | H | 2 | 103–110 |
| I-252 | 4-F | CF₃ | H | H | H | H | H | 2 | 73–76 |
| I-253 | 4-F | CF₃ | H | H | H | COC₂H₅ | H | 2 | 129–130 |
| I-254 | 4-F | CH₃ | H | H | H | COOCH3 | H | 0 | 1.6182 |
| I-255 | 4-F | CH₃ | H | H | H | COOCH3 | H | 2 | 167–169 |
| I-256 | 4-F | CH₃ | H | H | H | COOC₂H₅ | H | 2 | 148–149 |
| I-257 | 4-F | C₂H₅ | H | H | H | COOCH₃ | H | 0 | 84–85 |
| I-258 | 4-Br | CF₃ | H | H | H | COC₂H₅ | H | 2 | 143–145 |
| I-259 | 4-Br | CH₃ | H | H | H | COOC₂H₅ | H | 2 | 158–159 |
| I-260 | 4-Br | CF₃ | H | H | H | H | H | 2 | 66–68 |
| I-261 | 2-F, 4-Cl | CF₃ | H | H | H | COOC₂H₅ | H | 0 | 83–85 |
| I-262 | 3,4,5-Cl₃ | CF₃ | H | H | H | COOC₂H₅ | H | 2 | |
| I-263 | 3-F, 4-Cl | CF₃ | H | H | H | COOC₂H₅ | H | 2 | 54–55 |
| I-264 | 3-F, 4-Cl | CH₃ | H | H | H | COOC₂H₅ | H | 2 | 54–56 |
| I-265 | 4-CH₃ | CF₃ | H | H | H | COC₂H₅ | H | 2 | 115–118 |
| I-266 | 4-CH₃ | CH₃ | H | H | H | COOC₂H₅ | H | 2 | 203–204 |

TABLE 11

| Comp. No. | R⁹m | R¹ | R² | R³ | R⁴ | R¹² | R¹³ | n | m.p. (°C.) or refractive index ($n_D^{20}$) |
|---|---|---|---|---|---|---|---|---|---|
| I-267 | 4-C₄H₉-t | CF₃ | H | H | H | COOC₂H₅ | H | 2 | 164–166 |
| I-268 | 4-CF₃ | CF₃ | H | H | H | H | H | 2 | 1.5592 |
| I-269 | 4-OCH3 | CF₃ | H | H | H | H | H | 2 | 135–138 |
| I-270 | 4-CHF₂ | CF₃ | H | H | H | COOC₂H₅ | H | 2 | |
| I-271 | 4-CHF₂ | CF₃ | H | H | H | COOC₂H₅ | H | 1 | |
| I-272 | 4-CHF₂ | CF₃ | H | H | H | COOC₂H₅ | H | 0 | |
| I-273 | 4-SO₂CH₃ | CH₃ | H | H | H | COOC₂H₅ | H | 2 | 120–122 |
| I-274 | 4-CF₃ | CF₃ | H | H | H | COC₂H₅ | H | 2 | 189–190 |
| I-275 | 4-CF₃ | CH₃ | H | H | H | COOC₂H₅ | H | 2 | |
| I-276 | 4-CF₃ | CH₃ | H | H | H | COOC₂H₅ | H | 1 | |
| I-277 | 4-CN | CF₃ | H | H | H | COC₂H₅ | H | 2 | 195–197 |
| I-278 | 4-CN | CF₃ | H | H | H | H | H | 2 | 95–96 |
| I-279 | 4-CN | CH₃ | H | H | H | COOC₂H₅ | H | 2 | |
| I-280 | 4-NO₂ | CF₃ | H | H | H | COC₂H₅ | H | 2 | 193–194 |
| I-281 | 4-NO₂ | CF₃ | H | H | H | H | H | 2 | 130–133 |
| I-282 | 4-NO₂ | CF₃ | H | H | H | COOC₂H₅ | H | 2 | 65–67 |
| I-283 | 4-OCH₃ | CF₃ | H | H | H | COC₂H₅ | H | 2 | 121–123 |
| I-284 | 4-OCH₃ | CH₃ | H | H | H | COOC₂H₅ | H | 2 | 151–152 |
| I-285 | 4-Cl | CH₃ | H | H | H | —COCH₂CH₂CH₂— | | 2 | 117–120 |
| I-286 | 4-Cl | —CH₂CH₂CH₂— | H | H | H | COOC₂H₅ | H | 2 | 100–103 |
| I-287 | 4-Cl | —CH₂CH₂CH₂— | H | H | H | COOC₂H₅ | H | 0 | |
| I-288 | 4-Cl | —CH₂CH₂CH₂— | H | H | H | COOC₂H₅ | H | 0 | |
| I-289 | 4-Cl | —CH₂CH₂CH₂— | H | H | H | COOC₂H₅ | H | 0 | |
| I-290 | 4-Cl | CH₃ | H | H | H | COC₄H₉ | CH₂OC₂H₅ | 2 | 1.5838 |
| I-291 | 4-Cl | CH₃ | H | H | H | COC₃H₇ | CH₂OC₂H₅ | 2 | 1.5835 |
| I-292 | 4-Cl | CH₃ | H | H | H | COC₇H₁₅ | H | 2 | 121–123 |
| I-293 | 4-Cl | CH₃ | H | H | H | COC₂H₅ | CH₃ | 2 | 171–173 |

TABLE 12

| Comp. No. | R⁹m | R¹ | R² | R³ | R⁴ | R¹² | R¹³ | n | m.p. (°C.) or refractive index ($n_D^{30}$) |
|---|---|---|---|---|---|---|---|---|---|
| I-294 | 3-F, 4-Cl | CH₃ | H | H | H | COOCH₃ | H | 2 | 83–85 |
| I-295 | 4-Cl | CH₃ | H | H | H | COOCH₃ | C₂H₅ | 0 | 1.6046 |
| I-296 | 4-Cl | CH₃ | H | H | H | COOCH₃ | C₂H₅ | 1 | 48–50 |
| I-297 | 4-Cl | CH₃ | H | H | H | COOCH₃ | C₂H₅ | 2 | 56–58 |
| I-298 | 4-Cl | CH₃ | H | H | H | COOCH₃ | CH₂OC₂H₄OCH₃ | 0 | 1.5889 |
| I-299 | 4-Cl | CH₃ | H | H | H | COOCH₃ | CH₂OC₂H₄OCH₃ | 2 | 1.5651 |
| I-300 | 4-Cl | CH₃ | H | H | H | COOCH₃ | CH₂OC₂H₄OCH₃ | 1 | 1.5931 |
| I-301 | 4-Cl | CH₃ | H | H | H | COC₂H₅ | CH₂OC₂H₅ | 0 | 1.6019 |
| I-302 | 4-Cl | CH₃ | H | H | H | COC₂H₅ | CH₂OC₂H₅ | 2 | 41–43 |
| I-303 | 4-Cl | CH₃ | H | H | H | COCH₂OC₂H₅ | H | 0 | 79–80 |
| I-304 | 4-Cl | CH₃ | H | H | H | COCH₂OC₂H₅ | H | 2 | 76–78 |
| I-305 | 4-Cl | CH₃ | H | H | H | COCH₂OC₂H₅ | CH₂OC₂H₅ | 0 | 1.5909 |
| I-306 | 4-Cl | CH₃ | H | H | H | COCH₂OC₂H₅ | CH₂OC₂H₅ | 2 | 1.5869 |
| I-307 | 4-Cl | CH₃ | H | H | H | COOCH₃ | 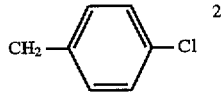 | 2 | 65–67 |
| I-308 | 4-Cl | CH₃ | H | H | H | COOCH₃ | 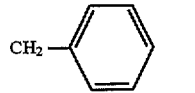 | 0 | 1.6670 |
| I-309 | 4-Cl | CH₃ | H | H | H | COOCH₃ | 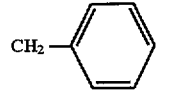 | 2 | 59–60 |
| I-310 | 4-Cl | CH₃ | H | H | H | C(CH₃)=CCOCH₃ | H | 2 | 182–184 |
| I-311 | 4-Cl | CH₃ | H | H | H | COOCH₃ | C₄H₉ | 0 | 1.5714 |
| I-312 | 4-Cl | CH₃ | H | H | H | COOCH₃ | C₄H₉ | 2 | 42–43 |

TABLE 12-continued

| Comp. No. | R⁹m | R¹ | R² | R³ | R⁴ | R¹² | R¹³ | n | m.p. (°C.) or refractive index ($n_D^{30}$) |
|---|---|---|---|---|---|---|---|---|---|
| I-313 | 4-Cl | CH₃ | H | H | 3-F | COOCH₃ | H | 2 | 109–110 |
| I-314 | 4-Cl | CH₃ | H | H | 3-F | COOC₂H₅ | H | 2 | 144–146 |
| I-315 | 4-Cl | CH₃ | H | H | H | COOC₅H₁₁ | H | 2 | 59–61 |
| I-316 | 4-Cl | CH₃ | H | H | H | COOC₄H₉ | H | 0 | 74–75 |
| I-317 | 4-F | CH₃ | H | H | H | COOCH₃ | CH₂OC₂H₅ | 0 | 1.5791 |
| I-318 | 4-F | CH₃ | H | H | H | COOCH₃ | CH₂OC₂H₅ | 2 | 38–40 |
| I-319 | 4-F | CH₃ | H | H | H | COOCH₃ | CH₂OC₂H₄OCH₃ | 0 | 1.5732 |
| I-320 | 4-F | CH₃ | H | H | H | COOCH₃ | CH₂OC₂H₄OCH₃ | 2 | 1.5702 |

TABLE 13

| Comp. No. | R⁹m | R¹ | R² | R³ | R⁴ | R¹² | R¹³ | n | m.p. (°C.) or refractive index ($n_D^{30}$) |
|---|---|---|---|---|---|---|---|---|---|
| I-321 | 4-F | CH₃ | H | H | H | COOCH₃ |  | 0 | 1.5699 |
| I-322 | 4-CH₂SO₂CH₃ | CH₃ | H | H | H | COOC₂H₅ | H | 2 | 193–194 |
| I-323 | 4-F | CH₃ | H | H | H | COOCH₃ |  | 2 | 57–58 |
| I-324 | 4-OCHF₂ | CH₃ | H | H | H | COOCH₃ | H | 2 | 93–95 |
| I-325 | 4-OCH₂CF₃ | CH₃ | H | H | H | COOCH₃ | H | 2 | 152–154 |
| I-326 | 4-OCF₃ | CH₃ | H | H | H | COOC₂H₅ | H | 2 | 151–153 |
| I-327 | 4-OSO₂CF₃ | CH₃ | H | H | H | COOC₂H₅ | H | 2 | 163–164 |
| I-328 | 4-Cl | C₂H₅ | H | H | H | COOCH₃ | CH₂OC₂H₅ | 0 | 1.5831 |
| I-329 | 4-Cl | C₂H₅ | H | H | H | COOCH₃ | CH₂OC₂H₅ | 2 | 1.5735 |
| I-330 | 4-Cl | C₂H₅ | H | H | H | COOCH₃ | CH₂OC₂H₅ | 1 | 1.5812 |
| I-331 | 4-Cl | C₂H₅ | H | H | H | COC₅H₁₁ | CH₃ | 0 | 1.6025 |
| I-332 | 4-Cl | C₂H₅ | H | H | H | COC₅H₁₁ | CH₃ | 2 | 1.5918 |
| I-333 | 4-Cl | C₂H₅ | H | H | H | COC₅H₁₁ | CH₂OC₂H₅ | 0 | 1.5725 |
| I-334 | 4-Cl | C₂H₅ | H | H | H | COC₅H₁₁ | CH₂OC₂H₅ | 2 | 1.5659 |
| I-335 | 4-Cl | C₂H₅ | H | H | H | COOCH₃ | CH₂OC₂H₄OCH₃ | 2 | 1.5751 |
| I-336 | 4-Cl | C₂H₅ | H | H | H | COOC₄H₉ | H | 0 | 1.5899 |
| I-337 | 4-Cl | C₂H₅ | H | H | H | COC₅H₁₁H | CH₂OC₂H₅ | 1 | 1.5682 |
| I-338 | 4-Cl | C₂H₅ | H | H | H | COOC₄H₉ | H | 1 | 1.6029 |
| I-339 | 4-Cl | C₂H₅ | H | H | H | COOC₄H₉ | CH₂OC₂H₅ | 0 | 1.5631 |
| I-340 | 4-Cl | C₂H₅ | H | H | H | COOC₄H₉ | CH₂OC₂H₅ | 2 | 1.5603 |
| I-341 | 4-Cl | C₂H₅ | H | H | H | COOC₄H₉ | CH₂OC₂H₅ | 1 | 1.5728 |
| I-342 | 4-Cl | C₂H₅ | H | H | H | 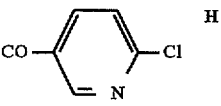 | H | 0 | 1.6557 |
| I-343 | 2-F, 4-Cl | C₂H₅ | H | H | H | COOCH₃ | H | 2 | 172–174 |
| I-344 | 3-F, 4-Cl | C₂H₅ | H | H | H | COOCH₃ | H | 2 | 165–167 |
| I-345 | 4-Cl | C₂H₅ | H | H | H | 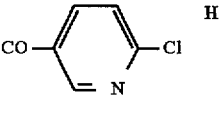 | H | 1 | 78–80 |
| I-346 | 4-Cl | C₂H₅ | H | H | H | COCH₃ | COOCH3 | 0 | 1.6201 |

TABLE 14

| Comp. No. | $R^9m$ | $R^1$ | $R^2$ | $R^3$ | $R^4$ | $R^{12}$ | $R^{13}$ | n | m.p. (°C.) or refractive index ($n_D^{30}$) |
|---|---|---|---|---|---|---|---|---|---|
| I-347 | 4-Cl | $C_2H_5$ | H | H | H | $COCH_3$ | $COOCH_3$ | 1 | Unmeasurable |
| I-348 | 4-Cl | $C_2H_5$ | H | H | H | $COOCH_3$ | $COOCH_3$ | 1 | 40–42 |
| I-349 | 4-Cl | $C_2H_5$ | H | H | H | $COCH_2OCH_3$ | $COOCH_3$ | 0 | 1.5963 |
| I-350 | 4-Cl | $C_2H_5$ | H | H | H | $COCH_2OCH_3$ | $COOCH_3$ | 1 | 1.5891 |
| I-351 | 4-Cl | $C_2H_5$ | H | H | H | COCH2OCH3 | $COOCH_3$ | 2 | 53–55 |
| I-352 | 4-Cl | $C_2H_5$ | H | H | H | $COOC_2H_5$ | $COOCH_3$ | 0 | 1.5940 |
| I-353 | 4-Cl | $C_2H_5$ | H | H | H | $COOC_2H_5$ | COOCH3 | 2 | 50–52 |
| I-354 | 3-F, 4-Cl | $C_2H_5$ | H | H | H | $COOCH_3$ | H | 0 | 1.6150 |
| I-355 | 4-Cl | $C_2H_5$ | H | H | H | $COCH_3$ | $COOCH_3$ | 2 | Unmeasurable |
| I-356 | 3-F, 4-Cl | $C_2H_5$ | H | H | H | $COOCH_3$ | H | 1 | 54–56 |
| I-357 | 4-F | $C_2H_5$ | H | H | H | $COOCH_3$ | H | 2 | 153–155 |
| I-358 | 3,4-$F_2$ | $C_2H_5$ | H | H | H | $COOCH_3$ | H | 2 | 121–122 |
| I-359 | 4-F | $C_2H_5$ | H | H | H | $COOC_2H_5$ | H | 2 | 134–135 |
| I-360 | 3,4-$F_2$ | $C_2H_5$ | H | H | H | $COOCH_3$ | H | 1 | 1.5923 |
| I-361 | H | $C_2H_5$ | H | H | H | $COOCH_3$ | H | 2 | 149–150 |
| I-362 | 3-F | $C_2H_5$ | H | H | H | $COOCH_3$ | H | 2 | 124–126 |
| I-363 | 3,4,5-$F_3$ | $C_2H_5$ | H | H | H | $COOCH_3$ | H | 2 | 184–186 |
| I-364 | 4-F | $C_2H_5$ | H | H | H | $COOCH_3$ | H | 1 | Unmeasurable |
| I-365 | 4-Cl | $CF_3$ | H | H | H | $CON(CH_3)_2$ | H | 2 | 144–146 |
| I-366 | 4-Cl | $CF_3$ | H | H | H | $COOCH_3$ | $CH_2OC_2H_5$ | 0 | 1.5601 |
| I-367 | 4-Cl | $CF_3$ | H | H | H | $COOCH_3$ | $CH_2OC_2H_5$ | 1 | 1.5628 |
| I-368 | 4-Cl | $CF_3$ | H | H | H | $COOCH_3$ | $CH_3$ | 2 | 1.3615 |
| I-369 | 4-Cl | $CF_3$ | H | H | H | $COOCH_3$ | 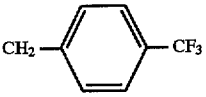 | 2 | 1.5398 |
| I-370 | 2-F, 4-Cl | $CF_3$ | H | H | H | $COOCH_3$ | H | 2 | 165–167 |
| I-371 | 4-Cl | $CF_3$ | H | H | H | $COOCH_3$ | 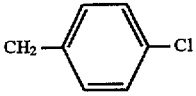 | 2 | 1.5818 |
| I-372 | 4-Cl | $CF_3$ | H | H | 3-F | $COOCH_3$ | H | 2 | 85–87 |

TABLE 15

| Comp. No. | $R^9m$ | $R^1$ | $R^2$ | $R^3$ | $R^4$ | $R^{12}$ | $R^{13}$ | n | m.p. (°C.) or refractive index ($n_D^{30}$) |
|---|---|---|---|---|---|---|---|---|---|
| I-373 | 4-Cl | $CF_3$ | H | H | H | $COOCH_3$ | 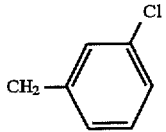 | 2 | 1.5852 |
| I-374 | 4-Cl | $CF_3$ | H | H | H | $COOCH_3$ | 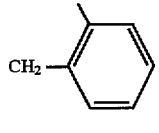 | 2 | 1.5802 |
| I-375 | 4-Cl | $CF_3$ | H | H | H | $COOCH_3$ | 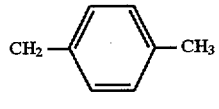 | 2 | 45–46 |
| I-376 | 3-F, 4-Cl | $CF_3$ | H | H | H | $CH_2CF_3$ | H | 2 | 1.5360 |
| I-377 | 3-F, 4-Cl | $CF_3$ | H | H | H | CH2CF3 | $CONH_2$ | 2 | 40–41 |
| I-378 | 3-F, 4-Cl | $CF_3$ | H | H | H | $COOCH_3$ | H | 2 | 129–131 |
| I-379 | 3-F, 4-Cl | $CF_3$ | H | H | H | $COOCH_3$ | H | 0 | 1.5821 |

TABLE 15-continued

| Comp. No. | R⁹m | R¹ | R² | R³ | R⁴ | R¹² | R¹³ | n | m.p. (°C.) or refractive index ($n_D^{30}$) |
|---|---|---|---|---|---|---|---|---|---|
| I-380 | 4-Cl | CF₃ | H | H | 3-F | COOC₂H₅ | H | 1 | 139–140 |
| I-381 | 4-Cl | CF₃ | H | H | H | H | H | 1 | 1.6052 |
| I-382 | 4-Cl | CF₃ | H | H | H | COCH₂C≡CH | H | 2 | 121–122 |
| I-383 | 3,4-Cl₂ | CF₃ | H | H | H | COOCH₃ | H | 2 | 163–165 |
| I-384 | 3-F, 4-Cl | CF₃ | H | H | H | COOC₂H₅ | H | 0 | 1.5720 |
| I-385 | 4-Cl | CF₃ | H | H | H | COCH₂OCH₂CF₃ | H | 0 | 1.5579 |
| I-386 | 4-Cl | CF₃ | H | H | H | COCH₂OCH₂CF₃ | H | 1 | 127–129 |
| I-387 | 3-F, 4-Cl | CF₃ | H | H | H | COOCH₃ | H | 1 | 65–67 |
| I-388 | 4-Cl | CF₃ | H | H | 3-F | COOC₂H₅ | H | 0 | 1.5747 |
| I-389 | 4-Cl | CF₃ | H | H | 3-F | COOCH₃ | H | 0 | Unmeasurable |
| I-390 | 4-Cl | CF₃ | H | H | H | COOC₂H₅ | COOC₂H₅ | 0 | 1.5564 |
| I-391 | 4-Cl | CF₃ | H | H | H | COOC₃H₇ | H | 0 | 1.5793 |
| I-392 | 4-Cl | CF₃ | H | H | H | COOC₄H₉ | H | 0 | 1.5712 |
| I-393 | 3-CH₃, 4-Cl | CF₃ | H | H | H | COOCH₃ | H | 2 | 149–151 |
| I-394 | 4-Cl | CF₃ | CH₃ | H | H | COOC₂H₅ | H | 0 | 1.5703 |
| I-395 | 4-Cl | CF₃ | CH₃ | H | H | COOCH₃ | H | 0 | 1.5770 |
| I-396 | 4-Cl | CF₃ | H | H | H | COC₃H₇-i | H | 0 | 41–42 |
| I-397 | 4-Cl | CF₃ | H | H | H | COOC₂H₄OC₂H₅ | H | 0 | 38–39 |
| I-398 | 4-Cl | CF₃ | H | H | H | COOC₃H₇-i | H | 0 | 1.5930 |

TABLE 16

| Comp. No. | R⁹m | R¹ | R² | R³ | R⁴ | R¹² | R¹³ | n | m.p. (°C.) or refractive index ($n_D^{30}$) |
|---|---|---|---|---|---|---|---|---|---|
| I-399 | 4-Cl | CF₃ | H | H | H | COO—C₆H₅ | H | 0 | 1.5992 |
| I-400 | 3,4-Cl₂ | CF₃ | H | H | H | COOC₂H₅ | H | 0 | 68–70 |
| I-401 | 4-Cl | CF₃ | H | H | H | COOC₃H₇ | H | 2 | 118–120 |
| I-402 | 4-Cl | CF₃ | H | H | H | COCH₂CH₂SCH₃ | H | 0 | 74–76 |
| I-403 | 4-Cl | CF₃ | H | H | H | CO—(2,6-Cl₂-C₆H₃) | H | 0 | 1.6058 |
| I-404 | 4-Cl | CF₃ | H | H | H | CO—(4-t-C₄H₉-C₆H₄) | H | 0 | 141–143 |
| I-405 | 4-Cl | CF₃ | H | H | H | CO—(3-C₆H₅O-C₆H₄) | H | 0 | 1.6289 |
| I-406 | 4-Cl | CF₃ | H | H | H | CO—(2-CF₃-C₆H₄) | H | 0 | 151–153 |

TABLE 16-continued

| Comp. No. | $R^9m$ | $R^1$ | $R^2$ | $R^3$ | $R^4$ | $R^{12}$ | $R^{13}$ | n | m.p. (°C.) or refractive index ($n_D^{30}$) |
|---|---|---|---|---|---|---|---|---|---|
| I-407 | 4-Cl | $CF_3$ | H | H | H | CO-C$_6$H$_4$-CH$_3$ (4-methylbenzoyl) | H | 0 | 136–138 |
| I-408 | 4-Cl | $CF_3$ | H | H | H | CO-C$_6$H$_4$-OCH$_3$ (4-methoxybenzoyl) | H | 0 | 1.6164 |
| I-409 | 4-Cl | $CF_3$ | H | H | H | CO-C$_6$H$_4$-NO$_2$ (4-nitrobenzoyl) | H | 0 | 153–155 |
| I-410 | 4-Cl | $CF_3$ | H | H | H | CO-(2-furyl) | H | 0 | 136–137 |
| I-411 | 4-Cl | $CF_3$ | H | H | H | CO-(1-naphthyl) | H | 0 | 63–64 |
| I-412 | 4-Cl | $CF_3$ | H | H | H | COCH=CHCH$_3$ | H | 0 | 1.6004 |
| I-413 | 4-Cl | $CF_3$ | H | H | H | CO-C$_6$F$_4$ (pentafluorobenzoyl-like, tetrafluoro) | H | 0 | 163–165 |
| I-414 | 4-Cl | $CF_3$ | H | H | H | CO-(2-thienyl) | H | 0 | 125–127 |
| I-415 | 4-F | $CF_3$ | H | H | H | COOCH$_3$ | H | 0 | 1.5732 |

TABLE 17

| Comp. No. | $R^9m$ | $R^1$ | $R^2$ | $R^3$ | $R^4$ | $R^{12}$ | $R^{13}$ | n | m.p. (°C.) or refractive index ($n_D^{30}$) |
|---|---|---|---|---|---|---|---|---|---|
| I-416 | 4-F | $CF_3$ | H | H | H | COOCH$_3$ | H | 1 | 138–139 |
| I-417 | 4-F | $CF_3$ | H | H | H | COOCH$_3$ | H | 2 | 155–157 |
| I-418 | 4-F | $CF_3$ | H | H | H | COCH$_3$ | H | 2 | 117–119 |
| I-419 | 4-phenyl | $CF_3$ | H | H | H | COOC$_2$H$_5$ | H | 2 | 83–85 |
| I-420 | 3,4-F$_2$ | $CF_3$ | H | H | H | COOCH$_3$ | H | 2 | 163–165 |
| I-421 | 4-OCHF$_2$ | $CF_3$ | H | H | H | COOCH$_3$ | H | 2 | 130–131 |

TABLE 17-continued

| Comp. No. | R$^9$m | R$^1$ | R$^2$ | R$^3$ | R$^4$ | R$^{12}$ | R$^{13}$ | n | m.p. (°C.) or refractive index ($n_D^{30}$) |
|---|---|---|---|---|---|---|---|---|---|
| I-422 | 4-O—⟨phenyl⟩ | CF$_3$ | H | H | H | COOC$_2$H$_5$ | H | 2 | 66–68 |
| I-423 | 3,4,5-F$_3$ | CF$_3$ | H | H | H | COOCH$_3$ | H | 2 | 153–154 |
| I-424 | 4-OCF$_3$ | CF$_3$ | H | H | H | COOCH$_3$ | H | 2 | 134–135 |
| I-425 | 4-OCF$_3$ | CF$_3$ | H | H | H | COOC$_2$H$_5$ | H | 2 | 62–64 |
| I-426 | 4-O—⟨phenyl-Cl⟩ | CF$_3$ | H | H | H | COOC$_2$H$_5$ | H | 2 | 59–60 |
| I-427 | 4-OSO$_2$CF$_3$ | CF$_3$ | H | H | H | COOC$_2$H$_5$ | H | 2 | 61–63 |
| I-428 | 4-OCH$_2$CF$_3$ | CF$_3$ | H | H | H | COOCH$_3$ | H | 2 | 163–166 |
| I-429 | 4-SCH$_3$ | CF$_3$ | H | H | H | COOCH$_3$ | H | 2 | 120–122 |
| I-430 | 4-SCHF$_2$ | CF$_3$ | H | H | H | COOCH$_3$ | H | 2 | 139–140 |
| I-431 | 3,5-F$_2$ | CF$_3$ | H | H | H | COOCH$_3$ | H | 2 | 141–142 |
| I-432 | 3-F | CF$_3$ | H | H | H | COOCH$_3$ | H | 2 | 141–143 |
| I-433 | 3-F | CF$_3$ | H | H | H | CONH—⟨phenyl⟩—OCF$_3$ | H | 2 | 108–110 |
| I-434 | 3-F | CF$_3$ | H | H | H | CONH—⟨phenyl⟩—Cl | H | 2 | 172–173 |
| I-435 | 3-Cl, 4-F | CF$_3$ | H | H | H | COOCH$_3$ | H | 2 | 186–188 |
| I-436 | H | CF$_3$ | H | H | H | COOCH$_3$ | H | 0 | 1.5839 |
| I-437 | 4-Br | CF$_3$ | H | H | H | COOCH$_3$ | H | 0 | 1.5940 |
| I-438 | H | CF$_3$ | H | H | H | COOC$_2$H$_5$ | H | 0 | 1.5760 |
| I-439 | 4-Br | CF$_3$ | H | H | H | COOC$_2$H$_5$ | H | 0 | 1.5901 |
| I-440 | H | CF$_3$ | H | H | H | COOCH$_3$ | H | 1 | 135–136 |

TABLE 18

| Comp. No. | R$^9$m | R$^1$ | R$^2$ | R$^3$ | R$^4$ | R$^{12}$ | R$^{13}$ | n | m.p. (°C.) or refractive index ($n_D^{30}$) |
|---|---|---|---|---|---|---|---|---|---|
| I-441 | 4-Br | CF$_3$ | H | H | H | COOCH$_3$ | H | 1 | 169–170 |
| I-442 | 4-CF | CF$_3$ | H | H | H | COOC$_2$H$_5$ | H | 0 | 52–54 |
| I-443 | 3,4-(OCH$_2$O) | CF$_3$ | H | H | H | COOCH$_3$ | | 2 | 182–185 |
| I-444 | H | CF$_3$ | CH$_3$ | H | H | COOC$_2$H$_5$ | H | 0 | 1.5680 |
| I-445 | 4-F | CF$_3$ | H | H | H | COOC$_2$H$_5$ | H | 0 | 1.5610 |
| I-445 | 4-OCH$_3$ | CF$_3$ | H | H | H | COOC$_2$H$_5$ | H | 0 | 1.5812 |
| I-447 | 4-Br | CF$_3$ | CH$_3$ | H | H | COOCH$_3$ | H | 0 | 1.5921 |
| I-448 | 4-Br | CF$_3$ | H | H | H | COOC$_2$H$_5$ | H | 0 | 1.5859 |
| I-449 | 4-I | CF$_3$ | H | H | H | COOCH$_3$ | H | 0 | Unmeasurable |
| I-450 | 4-I | CF$_3$ | H | H | H | COOC$_2$H$_5$ | H | 0 | 1.6060 |
| I-451 | 4-Cl | CHF$_2$ | H | H | H | COOCH$_3$ | CH$_3$ | 0 | 1.6131 |
| I-452 | 4-Cl | CHF$_2$ | H | H | H | COOCH$_3$ | CH$_2$OC$_2$H$_5$ | 0 | 1.5738 |
| I-453 | 4-Cl | CHF$_2$ | H | H | H | COOCH$_3$ | CH$_3$ | 1 | 1.5991 |
| I-454 | 4-Cl | CHF$_2$ | H | H | H | COOCH$_3$ | CH$_2$OC$_2$H$_5$ | 1 | 1.5802 |
| I-455 | 4-Cl | CHF$_2$ | H | H | H | COOCH$_3$ | CH$_2$—⟨phenyl⟩—Cl | 0 | Unmeasurable |

TABLE 18-continued

| Comp. No. | $R^9m$ | $R^1$ | $R^2$ | $R^3$ | $R^4$ | $R^{12}$ | $R^{13}$ | n | m.p. (°C.) or refractive index ($n_D^{30}$) |
|---|---|---|---|---|---|---|---|---|---|
| I-456 | 4-Cl | $CHF_2$ | H | H | H | $COOCH_3$ | $CH_2$-(4-Cl-phenyl) | 1 | Unmeasurable |
| I-457 | 4-Cl | $CHF_2$ | H | H | H | $COOCH_3$ | $CH_2$-(4-$CF_3$-phenyl) | 0 | 1.5719 |
| I-458 | 4-Cl | $CHF_2$ | H | H | H | $COOCH_3$ | $CH_2$-(4-Cl-phenyl) | 2 | Unmeasurable |
| I-459 | 4-Cl | $CHF_2$ | H | H | H | $COOCH_3$ | $CH_2$-(4-$CF_3$-phenyl) | 2 | 1.5500 |
| I-460 | 4-Cl | $CHF_2$ | H | H | H | $COOCH_3$ | $CH_2$-(2-Cl-phenyl) | 0 | 1.5882 |
| I-461 | 4-Cl | $CHF_2$ | H | H | H | $COOCH_3$ | $CH_2$-(2-Cl-phenyl) | 2 | 47–48 |
| I-462 | 4-Cl | $CHF_2$ | $CH_3$ | H | H | $COOCH_3$ | $CH_2$-phenyl | 2 | 1.5818 |

TABLE 19

| Comp. No. | $R^9m$ | $R^1$ | $R^2$ | $R^3$ | $R^4$ | $R^{12}$ | $R^{13}$ | n | m.p. (°C.) or refractive index ($n_D^{30}$) |
|---|---|---|---|---|---|---|---|---|---|
| I-463 | 4-Cl | $CHF_2$ | H | H | H | $COOC_2H_5$ | $CH_2$-(4-Cl-phenyl) | 2 | Unmeasurable |
| I-464 | 4-Cl | $CHF_2$ | H | H | H | $COOCH_3$ | $CH_2$-(3-Cl-phenyl) | 2 | 1.5950 |
| I-465 | 4-Cl | $CHF_2$ | H | H | H | $COOCH_3$ | $CH_2$-(4-$CH_3$-phenyl) | 2 | 56–57 |
| I-466 | 4-Cl | $CHF_2$ | H | H | H | $COOCH_3$ | $CH_3$ | 2 | 1.5825 |
| I-467 | 4-Cl | $CHF_2$ | H | H | H | $COOC_2H_5$ | $CH_3$ | 2 | 1.5659 |
| I-468 | 4-Cl | $CHF_2$ | H | H | H | $COOCH_3$ | $C_2H_5$ | 2 | 1.5775 |

TABLE 19-continued

| Comp. No. | $R^9m$ | $R^1$ | $R^2$ | $R^3$ | $R^4$ | $R^{12}$ | $R^{13}$ | n | m.p. (°C.) or refractive index ($n_D^{30}$) |
|---|---|---|---|---|---|---|---|---|---|
| I-469 | 4-Cl | $CHF_2$ | H | H | H | $COOCH_3$ | $C_4H_9$ | 2 | 1.5682 |
| I-470 | 4-Cl | $CHF_2$ | H | H | H | H | H | 1 | 1.6203 |
| I-471 | 3-F, 4-Cl | $CHF_2$ | H | H | H | $COOCH_3$ | H | 0 | 111–113 |
| I-472 | 4-Cl | $CHF_2$ | H | H | H | $COCH3$ | H | 1 | 135–137 |
| I-473 | 4-Cl | $CHF_2$ | H | H | H | $COOC_2H_5$ | H | 0 | 1.6061 |
| I-474 | 4-Cl | $CHF_2$ | H | H | H | $COCH_2OCH_2CF_3$ | H | 0 | 1.5761 |
| I-475 | 4-Cl | $CHF_2$ | H | H | H | $COCH_2OCH_2CF_3$ | H | 1 | 1.5742 |
| I-476 | 4-Cl | $CHF_2$ | H | H | H | $COOC_2H_5$ | H | 1 | 189–190 |
| I-477 | 4-Cl | $CHF_2$ | H | H | H | CONH-(2,6-diCl-phenyl) | H | 0 | 124–126 |
| I-478 | 4-Cl | $CHF_2$ | H | H | H | CONH-(2,6-diCl-phenyl) | H | 1 | 102–103 |
| I-479 | 4-Cl | $CHF_2$ | H | H | H | CONH-(4-$OCF_3$-phenyl) | H | 0 | 90–92 |
| I-480 | 4-Cl | $CHF_2$ | H | H | H | $COOC_3H_7$ | H | 0 | 1.6019 |
| I-481 | 4-Cl | $CHF_2$ | H | H | H | $COOCH_3$ | $COOC_2H_5$ | 0 | 1.5502 |
| I-482 | 3-F, 4-Cl | $CHF_2$ | H | H | H | $COOC_2H_5$ | H | 0 | 1.5981 |
| I-483 | 3-F, 4-Cl | $CHF_2$ | H | H | H | $COOC_2H_5$ | $COCH_2OCH_3$ | 0 | 1.5688 |
| I-484 | 4-Cl | $CHF_2$ | $CH_3$ | H | H | $COOC_2H_5$ | H | 0 | 1.5912 |

TABLE 20

| Comp. No. | $R^9m$ | $R^1$ | $R^2$ | $R^3$ | $R^4$ | $R^{12}$ | $R^{13}$ | n | m.p. (°C.) or refractive index ($n_D^{30}$) |
|---|---|---|---|---|---|---|---|---|---|
| I-485 | 4-Cl | $CHF_2$ | H | H | H | $COCH_3$ | H | 0 | 109–112 |
| I-486 | 4-Cl | $CHF_2$ | H | H | H | $COC_3H_7$ | H | 0 | 1.6049 |
| I-487 | 4-Cl | $CHF_2$ | H | H | H | $COCH_3$ | H | 2 | 196–198 |
| I-488 | 4-Cl | $CHF_2$ | H | H | H | $COC_3H_7$ | H | 2 | 112–114 |
| I-489 | 4-Cl | $CHF_2$ | H | H | H | $COOC_3H_7$ | H | 2 | 1.5725 |
| I-490 | 4-F | $CHF_2$ | H | H | H | $COOCH_3$ | H | 0 | 1.5947 |
| I-491 | 4-F | $CHF_2$ | H | H | H | $COOCH_3$ | H | 1 | 135–137 |
| I-492 | 4-F | $CHF_2$ | H | H | H | $COOCH_3$ | H | 2 | 148–150 |
| I-493 | 4-F | $CHF_2$ | H | H | H | $COOC_2H_5$ | H | 0 | 1.5870 |
| I-494 | 4-Br | $CHF_2$ | H | H | H | $COOCH_3$ | H | 0 | 1.6139 |
| I-495 | 4-Br | $CHF_2$ | H | H | H | $COOCH_3$ | H | 1 | 88–90 |
| I-496 | 4-Br | $CHF_2$ | H | H | H | $COOC_2H_5$ | H | 0 | 1.6100 |
| I-497 | 3,4-$F_2$ | $CHF_2$ | H | H | H | $COOCH_3$ | H | 0 | 133–134 |
| I-498 | 3,4-$F_2$ | $CHF_2$ | H | H | H | $COOCH_3$ | H | 1 | 127–128 |
| I-499 | 4-$CF_3$ | $CHF_2$ | H | H | H | $COOC_2H_5$ | H | 0 | 1.5662 |
| I-500 | 4-$CF_3$ | $CHF_2$ | H | H | H | $COOC_2H_5$ | H | 1 | 70–72 |
| I-501 | 4-$CF_3$ | $CHF_2$ | H | H | H | $COOCH_3$ | H | 1 | 64–66 |
| I-502 | 4-Cl | $CH_2Cl$ | H | H | H | $COOCH_3$ | $CH_3$ | 2 | 1.6059 |
| I-503 | 4-Cl | $CF_3$ | H | H | H | $COOC_2H_5$ | —S—N(morpholino) | 0 | |

TABLE 20-continued

| Comp. No. | $R^9m$ | $R^1$ | $R^2$ | $R^3$ | $R^4$ | $R^{12}$ | $R^{13}$ | n | m.p. (°C.) or refractive index ($n_D^{30}$) |
|---|---|---|---|---|---|---|---|---|---|
| I-504 | 4-Cl | $CH_2Cl$ | H | H | H | $COOCH_3$ | $CH_2$—C$_6$H$_4$—$CF_3$ | 2 | 1.5631 |
| I-505 | 4-Cl | $CF_3$ | H | H | H | $COCH_3$ | $-SNC_2H_4CO_2C_2H_5$ (with $C_3H_7$-i) | 0 | |
| I-506 | 4-Cl | Cl | H | H | H | $COOC_2H_5$ | H (phenyl) | 2 | 134–135 |
| I-507 | 4-Cl | $CONHC_4H_9$ | H | H | H | $COOCH_3$ | H | 0 | 47–49 |
| I-508 | 4-Cl | $CF_3$ | H | H | H | $COOCH_3$ | $SN(C_4H_9)_2$ | 0 | |

TABLE 21

| Comp. No. | $R^9m$ | $R^1$ | $R^2$ | $R^3$ | $R^4$ | $R^{12}$ | $R^{13}$ | n | m.p. (°C.) or refractive index ($n_D^{30}$) |
|---|---|---|---|---|---|---|---|---|---|
| I-509 | 4-Cl | $CH_2Cl$ | H | H | H | CO—(2-Cl-pyridin-5-yl) | H | 2 | 132–135 |
| I-510 | 4-F | $CH_2Cl$ | H | H | H | $COOCH_3$ | H | 2 | 152–154 |
| I-511 | 4-Cl | $N(CH_3)_2$ | H | H | H | $COOCH_3$ | H | 2 | |
| I-512 | 4-Cl | —N(pyrrolidinyl) | H | H | H | $COCH_3$ | H | 2 | |
| I-513 | 4-Cl | $NHC_2H_5$ | H | H | H | $COOC_2H_5$ | H | 2 | |
| I-514 | 4-Cl | —N=C(S-)(NH-)(4-CH$_3$-thiazoline) | H | H | H | $COOC_2H_5$ | H | 2 | |
| I-515 | 4-Cl | —N(1,2,4-triazol-1-yl) | H | H | H | $COOC_2H_5$ | H | 2 | |
| I-516 | 4-Cl | $C_2H_5$ | H | H | H | $-C(C_2H_5)=NSO_2C_6H_5$ | H | 0 | 1.6408 |
| I-517 | 4-Cl | $C_2H_5$ | H | H | H | $-C(C_2H_5)=NSO_2C_6H_5$ | H | 2 | 48–50 |

TABLE 21-continued

| Comp. No. | R⁹m | R¹ | R² | R³ | R⁴ | R¹² | R¹³ | n | m.p. (°C.) or refractive index ($n_D^{30}$) |
|---|---|---|---|---|---|---|---|---|---|
| I-518 | 4-Cl | $C_2H_5$ | H | H | H | 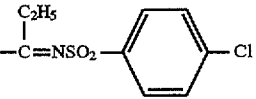 | H | 0 | 1.6424 |
| I-519 | 4-Cl | $C_2H_5$ | H | H | H | 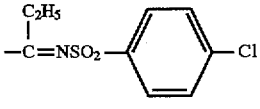 | H | 2 | 75–76 |
| I-520 | 4-Cl | $CF_3$ | $COOC_2H_5$ | $COOC_2H_5$ | H | $COOC_2H_5$ | H | 0 | 1.5345 |
| I-521 | 4-Br | $C_2H_5$ | H | H | H | $COOCH_3$ | H | 2 | 172–174 |
| I-522 | 4-Br | $C_2H_5$ | H | H | H | $COOC_2H_5$ | H | 2 | 96–98 |
| I-523 | 4-Br | $C_2H_5$ | H | H | H | H | H | 2 | 1.6258 |
| I-524 | 4-Br | $C_2H_5$ | H | H | H | $COCH_3$ | H | 2 | 202–204 |
| I-525 | 4-Br | $C_2H_5$ | H | H | H | $COOC_3H_7$ | H | 2 | 105–108 |
| I-526 | 4-Br | $C_2H_5$ | H | H | H | $COOC_2H_4OC_2H_5$ | H | 2 | 65–67 |
| I-527 | 4-Br | $C_2H_5$ | H | H | H | H | H | 0 | 1.6555 |
| I-528 | 4-Br | $C_2H_5$ | H | H | H | $COOCH_3$ | H | 0 | 1.6415 |

TABLE 22

| Comp. No. | R⁹m | R¹ | R² | R³ | R⁴ | R¹² | R¹³ | n | m.p. (°C.) or refractive index ($n_D^{20}$) |
|---|---|---|---|---|---|---|---|---|---|
| I-529 | 4-Br | $C_2H_5$ | H | H | H | $COOC_2H_5$ | H | 0 | 1.6221 |
| I-530 | 4-Br | $C_2H_5$ | H | H | H | $COCH_3$ | H | 0 | 1.6396 |
| I-531 | 4-Br | $C_2H_5$ | H | H | H | $COC_2H_5$ | H | 0 | 1.6463 |
| I-532 | 4-Br | $C_2H_5$ | H | H | H | $COOCH_3$ | H | 1 | 70–72 |
| I-533 | 4-Br | $C_2H_5$ | H | H | H | $COOC_2H_5$ | H | 1 | 62–64 |
| I-534 | 4-Br | $C_2H_5$ | H | H | H | $COC_2H_5$ | H | 1 | 60–62 |
| I-535 | 4-Br | $CHF_2$ | H | H | H | $COCH_3$ | H | 0 | 105–108 |
| I-536 | 4-Br | $CHF_2$ | H | H | H | $COC_2H_5$ | H | 0 | 1.6328 |
| I-537 | 4-Br | $CHF_2$ | H | H | H | $COCH_3$ | H | 1 | 138–139 |
| I-538 | 4-Br | $CHF_2$ | H | H | H | $COC_2H_5$ | H | 1 | 135–137 |
| I-539 | 4-Br | $C_2H_5$ | H | H | H | $COOCH_3$ | $CH_2CN$ | 2 | 74–76 |
| I-540 | 4-Cl | $CF_3$ | H | H | H | $COOC_2H_5$ | $CH_2CN$ | 0 | 1.5689 |

TABLE 23

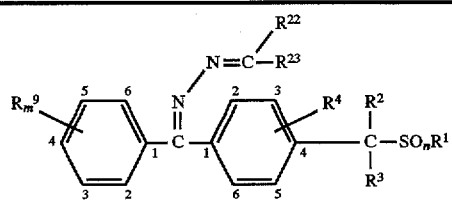

| Comp. No. | R⁹m | R¹ | R² | R³ | R⁴ | R²² | R²³ | n | m.p. (°C.) or refractive index ($n_D^{30}$) |
|---|---|---|---|---|---|---|---|---|---|
| II-1 | 4-Cl | $CH_3$ | H | H | H | H | 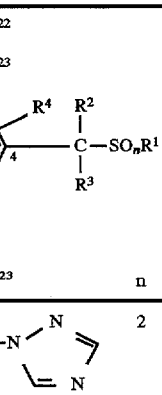 | 2 | |
| II-2 | 4-Cl | $CH_3$ | H | H | H | $N(CH_3)OCH_3$ | | 1 | |

TABLE 23-continued

[Structure diagram with substituents $R^{22}$, $R^{23}$, $R^9_m$, $R^4$, $R^2$, $R^3$, $SO_nR^1$]

| Comp. No. | $R^9$m | $R^1$ | $R^2$ | $R^3$ | $R^4$ | $R^{22}$ | $R^{23}$ | n | m.p. (°C.) or refractive index ($n_D^{30}$) |
|---|---|---|---|---|---|---|---|---|---|
| II-3 | 4-Cl | $CH_3$ | H | H | H | H | $N(CH_3)OCH_3$ | 2 | |
| II-4 | 4-Cl | $CH_3$ | H | H | H | Cl | $N(CH_3)OCH_3$ | 2 | |
| II-5 | 4-Cl | $CF_3$ | H | H | H | $CH_3$ | $NH(CH_2)_3OCH_3$ | 2 | 1.5951 |
| II-6 | 4-Cl | $CF_3$ | H | H | H | $CH_3$ | $N(CH_3)_2$ | 2 | 50–52 |
| II-7 | 4-Cl | $CF_3$ | H | H | H | $CH_3$ | $N(CH_3)OCH_3$ | 2 | |
| II-8 | 4-Cl | $CF_3$ | H | H | H | $CH_3$ | $NHCH_3$ | 2 | 58–60 |
| II-9 | 4-Cl | $CF_3$ | H | H | H | $C_2H_5$ | [1,2,4-triazol-1-yl] | 0 | |
| II-10 | 4-Cl | $CF_3$ | H | H | H | $C_2H_5$ | [1,2,4-triazol-1-yl] | 2 | 1.5978 |
| II-11 | 4-Cl | $CF_3$ | H | H | H | $C_2H_5$ | $N(CH_3)_2$ | 2 | 51–53 |
| II-12 | 4-Cl | $CF_3$ | H | H | H | $C_2H_5$ | $N(CH_3)_2$ | 0 | 1.6238 |
| II-13 | 4-Cl | $CF_3$ | H | H | H | $C_2H_5$ | $NHCH_3$ | 2 | 55–57 |
| II-14 | 4-Cl | $CF_3$ | H | H | H | $C_2H_5$ | Cl | 2 | 108–109 |
| II-15 | 4-Cl | $CF_3$ | H | H | H | $C_4H_9$ | $N(CH_3)_2$ | 2 | 1.6049 |
| II-16 | 4-Cl | $CF_3$ | H | H | H | $C_4H_9$ | $NHCH_3$ | 2 | 35–38 |
| II-17 | 4-Cl | $CH_3$ | H | H | H | $CH_3$ | [1,2,4-triazol-1-yl] | 2 | |
| II-18 | 4-Cl | $CH_3$ | H | H | H | $CH_3$ | $C_4H_9$ | 2 | |
| II-19 | 4-Cl | $CH_3$ | H | H | H | $CH_3$ | $C_4H_9$ | 1 | |
| II-20 | 4-Cl | $CH_3$ | H | H | H | $CH_3$ | $CH_3$ | 2 | |
| II-21 | 4-Cl | $CH_3$ | H | H | H | $CH_3$ | $N(C_4H_9$-t$)OCH_3$ | 2 | |

TABLE 24

| Comp. No. | $R^9$m | $R^1$ | $R^2$ | $R^3$ | $R^4$ | $R^{22}$ | $R^{23}$ | n | m.p. (°C.) or refractive index ($n_D^{30}$) |
|---|---|---|---|---|---|---|---|---|---|
| II-22 | 4-Cl | $CH_3$ | H | H | H | $CH_3$ | $N(CH_3)_2$ | 0 | Unmeasurable |
| II-23 | 4-Cl | $CH_3$ | H | H | H | $CH_3$ | $N(CH_3)_2$ | 1 | 53–55 |
| II-24 | 4-Cl | $CH_3$ | H | H | H | $CH_3$ | $N(CH_3)_2$ | 2 | 156–158 |
| II-25 | 4-Cl | $CH_3$ | H | H | H | $CH_3$ | $N(CH_3)OC_4H_9$-t | 2 | |
| II-26 | 4-Cl | $CH_3$ | H | H | H | $CH_3$ | $N(CH_3)OCH_3$ | 2 | |
| II-27 | 4-Cl | $CH_3$ | H | H | H | $CH_3$ | $NH_2$ | 2 | |
| II-28 | 4-Cl | $CH_3$ | H | H | H | $CH_3$ | $NH_2$ | 1 | |
| II-29 | 4-Cl | $CH_3$ | H | H | H | $C_2H_5$ | [1,2,4-triazol-1-yl] | 0 | 1.6498 |
| II-30 | 4-Cl | $CH_3$ | H | H | H | $C_2H_5$ | [1,2,4-triazol-1-yl] | 1 | Unmeasurable |

TABLE 24-continued

| Comp. No. | R⁹m | R¹ | R² | R³ | R⁴ | R²² | R²³ | n | m.p. (°C.) or refractive index ($n_D^{30}$) |
|---|---|---|---|---|---|---|---|---|---|
| II-31 | 4-Cl | CH₃ | H | H | H | C₄H₉ | N(CH₃)OCH₃ | 2 | |
| II-32 | 4-Cl | CH₃ | H | H | H | C₆H₁₃ | N(CH₃)₂ | 2 | 115–118 |
| II-33 | 4-Cl | CH₃ | H | H | H | C₆H₁₃ | N(CH₃)₂ | 1 | |
| II-34 | 4-Cl | CH₃ | H | H | H | C₆H₁₃ | N(CH₃)₂ | 0 | |
| II-35 | 4-Cl | C₂H₅ | H | H | H | CH₃ | CH₃ | 2 | 1.6163 |
| II-36 | 4-Cl | CH₂Cl | H | H | H | C₂H₅ | Cl | 2 | 1.6108 |
| II-37 | 4-Cl | CHF₂ | CH₃ | CH₃ | H | H | H | 0 | 1.6089 |
| II-38 | 4-Cl | CF₃ | H | H | H | H | N(CH₃)₂ | 2 | 1.6180 |
| II-39 | 4-Cl | CF₃ | H | H | H | CH₃ | N(CH₃)₂ | 0 | 1.6248 |
| II-40 | 4-Cl | CF₃ | H | H | H | CH₃ | N(CH₃)₂ | 1 | Unmeasurable |
| II-41 | 3-F, 4-Cl | CF₃ | H | H | H | CH₃ | N(CH₃)₂ | 2 | 1.6171 |
| II-42 | 4-Cl | CF₃ | H | H | 3-F | CH₃ | N(CH₃)₂ | 2 | 62–68 |
| II-43 | 4-F | CF₃ | H | H | H | CH₃ | N(CH₃)₂ | 2 | 109–111 |
| II-44 | 4-Br | CF₃ | H | H | H | CH₃ | N(CH₃)₂ | 2 | 123–124 |
| II-45 | 4-Br | CF₃ | H | H | H | C₂H₅ | Cl | 2 | 1.6207 |
| II-46 | 4-Br | CF₃ | H | H | H | C₂H₅ | N(CH₃)₂ | 2 | 1.5619 |
| II-47 | 4-F | CF₃ | H | H | H | C₂H₅ | Cl | 2 | 1.5892 |
| II-48 | 4-F | CF₃ | H | H | H | C₂H₅ | N(CH₃)₂ | 2 | 103–104 |

TABLE 25

| Comp. No. | R⁹m | R¹ | R² | R³ | R⁴ | R²² | R²³ | n | m.p. (°C.) or refractive index ($n_D^{20}$) |
|---|---|---|---|---|---|---|---|---|---|
| II-49 | 4-Cl | CHF₂ | H | H | H | CH₃ | N(CH₃)₂ | 2 | 1.6335 |
| II-50 | 4-Cl | CHF₂ | H | H | H | CH₃ | N(CH₃)₂ | 1 | 75–77 |
| II-51 | 4-Cl | C₂H₅ | H | H | H | H | N(CH₃)₂ | 2 | 130–132 |
| II-52 | 4-Cl | CHF₂ | H | H | H | C₂H₅ | N(CH₃)₂ | 0 | 1.6479 |

TABLE 26

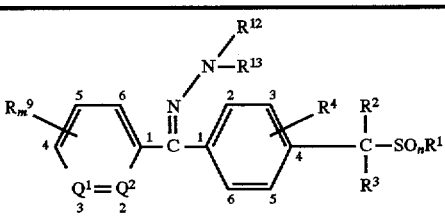

| Comp. No. | R⁹m | R¹ | R² | R³ | R⁴ | R¹² | R¹³ | Q¹ | Q² | n | m.p. (°C.) or refractive index ($n_D^{30}$) |
|---|---|---|---|---|---|---|---|---|---|---|---|
| III-1 | 4-Cl | CH₃ | H | H | H | COOC₂H₅ | H | N | CH | 2 | 149–150 |
| III-2 | 4-Cl | CF₃ | H | H | H | COOC₂H₅ | H | N | CH | 2 | 72–73 |
| III-3 | 4-Cl | CF₃ | H | H | H | H | H | N | CH | 2 | 103–105 |
| III-4 | 4-Cl | CF₃ | H | H | H | COCH₃ | H | N | CH | 2 | 165–167 |
| III-5 | 4-Cl | CF₃ | H | H | H | COOCH₃ | H | N | CH | 2 | 85–87 |
| III-6 | 4-Cl | CH₂Cl | H | H | H | COOC₂H₅ | H | N | CH | 2 | 67–69 |
| III-7 | 4-Cl | CH₂Cl | H | H | H | COOCH₃ | H | N | CH | 2 | 85–87 |
| III-8 | 4-Cl | C₂H₅ | H | H | H | COOCH₃ | H | N | CH | 2 | 176–178 |
| III-9 | 4-Cl | C₂H₅ | H | H | H | COOC₂H₅ | H | N | CH | 2 | Unmeasurable |
| III-10 | 4-Cl | CF₃ | H | H | H | COOCH₃ | H | N | CH | 0 | Unmeasurable |
| III-11 | 4-Cl | CF₃ | H | H | H | COOCH₃ | H | N | CH | 1 | 70–71 |
| III-12 | 4-Cl | CF₃ | H | H | H | COOCH₃ | H | CH | N | 2 | 66–67 |
| III-13 | 4-Cl | CF₃ | H | H | H | COOC₂H₅ | H | CH | N | 2 | 41–42 |

TABLE 27

| Comp. No. | Structure | m.p. (°C.) or refractive index ($n_D^{30}$) |
|---|---|---|
| IV-1 | 6-Cl-pyridin-3-yl / C=N-N=C(CH₃)(Cl) attached to phenyl-CH₂SO₂CF₃ | 1.5979 |
| IV-2 | 6-Cl-pyridin-3-yl / C=N-N=C(CH₃)(N(CH₃)₂) attached to phenyl-CH₂SO₂CF₃ | 1.6065 |
| IV-3 | 5-Cl-pyridin-2-yl / C=N-N=C(CH₃)(N(CH₃)₂) attached to phenyl-CH₂SO₂CF₃ | Unmeasureable |

TABLE 28

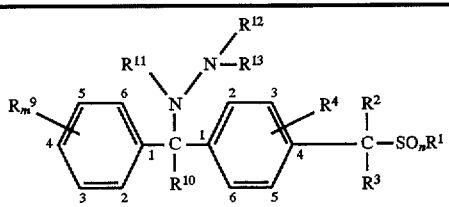

| Comp. No. | R⁹m | R¹ | R² | R³ | R⁴ | R¹⁰ | R¹¹ | R¹² | R¹³ | n | m.p. (°C.) or refractive index ($n_D^{30}$) | Remarks |
|---|---|---|---|---|---|---|---|---|---|---|---|---|
| V-1 | 4-Cl | CH₃ | H | H | H | H | H | COC₂H₅ | H | 2 | 83–85 | |
| V-2 | 4-Cl | C₂H₅ | H | H | H | H | H | H | H | 2 | 1.6079 | |
| V-3 | 4-Cl | C₂H₅ | H | H | H | H | H | COC₂H₅ | H | 2 | 63–64 | |
| V-4 | 4-Cl | C₂H₅ | H | H | H | H | H | COOCH₃ | H | 2 | 60–61 | |
| V-5 | 4-Cl | C₂H₅ | H | H | H | H | H | COOCH₃ | H | 2 | 76–78 | Hydrochloride |
| V-6 | 4-Cl | C₂H₅ | H | H | H | H | COOC₂H₅ | COOC₂H₅ | H | 2 | 66–67 | |
| V-7 | 4-Cl | C₂H₅ | H | H | H | H | COOCH₃ | COOCH3 | H | 2 | 69–71 | |
| V-8 | 4-Cl | CF₃ | H | H | H | H | H | H | H | 2 | 1.5671 | |
| V-9 | 4-Cl | CF₃ | H | H | H | H | H | COC₂H₅ | H | 2 | 49–50 | |
| V-10 | 4-Cl | CF₃ | H | H | H | H | H | COCH₃ | H | 2 | 49–50 | |
| V-11 | 4-Cl | CF₃ | H | H | H | H | H | COOCH₃ | H | 2 | 47–49 | |
| V-12 | 4-Cl | CF₃ | H | H | H | H | H | COOCH₃ | H | 2 | 1.5098 | Methane sulfate |
| V-13 | 4-Cl | CF₃ | H | H | H | H | H | COOCH₃ | H | 2 | 52–54 | Hydrochloride |
| V-14 | 4-Cl | CF₃ | H | H | H | H | H | COOC₂H₅ | H | 2 | Unmeasurable | |
| V-15 | 4-Cl | CF₃ | H | H | H | H | COOCH₃ | COOCH₃ | H | 2 | 55–56 | |
| V-16 | 4-Cl | CHF₂ | H | H | H | H | H | COOCH₃ | H | 2 | 50–53 | |
| V-17 | 4-Cl | CHF₂ | H | H | H | H | H | COOCH₃ | H | 2 | 87–88 | Hydrochloride |
| V-18 | 4-F | CF₃ | H | H | H | H | H | H | H | 2 | 1.5412 | |
| V-19 | 4-F | CF₃ | H | H | H | H | H | COC₂H₅ | H | 2 | 50–52 | |

TABLE 29

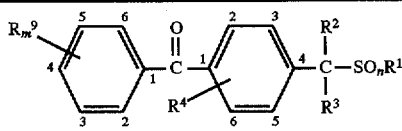

| Comp. No. | R⁹m | R¹ | R² | R³ | R⁴ | n | m.p. (°C.) or refractive index ($n_D^{30}$) |
|---|---|---|---|---|---|---|---|
| VI-1 | 4-Cl | CH₃ | H | H | H | 0 | 59–61 |
| VI-2 | 4-Cl | CH₃ | H | H | H | 1 | 116–118 |
| VI-3 | 4-Cl | CH₃ | H | H | H | 2 | 164–166 |
| VI-4 | 4-Cl | C₂H₅ | H | H | H | 0 | 33–34 |
| VI-5 | 4-Cl | C₂H₅ | H | H | H | 1 | |
| VI-6 | 4-Cl | C₂H₅ | H | H | H | 2 | 117–118 |
| VI-7 | 4-Cl | C₃H₇ | H | H | H | 2 | 128–129 |
| VI-8 | 4-Cl | C₃H₇-i | H | H | H | 2 | 135–137 |
| VI-9 | 4-Cl | C₄H₉ | H | H | H | 2 | 118–119 |
| VI-10 | 4-Cl | CH₂Cl | H | H | H | 2 | 148–150 |
| VI-11 | 4-Cl | C₃H₆Br | H | H | H | 2 | 105–107 |
| VI-12 | 4-Cl | CF₃ | H | H | H | 0 | 63–65 |
| VI-13 | 4-Cl | CF₃ | H | H | H | 1 | 114–115 |
| VI-14 | 4-Cl | CF₃ | H | H | H | 2 | 123–125 |
| VI-15 | 4-Cl | CHF₂ | H | H | H | 0 | 34–35 |
| VI-16 | 4-Cl | CHF₂ | H | H | H | 2 | 154–157 |
| VI-17 | 4-Cl | C₂F₅ | H | H | H | 0 | 52–53 |
| VI-18 | 4-Cl | C₂F₅ | H | H | H | 2 | 94–96 |
| VI-19 | 4-Cl | CH₂CF₃ | H | H | H | 2 | 148–150 |
| VI-20 | 4-Cl | CF₂CHF₂ | H | H | H | 0 | 48–50 |
| VI-21 | 4-Cl | CF₂CHF₂ | H | H | H | 2 | 68–70 |
| VI-22 | 4-Cl | CF₂CHFCF₃ | H | H | H | 0 | Unmeasurable |
| VI-23 | 4-Cl | CH₂CN | H | H | H | 0 | 54–55 |
| VI-24 | 4-Cl | CH₂CN | H | H | H | 2 | 179–181 |

TABLE 30

| Comp. No. | R⁹m | R¹ | R² | R³ | R⁴ | n | m.p. (°C.) or refractive index ($n_D^{30}$) |
|---|---|---|---|---|---|---|---|
| VI-25 | 4-Cl |  | H | H | H | 2 | 113–115 |

TABLE 30-continued

| Comp. No. | R⁹m | R¹ | R² | R³ | R⁴ | n | m.p. (°C.) or refractive index ($n_D^{30}$) |
|---|---|---|---|---|---|---|---|
| VI-26 | 4-Cl | CH₂CH₂OH | H | H | H | 0 | 61–62 |
| VI-27 | 4-CF₃ | CF₃ | H | H | H | 2 | 128–131 |
| VI-28 | 4-Cl | CF₃ | CH₃ | CH₃ | H | 2 | 107–109 |
| VI-29 | 4-Cl | CH₂CH₂OH | H | H | H | 2 | 161–162 |
| VI-30 | 4-F | CH₃ | H | H | H | 0 | 1.6141 |
| VI-31 | 4-F | CH₃ | H | H | H | 2 | 138–139 |
| VI-32 | 4-F | CF₃ | H | H | H | 0 | 43–45 |
| VI-33 | 4-F | C₂H₅ | H | H | H | 0 | 1.6022 |
| VI-34 | 4-F | C₂H₅ | H | H | H | 2 | 97–98 |
| VI-35 | 4-Cl | CN | H | H | H | 0 | 129–131 |
| VI-36 | 4-Cl | —CH₂CH₂CH₂— | | H | H | 2 | Unmeasurable |
| VI-37 | 4-Cl | ![thiazole] | H | H | H | 0 | 80–90 |
| VI-38 | 4-Cl | ![2-chlorophenyl] | H | H | H | 2 | 101–103 |
| VI-39 | 4-Cl | CH₃ | H | H | 3-F | 2 | 132–133 |
| VI-40 | 4-Cl | CF₃ | H | H | H | 2 | 144–145 |
| VI-41 | 4-Cl | CHF₂ | H | H | H | 1 | 124–125 |
| VI-42 | 4-Cl | CONHC₄H₉ | H | H | H | 0 | 115–116 |
| VI-43 | 4-Cl | CF₃ | H | H | 3-F | 0 | 1.5684 |
| VI-44 | 4-Cl | CN | CH₃ | H | H | 0 | 1.6191 |
| VI-45 | 4-Cl | CF₃ | CH₃ | H | H | 0 | 1.5698 |
| VI-46 | 4-Cl | CH₃ | CH₃ | H | H | 2 | 145–147 |
| VI-47 | H | CN | H | H | H | 0 | 138–139 |
| VI-48 | H | CN | CH₃ | H | H | 0 | 1.6189 |
| VI-49 | H | CF₃ | H | H | H | 0 | 43–44 |
| VI-50 | H | CF₃ | CH | H | H | 0 | 1.5581 |

TABLE 31

| Comp. No. | R⁹m | R¹ | R² | R³ | R⁴ | n | m.p. (°C.) or refractive index ($n_D^{30}$) |
|---|---|---|---|---|---|---|---|
| VI-51 | H | CH₃ | CH₃ | H | H | 0 | 143–145 |
| VI-52 | 4-F | CF₃ | H | H | H | 2 | 84–85 |
| VI-53 | 4-F | CH₂Cl | H | H | H | 2 | 110–112 |
| VI-54 | 4-F | CHF₂ | H | H | H | 0 | 1.5572 |
| VI-55 | 4-F | CHF₂ | H | H | H | 2 | 165–167 |
| VI-56 | 4-F | CN | H | H | H | 0 | 116–117 |
| VI-57 | 4-OCHF₂ | CH₃ | H | H | H | 2 | 130–131 |
| VI-58 | 4-OCHF₂ | CF₃ | H | H | H | 2 | 95–96 |
| VI-59 | 4-OCH₂CF₃ | CH₃ | H | H | H | 2 | 110–112 |
| VI-60 | 4-OCH₂CF₃ | CF₃ | H | H | H | 2 | 105–107 |
| VI-61 | 3,4,5-F₃ | CF₃ | H | H | H | 2 | 83–84 |
| VI-62 | 4-OCF₃ | CF₃ | H | H | H | 2 | 116–117 |
| VI-63 | 3-F, 4-Cl | CF₃ | H | H | H | 2 | 79–81 |
| VI-64 | 3-F, 4-Cl | CN | H | H | H | 0 | 93–95 |
| VI-65 | 3-F, 4-Cl | C₂H₅ | H | H | H | 0 | 1.6129 |
| VI-66 | 3-F, 4-Cl | CHF₂ | H | H | H | 0 | 1.5922 |
| VI-67 | 3-F, 4-Cl | CF₃ | H | H | H | 0 | 69–70 |
| VI-68 | 4-Br | CN | H | H | H | 0 | 145–148 |
| VI-69 | 4-Br | CF₃ | H | H | H | 0 | 74–75 |
| VI-70 | 4-Br | CHF₂ | H | H | H | 0 | 63–64 |

TABLE 31-continued

| Comp. No. | $R^9$m | $R^1$ | $R^2$ | $R^3$ | $R^4$ | n | m.p. (°C.) or refractive index ($n_D^{30}$) |
|---|---|---|---|---|---|---|---|
| VI-71 | 4-Br | $CHF_2$ | H | H | H | 1 | 118–119 |
| VI-72 | 4-Br | CN | $CH_3$ | H | H | 0 | 53–54 |
| VI-73 | 4-Br | $CF_3$ | $CH_3$ | H | H | 0 | 39–40 |
| VI-74 | 3,4-$F_2$ | $C_2H_5$ | H | H | H | 1 | 176–178 |
| VI-75 | 4-O—⟨C_6H_4⟩—Cl | $CF_3$ | H | H | H | 2 | 125–126 |
| VI-76 | 4-$OCH_3$ | CN | H | H | H | 0 | 79–81 |
| VI-77 | 4-$OCH_3$ | $CF_3$ | H | H | H | 0 | 57–59 |

TABLE 32

| Comp. No. | $R^9$ m | $R^1$ | $R^2$ | $R^3$ | $R^4$ | n | m.p. (°C.) or refractive index ($n_D^{20}$) |
|---|---|---|---|---|---|---|---|
| VI-78 | 4-I | CN | H | H | H | 0 | 116–118 |
| VI-79 | 4-I | $CF_3$ | H | H | H | 0 | 92–94 |
| VI-80 | 4-Cl | $CF_3$ | $COOC_2H_5$ | $COOC_2H_5$ | H | 0 | 1.5362 |
| VI-81 | 4-Cl | $CCl_3$ | H | H | H | 0 | 103–105 |
| VI-82 | 4-Br | $C_2H_5$ | H | H | H | 2 | 141–142 |
| VI-83 | 4-Br | $CHF_2$ | H | H | H | 2 | 113–115 |
| VI-84 | 4-Br | $C_2H_5$ | H | H | H | 0 | 30 |
| VI-85 | 4-Cl | $CH_3$ | $COOC_2H_5$ | $COOC_2H_5$ | H | 0 | 1.5674 |

TABLE 33

$R_m^9$—(phenyl, positions 5,6,1,2,3; $Q^1=Q^2$ at 3,2)—C(=O)—(phenyl 1,2,3,4,5,6)—C($R^2$)($R^3$)—$SO_nR^1$ with $R^4$

| Comp. No. | $R^9$m | $R^1$ | $R^2$ | $R^3$ | $R^4$ | $Q^1$ | $Q^2$ | n | m.p. (°C.) or refractive index ($n_D^{30}$) |
|---|---|---|---|---|---|---|---|---|---|
| VII-1 | 4-Cl | $CH_3$ | H | H | H | N | CH | 2 | 162–164 |
| VII-2 | 4-Cl | $CF_3$ | H | H | H | N | CH | 2 | 97–99 |
| VII-3 | 4-Cl | $CF_3$ | H | H | H | N | CH | 0 | 1.5820 |
| VII-4 | 4-Cl | $CH_2Cl$ | H | H | H | N | CH | 2 | 94–96 |
| VII-5 | 4-Cl | $C_2H_5$ | H | H | H | N | CH | 2 | 155–156 |
| VII-6 | 4-Cl | CN | H | H | H | N | CH | 0 | 93–94 |
| VII-7 | 4-Cl | $CH_3$ | H | H | H | CH | N | 2 | 153–155 |
| VII-8 | 4-Cl | $CF_3$ | H | H | H | CH | N | 2 | 38–39 |

TABLE 34

$R_m^9$—(phenyl)—CH($R^{28}$)—(phenyl)—C($R^2$)($R^3$)—$SO_nR^1$ with $R^4$

| Comp. No. | $R^9$m | $R^1$ | $R^2$ | $R^3$ | $R^4$ | $R^{28}$ | n | m.p. (°C.) or refractive index ($n_D^{30}$) |
|---|---|---|---|---|---|---|---|---|
| VIII-1 | 4-Cl | $C_2H_5$ | H | H | H | OH | 2 | 1.5950 |
| VIII-2 | 4-Cl | $CF_3$ | H | H | H | OH | 2 | 113–115 |
| VIII-3 | 4-Cl | $CF_3$ | H | H | H | OH | 0 | 1.5601 |
| VIII-4 | 4-Cl | $CHF_2$ | H | H | H | OH | 2 | 85–87 |

TABLE 34-continued

| Comp. No. | $R^9$m | $R^1$ | $R^2$ | $R^3$ | $R^4$ | $R^{28}$ | n | m.p. (°C.) or refractive index ($n_D^{30}$) |
|---|---|---|---|---|---|---|---|---|
| VIII-5 | 4-Cl | $C_2H_5$ | H | H | H | Cl | 2 | 1.6044 |
| VIII-6 | 4-F | $CH_3$ | H | H | H | OH | 2 | 139–140 |
| VIII-7 | 4-F | $CF_3$ | H | H | H | OH | 2 | 99–100 |

TABLE 35

$R_m^9$—(phenyl)—C(=N—N($R^{12}$)($R^{13}$))—(phenyl)—C($R^2$)($R^3$)—$R^{29}$ with $R^4$

| Comp. No. | $R^9$m | $R^2$ | $R^3$ | $R^4$ | $R^{12}$ | $R^{13}$ | $R^{29}$ | m.p. (°C.) or refractive index ($n_D^{30}$) |
|---|---|---|---|---|---|---|---|---|
| IX-1 | 4-Cl | H | H | H | $COOCH_3$ | H | OH | Unmeasurable |
| IX-2 | 4-Cl | H | H | H | $COOC_2H_5$ | H | Cl | 113–115 |
| IX-3 | 4-Cl | H | H | H | $COOCH_3$ | H | SH | 162–165 |

Now, processes for producing the compounds of the present invention will be described.

The compounds of the formula (I) of the present invention can be produced in accordance with the following processes 1 to 5.

Process 1

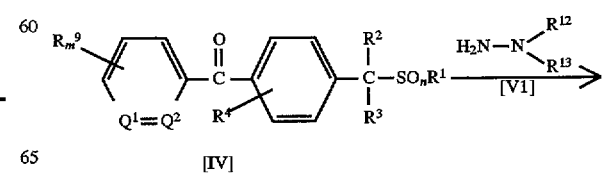

[IV]

-continued

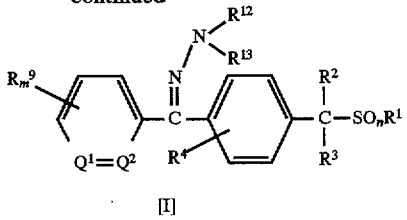

[I]

In the above formulas, $R^1$, $R^2$, $R^3$, $R^4$, $R^9$, $R^{12}$, $R^{13}$, m, n, $Q^1$ and $Q^2$ are as defined above.

In Process 1, a compound of the formula (I) of the present invention wherein A is (A2) can be obtained by reacting 1 mol of a benzophenone of the formula (IV) with from 1.0 to 10.0 mols of a hydrazine of the formula (VI) or its hydrate in the presence of from 0 to 5 l of a solvent, if necessary in the presence of from 0.01 to 1.0 mol of an acid catalyst.

The solvent which can be used, may, for example, be an aromatic hydrocarbon such as benzene, toluene, xylene or chlorobenzene, an aprotic polar solvent such as N,N-dimethylformamide, N,N-dimethylacetamide, N-methyl-2-pyrrolidone, dimethylsulfoxide or sulfolane, an alcohol such as methanol, ethanol, ethylene glycol or glycerol, a halogenated hydrocarbon such as methylene chloride or chloroform, an ester such as ethyl acetate or ethyl propionate, an aliphatic hydrocarbon such as hexane, cyclohexane or heptane, a pyridine such as pyridine or picoline, acetic acid or water, or a solvent mixture thereof.

The acid catalyst may, for example, be a mineral acid such as hydrochloric acid, sulfuric acid or nitric acid, an organic acid such as formic acid, acetic acid, propionic acid, methanesulfonic acid, benzenesulfonic acid or p-toluenesulfonic acid monohydrate, an acid addition salt of an amine such as pyridine hydrochloride or triethylamine hydrochloride, a metal halide such as titanium tetrachloride, zinc chloride, ferrous chloride or ferric chloride, or boron trifluoride etherate.

The reaction temperature is an optional temperature within a range of from −10° C. to the reflux temperature in the reaction system, preferably from room temperature to 150° C. The reaction time varies depending upon the particular compound, but can be set within a range of from 10 minutes to 20 hours.

Process 2

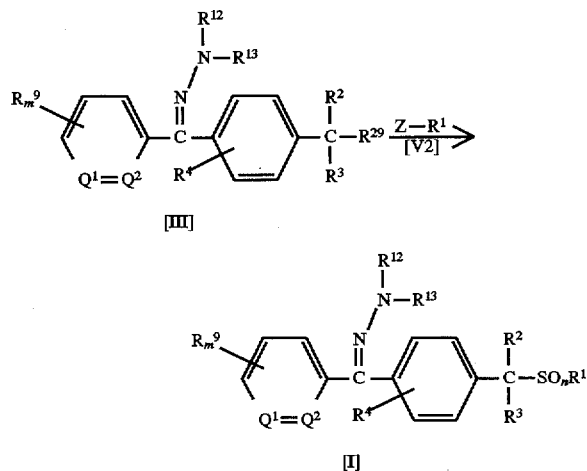

In the above formulas, $R^1$, $R^2$, $R^3$, $R^4$, $R^9$, $R^{12}$, $R^{13}$, m, $Q^1$ and $Q^2$ are as defined above; $R^{29}$ is a halogen atom; Z is a group of the formula $MS(O)_n$; M is an alkali metal; and n is 0 or 2.

In Process 2, a compound of the formula (I) of the present invention wherein A is (A2), can be obtained by reacting 1 mol of benzyl halide of the formula (III) with from 1.0 to 3.0 mol of an alkali metal salt of a sulfur compound of the formula (V2) in the presence of from 0 to 10 l of a solvent.

The solvent which can be used, may, for example, be an ether such as diethyl ether, tetrahydrofuran or dioxane, an aromatic hydrocarbon such as benzene, toluene, xylene or chlorobenzene, an aprotic polar solvent such as N,N-dimethylformamide, N,N-dimethylacetamide, N-methyl-2-pyrrolidone, dimethylsulfoxide or sulfolane, an alcohol such as methanol, ethanol, ethylene glycol or glycerol, a halogenated hydrocarbon such as methylene chloride or chloroform, an ester such as ethyl acetate or ethyl propionate, an aliphatic hydrocarbon such as pentane, hexane, cyclohexane or heptane, a pyridine such as pyridine or picoline or water, or a solvent mixture thereof.

The alkali metal salt of the sulfur compound to be used in this process can be prepared from a sulfur compound wherein Z is $HS(O)_n$ and an alkali metal, an alkali metal hydride or an alkali metal hydroxide.

The reaction temperature is an optional temperature within a range of from −10° C. to the reflux temperature in the reaction system, preferably from room temperature to 100° C. The reaction time varies depending upon the particular compound, but can be set within a range of from 10 minutes to 20 hours.

Process 3

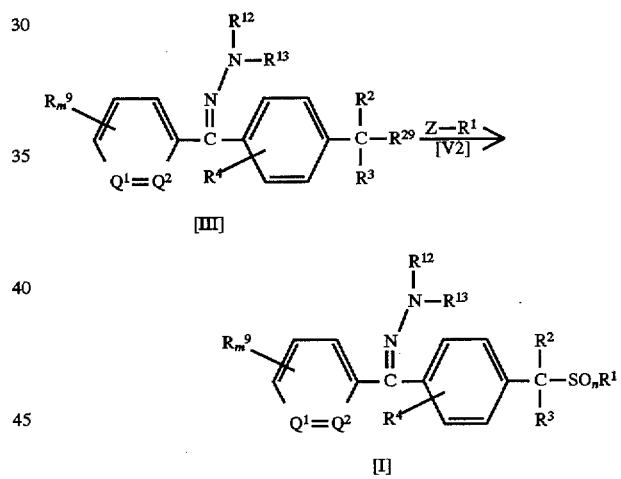

In the above formulas, $R^1$, $R^2$, $R^3$, $R^4$, $R^9$, $R^{12}$, $R^{13}$, m, $Q^1$ and $Q^2$ are as defined above; $R^{29}$ is a mercapto group; and Z is a halogen atom, a $C_{1-4}$ alkylsulfonyloxy group or a benzenesulfonyloxy group (which may be substituted by a methyl group).

In Process 3, a compound of the formula (I) of the present invention wherein A is (A2), can be obtained by reacting 1 mol of a mercapto compound of the formula (III) with from 1.0 to 5.0 mols of the compound of the formula (V2) in from 0 to 5 g of a solvent in the presence of from 1.0 to 3.0 mols of a base.

The solvent which can be used, may, for example, be an ether such as diethyl ether, tetrahydrofuran or dioxane, an aromatic hydrocarbon such as benzene, toluene, xylene or chlorobenzene, an aprotic polar solvent such as N,N-dimethylformamide, N,N-dimethylacetamide, N-methyl-2-pyrrolidone, dimethylsulfoxide or sulfolane, a halogenated hydrocarbon such as methylene chloride or chloroform, a nitrile such as acetonitrile or propionitrile, an ester such as ethyl acetate or ethyl propionate, an aliphatic hydrocarbon such as pentane, hexane, cyclohexane or heptane, a pyridine such as pyridine or picoline or water, or a solvent mixture thereof.

The base may, for example, be an inorganic base e.g. an alkali metal hydroxide such as sodium hydroxide or potassium hydroxide, an alkaline earth metal hydroxide such as calcium hydroxide or magnesium hydroxide, an alkali metal carbonate such as sodium carbonate or potassium carbonate, or an alkali metal bicarbonate such as sodium hydrogen carbonate or potassium hydrogen carbonate, a metal hydride such as sodium hydride or potassium hydride, an alkoxide such as sodium methoxide, sodium ethoxide or potassium tert-butoxide, or an organic base such as triethylamine, N,N-dimethylaniline, pyridine, 4-N,N-dimethylaminopyridine or 1,8-diazabicyclo[5.4.0]-7-undecene.

The reaction temperature is an optional temperature within a range of from −30° C. to the reflux temperature in the reaction system, preferably from 0 to 150° C. The reaction time varies depending upon the particular compound, but can be set within a range of from 10 minutes to 20 hours.

Process 4

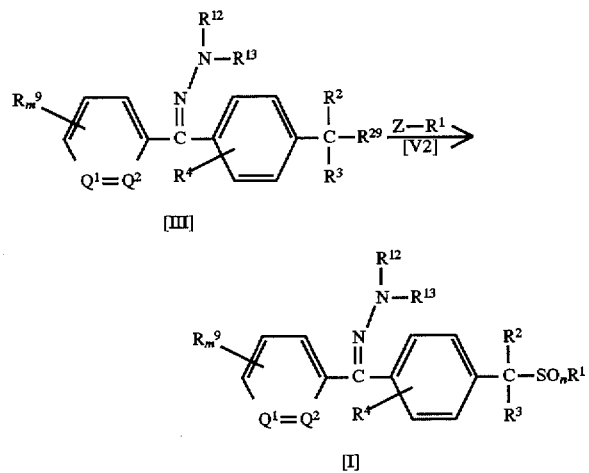

In the above formulas, $R^1$, $R^2$, $R^3$, $R^4$, $R^9$, $R^{12}$, $R^{13}$, m, $Q^1$ and $Q^2$ are as defined above; $R^{29}$ is a hydroxyl group; and Z is a group of the formula $—SSR^1$.

In Process 4, a compound Of the formula (I) of the present invention wherein A is (A2), can be obtained by reacting 1 mol of a benzyl alcohol of the formula (III) with from 1.0 to 3.0 mols of diaminochlorophosphine in from 0.1 to 5 l of a solvent in the presence of from 1.0 to 3.0 mols of a base to obtain a phosphite, and then reacting it with from 1.0 to 5.0 mols of a disulfide of the formula (V2) in the presence of from 0 to 5 l of a solvent.

The solvent and the base which can be used in this process may be the same as used in Process 3.

The reaction temperature is an optional temperature within a range of from −40° C. to the reflux temperature in the reaction system, preferably from −30° to 50° C. The reaction time varies depending upon the particular compound, but can be set within a range of from 10 minutes to 20 hours.

Process 5

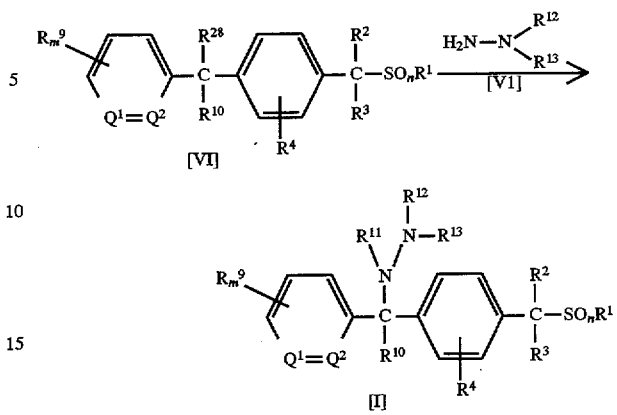

In the above formulas, $R^1$, $R^2$, $R^3$, $R^4$, $R^9$, $R^{10}$, $R^{12}$, $R^{13}$, m, n, $Q^1$ and $Q^2$ are as defined above; $R^{11}$ is a hydrogen atom; and $R^{28}$ is a halogen atom.

In Process 5, a compound of the formula (I) of the present invention wherein A is (A1), can be obtained by reacting 1 mol of a compound of the formula (VI) with from 1.0 to 10.0 mols of a hydrazine of the formula (V1) or its hydrate in the presence of from 0 to 5 l of a solvent, if necessary in the presence of from 1.0 to 3.0 mols of a base.

The solvent which can be used, may, for example, be an ether such as diethyl ether, tetrahydrofuran or dioxane, an aromatic hydrocarbon such as benzene, toluene, xylene or chlorobenzene, an aprotic polar solvent such as N,N-dimethylformamide, N,N-dimethylacetamide, N-methyl-2-pyrrolidone, dimethylsulfoxide or sulfolane, a halogenated hydrocarbon such as methylene chloride or chloroform, a nitrile such as acetonitrile or propionitrile, an ester such as ethyl acetate or ethyl propionate, an aliphatic hydrocarbon such as pentane, hexane, cyclohexane or heptane, a pyridine such as pyridine or picoline, or water, or a solvent mixture thereof.

The base may, for example, be an inorganic base e.g. an alkali metal hydroxide such as sodium hydroxide or potassium hydroxide, an alkaline earth metal hydroxide such as calcium hydroxide or magnesium hydroxide, an alkali metal carbonate such as sodium carbonate or potassium carbonate, an alkali metal bicarbonate such as sodium hydrogen carbonate or potassium hydrogen carbonate, a metal hydride such a sodium hydride or potassium hydride, an alkoxide such as sodium methoxide, sodium ethoxide or potassium tert-butoxide, or an organic base such as triethylamine, N,N-dimethylaniline, pyridine, 4-N,N-dimethylaminopyridine or 1,8-diazabicyclo[5.4.0]-7-undecene.

The reaction temperature is an optional temperature within a range of from −30° C. to the reflux temperature in the reaction system, preferably from 0° to 150° C. The reaction time varies depending upon the particular compound, but can be set within a range of from 10 minutes to 20 hours.

The compound of the formula (I) of the present invention can also be produced by using the compound of the of the formula (I) of the present invention itself as the starting material. Such processes will be shown as Processes 6 to 11. However, such processes are not limited to these illustrated ones.

Process 6

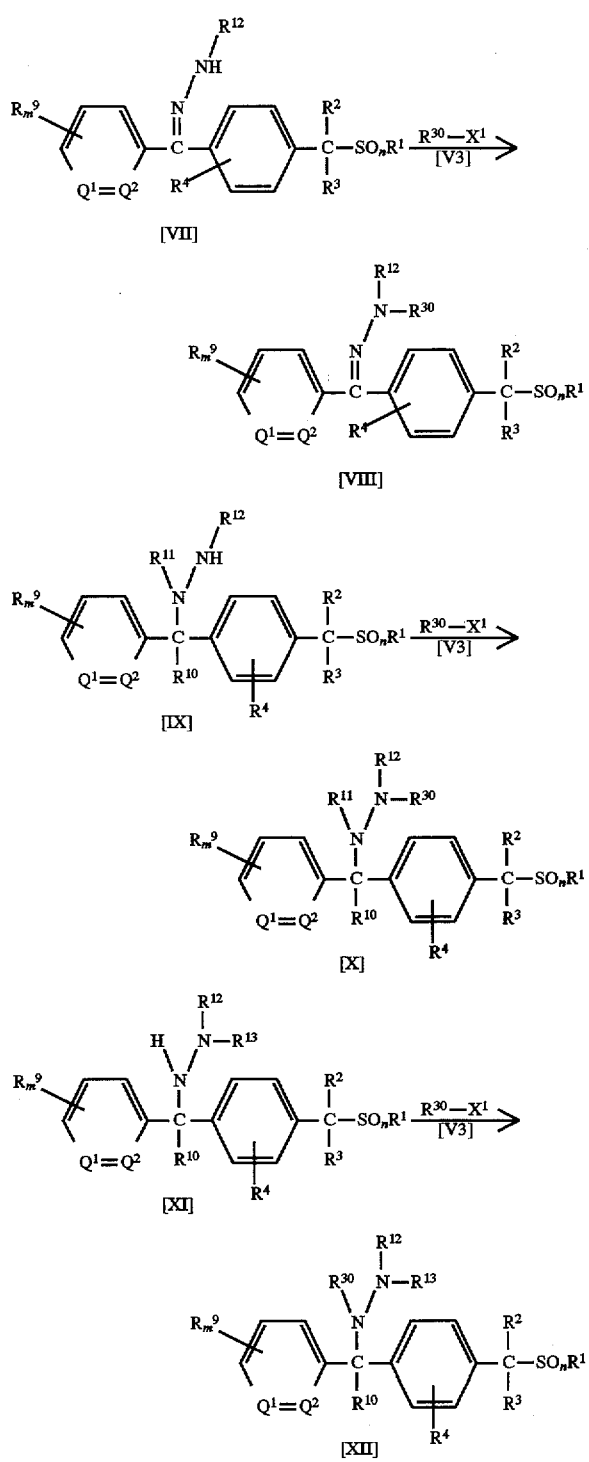

—$C(R^{23})=NR^{25}$; when $R^{30}$ is a group of the formula —$C(R^{21})=CHR^{22}$, $X^1$ is a halogen atom, a hydroxyl group, a $C_{1-4}$ alkoxy group, a $C_{1-4}$ alkylcarbonyloxy group, a mercapto group, a $C_{1-4}$ alkylthio group, a $C_{1-4}$ alkylsulfonyloxy group or a benzenesulfonyl group (which may be substituted by a methyl group), and in other cases, $X^1$ is a halogen atom, a $C_{1-4}$ alkylsulfonyloxy group or a benzenesulfonyloxy group (which may be substituted by a methyl group), or $R^{30}$—$X^1$ may form $R^{17}NCO$ or $ClSO_2NCO$; and $R^1$, $R^2$, $R^3$, $R^4$, $R^9$, $R^{10}$, $R^{11}$, $R^{12}$, $R^{13}$, $R^{14}$, $R^{15}$, $R^{16}$, $R^{17}$, $R^{18}$, $R^{19}$, $R^{20}$, $R^{21}$, $R^{22}$, $R^{23}$, $R^{25}$, $Q^1$, $Q^2$, m and n are as defined above.

Namely, a new compound (VIII), (X) or (XII) of the present invention can be obtained by reacting 1 mol of a compound (VII), (IX) or (XI) of the present invention with from 1.0 to 10.0 mols of a compound of the formula (V3) in the presence of from 0 to 5 l of a solvent, if necessary, in the presence of from 0.1 to 3.0 mols of an acid or a base.

The solvent and the acid catalyst which can be used, may be the same as used in Process 1.

The base may, for example, be an inorganic base e.g. an alkali metal hydroxide such as sodium hydroxide or potassium hydroxide, an alkaline earth metal hydroxide such as calcium hydroxide or magnesium hydroxide, an alkali metal carbonate such as sodium carbonate or potassium carbonate, or an alkali metal bicarbonate such as sodium hydrogen carbonate or a potassium hydrogen carbonate, a metal hydride such as sodium hydride or potassium hydride, an alkoxide such as sodium methoxide, sodium ethoxide or potassium tert-butoxide, or an organic base such as triethylamine, N,N-dimethylaniline, pyridine, 4-N,N-dimethylaminopyridine or 1,8-diazabicyclo[5.4.0]-7-undecene.

The reaction temperature is an optional temperature within a range of from −30° C. to the reflux temperature in the reaction system, preferably from 0° to 150° C. The reaction time varies depending upon the particular compound, but can be set within a range of from 10 minutes to 20 hours.

When chlorosulfonyl isocyanate is reacted with the above compound (VII), (IX) or (XI), the resulting reaction product may be hydrolyzed after isolation or without isolation, to obtain a compound of the present invention wherein $R^{30}$ is $CONH^2$.

Process 7

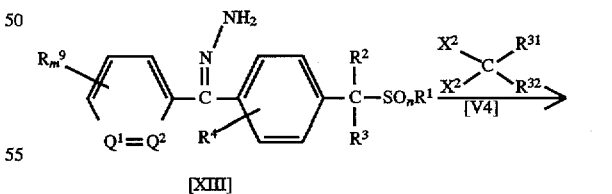

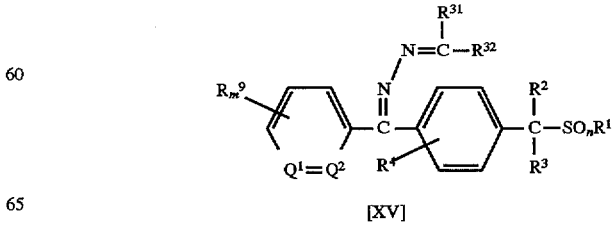

In the above formulas, $R^{30}$ is a cyano group, a $C_{1-6}$ alkyl group, a $C_{1-4}$ haloalkyl group, a $C_{2-10}$ alkoxyalkyl group, a $C_{3-8}$ alkoxyalkoxyalkyl group, a $C_{2-6}$ alkylthioalkyl group, a $C_{2-6}$ alkenyl group, a $C_{2-4}$ alkynyl group, a benzyl group (which may be substituted by a halogen atom, a methyl group or a trifluoromethyl group), a group of the formula —$COR^{14}$, a group of the formula —$COOR^{15}$, a group of the formula —$CON(R^{16})R^{17}$, a group of the formula —SN—$(R^{18})R^{19}$, a group of the formula —$SO_2R^{20}$, a group of the formula —$C(R^{21})=CHR^{22}$ or a group of the formula -continued

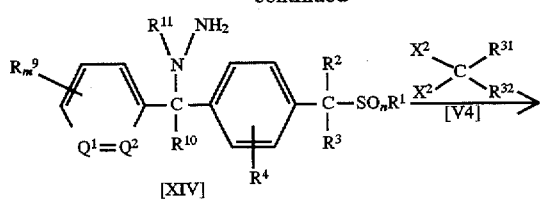

[XIV]

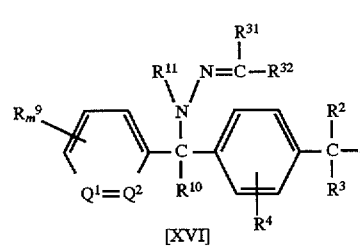

[XVI]

In the above formulas, each of $R^{31}$ and $R^{32}$ which are independent of each other, is a hydrogen atom, a $C_{1-6}$ alkyl group or a group of the formula —$N(R^{25})R^{26}$; $R^1$, $R^2$, $R^3$, $R^4$, $R^9$, $R^{10}$, $R^{11}$, m, n, $Q^1$ and $Q^2$ are as defined above; each of $R^{25}$ and $R^{26}$ which are independent of each other, is a $C_{1-4}$ alkyl group; $X^2$ is a $C_{1-4}$ alkoxy group; or two $X^2$ may form a carbonyl group together with the carbon atom.

Namely, a new compound (XV) or (XVI) of the present invention can be obtained by reacting 1 mol of a compound of the formula (XIII) or (XIV) of the present invention with from 1.0 to 10.0 mols of a compound Of the formula (V4) in the presence of from 0 to 5 l of a solvent, if necessary in the presence of from 0.01 to 1.0 mol of an acid catalyst and a solvent.

This reaction can be conducted under the same conditions as in Process 1.

Process 8

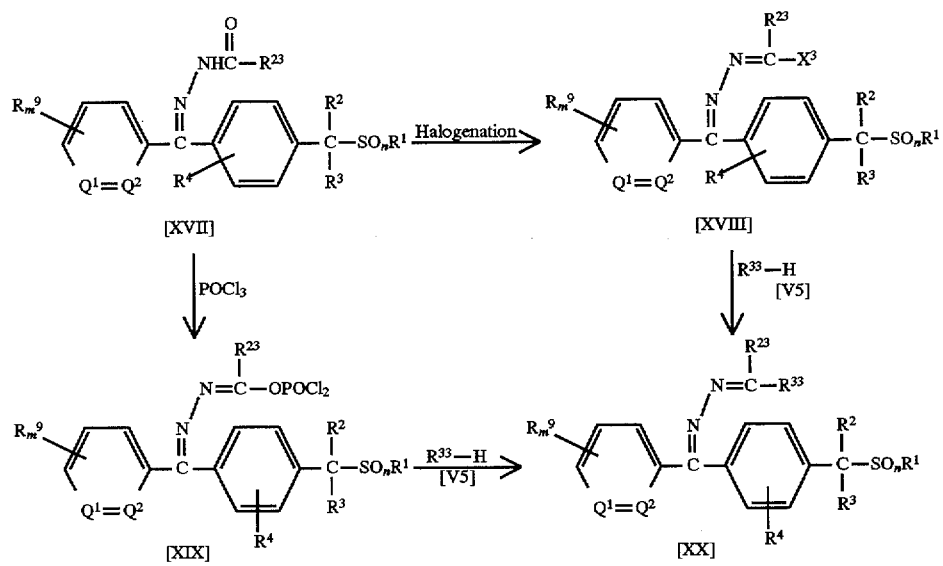

In the above formulas, $R^{33}$ is an azolyl group or a group of the formula —$N(R^{25})R^{26}$; $R^1$, $R^2$, $R^3$, $R^4$, $R^9$, $R^{25}$, $R^{26}$, m, n, $Q^1$ and $Q^2$ are as defined above; $R^{23}$ is a hydrogen atom or a $C_{1-6}$ alkyl group; and $X^3$ is a chlorine atom or a bromine atom.

Namely, a new compound (XVIII) of the present invention can be obtained by reacting 1 mol of a compound of the formula (XVII) of the present invention with from 1.0 to 10.0 mols of a halogenating agent in the presence of from 0 to 5 l of a solvent. Then, from 1.0 to 5.0 mols of a compound of the formula (V5) is reacted in the presence of from 0 to 5 l of a solvent, if necessary in the presence of from 1.0 to 3.0 mols of a base, to obtain a new compound (XX) of the present invention. Further, the compound of the formula (XX) of the present invention can be prepared also by using a compound of the formula (XIX) instead of the compound of the formula (XVIII).

The halogenating agent may, for example, be phosphorus pentachloride, thionyl chloride, a mixture of triphenylphosphine/carbon chloride, or a mixture of triphenylphosphine/bromine.

The solvent which can be used, may, for example, be an ether such as diethyl ether, tetrahydrofuran or dioxane, an aromatic hydrocarbon such as benzene, toluene, xylene or chlorobenzene, a halogenated hydrocarbon such as methylene chloride or chloroform, a nitrile such as acetonitrile or propionitrile, an aliphatic hydrocarbon such as pentane, hexane, cyclohexane or heptane, or a solvent mixture thereof. Further, the halogenating agent may also serve as a solvent.

The reaction temperature is an optional temperature within a range of from 0° C. to the reflux temperature in the system, preferably from 10° to 180° C. The reaction time varies depending upon the particular compound, but can be set within a range of from 10 minutes to 20 hours.

The compound of the formula (XIX) can be obtained by reacting a compound of the formula (XVII) with phosphorus oxychloride. A specific example of such a reaction is disclosed, for example, in Chemical Abstract, vol. 113, 97192b.

The compound of the formula (XX) of the present invention can usually be obtained by reacting a compound of the formula (XVIII) or (XIX) with a compound of the formula (V5) in the presence of a solvent, if necessary in the presence of a base and a catalyst.

The solvent and the base which can be used, may be the same as in Process 6. As the catalyst, a sulfinate such as sodium methanesulfinate or sodium p-toluenesulfinate, or its hydride, may be employed. The reaction temperature is an optional temperature within a range of from 0° C. to the reflux temperature in the reaction system, preferably from 10° to 100° C. The reaction time varies depending upon the particular compound, but can be set within a range of from 10 minutes to 20 hours.

Process 9

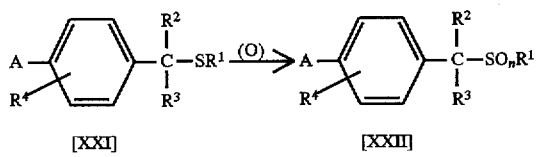

In the above formulas, n is 1 or 2; and A, $R^1$, $R^2$, $R^3$ and $R^4$ are as defined above.

Namely, a new compound of the formula (XXII) of the present invention can be obtained by reacting 1 mol of a compound of the formula (XXI) of the present invention with from 1.0 to 10.0 mols of an oxidizing agent in the presence of from 0 to 5 l of a solvent, if necessary in the presence of from 0.01 to 1.0 mol of a catalyst.

The oxidizing agent may, for example, be hydrogen peroxide, n-chloroperbenzoic acid, sodium periodate, OXONE (tradename for an agent containing potassium hydrogen peroxosulfate, manufactured by E.I. DuPont), N-chlorosuccinimide, N-bromosuccinimide, tert-butyl hypochlorite or sodium hypochlorite. The catalyst may, for example, be a sodium tungstate.

The solvent which can be used here, may, for example, be an ether, an aromatic hydrocarbon, an aprotic polar solvent, an alcohol, a halogenated hydrocarbon or an aliphatic hydrocarbon, as used in Process 1, acetic acid, water or a ketone such as acetone, methyl ethyl ketone or cyclohexanone, or a solvent mixture thereof.

The reaction temperature is an optional temperature within a range of from −20° C. to the reflux temperature in the reaction system, preferably from 10 to 100° C. The reaction time varies depending upon the particular compound, but can be set within a range of from 10 minutes to 20 hours.

Process 10

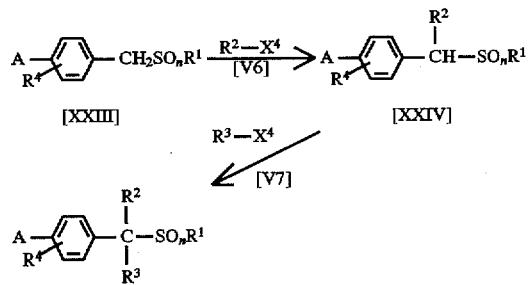

In the above formulas, each of $R^2$ and $R^3$ which are independent of each other, is a $C_{1-4}$ alkyl group or a $C_{1-3}$ haloalkyl group; A, $R^2$, $R^4$ and n are as defined above; and $R^4$ is a halogen atom, a $C_{1-4}$ alkylsulfonyloxy group or a benzenesulfonyloxy group (which may be substituted by a methyl group).

Namely, a compound of the formula (XXIV) can be produced by reacting 1 mol of a compound of the formula (XXIII) with from 1.0 to 5.0 mols of an alkylating agent of the formula (V6) in the presence of from 0 to 5 l of a solvent and from 1.0 to 3.0 mols of a base. Then, this compound (XIV) may be reacted with from 1.0 to 5.0 mols of an alkylating agent of the formula (V7) after isolation or without isolation in the presence of from 0 to 5 l of a solvent and from 1.0 to 3.0 mols of a base, to obtain a compound of the formula (XV).

The base and the solvent which can be used in these reactions, may, for example, be the same as used in Process 6. The reaction temperature is an optional temperature within a range of from −30° C. to the reflux temperature in the reaction system, preferably from 0° to 100° C.

Process 11

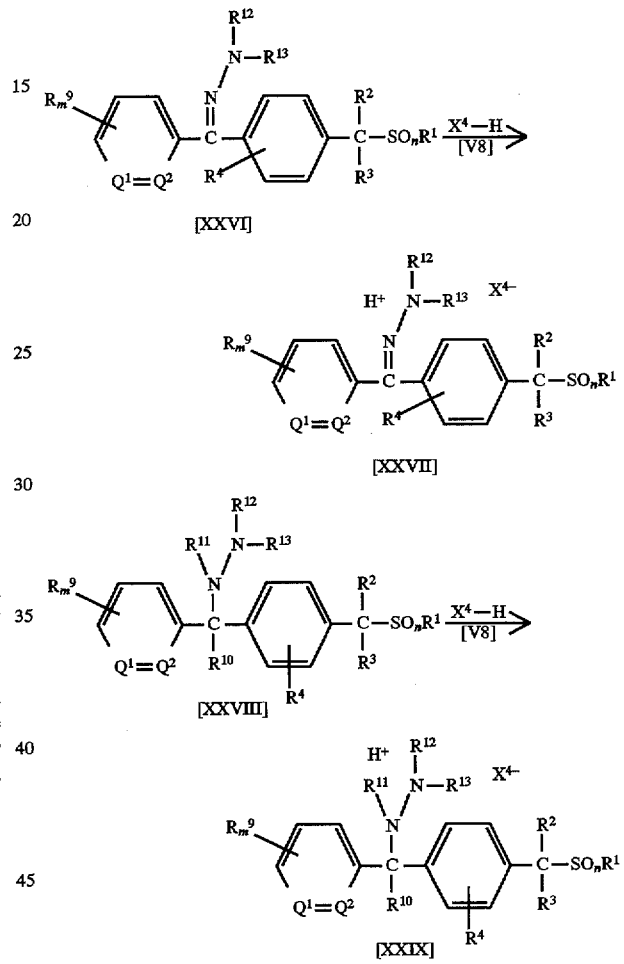

In the above formulas, $X^4$ is a halogen atom, a $C_{1-4}$ alkylsulfonyloxy group or a benzenesulfonyloxy group (which may be substituted by a methyl group); and $R^1$, $R^2$, $R^3$, $R^4$, $R^9$, $R^{10}$, $R^{11}$, $R^{12}$, $R^{13}$, $Q^1$, $Q^2$, m and n are as defined above.

Namely, a salt of the compound (XVII) or (XIX) of the present invention can be obtained by reacting 1 mol of a compound of the formula (XXVI) or (XXVIII) of the present invention with from 1.0 to 3.0 mols of an acid of the formula (V8) in the presence of from 0.1 to 5 l of a solvent.

The solvent which can be used in such a reaction, may, for example, be the same as used in Process 1. The reaction temperature is an optional temperature within a range of from −30° C. to the reflux temperature in the reaction system, preferably from 0° to 100° C.

The novel intermediates of the above formulas (II) and (III) can be produced, for example, in accordance with the following Processes 12 to 20.

Process 12

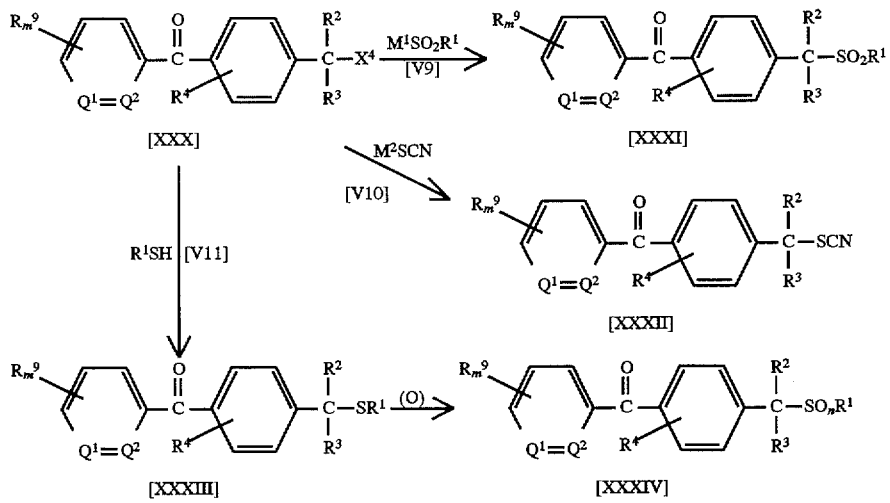

In the above formulas, $R^1$ is a $C_{1-6}$ alkyl group, a $C_{1-4}$ cyanoalkyl group, a $C_{1-4}$ hydroxylalkyl group, a $C_{3-6}$ cycloalkyl group, a $C_{1-6}$ haloalkyl group, a phenyl group (which may be substituted by a halogen atom or a $C_{1-4}$ alkyl group), a benzyl group (which may be substituted by a halogen atom) or a thiazoxyl group; $X^4$ is a halogen atom, a $C_{1-4}$ alkylsulfonyloxy group or a benzenesulfonyloxy group (which may be substituted by a methyl group); $M^1$ is an alkali metal; $M^2$ is an alkali metal or an ammonium ion; $R^2$, $R^3$, $R^4$, m, $Q^1$ and $Q^2$ are as defined above; and n is 1 or 2.

Namely, a benzyl sulfone derivative of the formula (XXXI) can be obtained by reacting 1 mol of a benzyl halide of the formula (XXX) with from 1.0 to 3.0 mols of an alkali metal salt of sulfinic acid of the formula (V9) in the presence of from 0 to 10 l of a solvent.

The solvent which can be used here, may, for example, be an ether, an aromatic hydrocarbon, an aprotic polar solvent, an alcohol, a halogenated hydrocarbon, an aliphatic hydrocarbon or water, or a solvent mixture thereof. The reaction temperature is an optional temperature within a range of from 0° C. to the reflux temperature in the reaction system, preferably from 10° to 100° C.

The salt of sulfinic acid to be used here, may be available as a reagent or can be prepared by a conventional method (e.g. a method disclosed in J. Chem. Soc., vol. 636 (1945), or J. A. Chem. Soc., vol 96, No. 7, p. 2275 (1974)).

Further, under similar reaction conditions, a compound of the formula (XXXII) can be obtained from a compound of the formula (XXX) and a thiocyanate of the formula (V10).

Furthermore, a sulfide of the formula (XXXIII) can be obtained by reacting 1 mol of the compound of the formula (XXX) with from 1.0 to 3.0 mols of a mercaptan of the formula (V11) in the presence of from 0 to 5 l of a solvent in the presence of from 1.0 to 3.0 mol of a base.

The solvent and the base may, for example, be the same as used in Process 6. The reaction temperature is an optional temperature within a range of from $-10°$ C. to the reflux temperature in the reaction system, preferably from 0° to 100° C.

A compound of the formula (XXXIV) of the present invention can be obtained by reacting 1 mol of the compound of the formula (XXXIII) thus obtained with from 1.0 to 10.0 mols of an oxidizing agent in the presence of from 0 to 5 l of a solvent, if necessary in the presence of from 0.01 to 1.0 mol of a catalyst.

The oxidizing agent may, for example, be hydrogen peroxide, m-chloroperbenzoic acid, sodium periodate, OXONE (tradename for an agent containing potassium hydrogen peroxosulfate, manufactured by E.I. DuPont), N-chlorosuccinimide, N-bromosuccinimide, tert-butyl hypochlorite or sodium hypochlorite.

The catalyst may, for example, be sodium tungstate.

The solvent which can be used here, may, for example, be an ether, an aromatic hydrocarbon, an aprotic polar solvent, an alcohol, a halogenated hydrocarbon, an aliphatic hydrocarbon, as used in Process 1, acetic acid, water or a ketone such as acetone, methyl ethyl ketone or cyclohexanone, or a solvent mixture thereof.

The reaction temperature is an optional temperature within a range of from $-20°$ C. to the reflux temperature in the reaction system, preferably from 10° to 100° C.

The benzyl halide of the formula (XXX) to be used as the starting material, is commonly known or can be prepared by a conventional method (e.g. a method disclosed in Org. Synth., vol. 4, p. 921 (1963)) by halogenating the methyl group of the corresponding arylcarbonyltoluene with a halogenating agent (such as chlorine, bromine, N-chlorosuccinimide, N-bromosuccinimide, sulfuryl chloride or sulfuryl bromide).

The arylcarbonyltoluene can be obtained usually by reacting toluene with an aryl carboxylic acid halide in the presence of a Lewis acid such as aluminum chloride.

Process 13

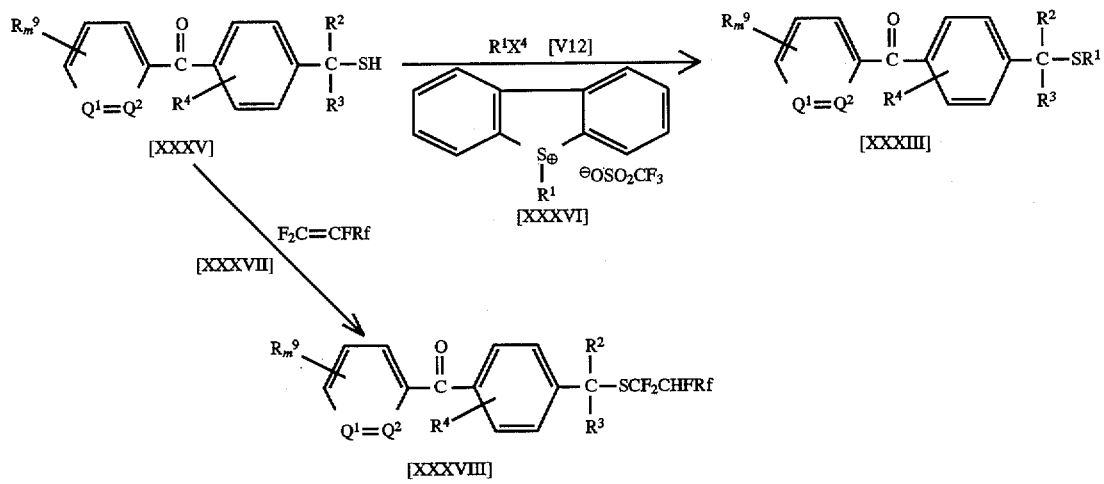

In the above formulas, $R^1$ is a $C_{1-6}$ alkyl group, a $C_{3-6}$ cycloalkyl group, a $C_{1-6}$ haloalkyl group, a $C_{1-4}$ cyanoalkyl group or a $C_{1-4}$ hydroxyalkyl group; $R_f$ is a fluorine atom or a perfluoroalkyl group; $X^4$ is a halogen atom, a $C_{1-4}$ alkylsulfonyloxy group or a benzenesulfonyloxy group (which may be substituted by a methyl group); $R^2$, $R^3$, $R^4$, m, $Q^1$ and $Q^2$ are as defined above; and n is 1 or 2.

The sulfide of the formula (XXXIII) or (XXXVIII) can be obtained by reacting 1 mol of benzyl mercaptan of the formula (XXXV) with from 1.0 to 3.0 mols of an alkylating agent of the formula (V12) and a dibenzothiopheniumtrifluoromethane sulfonate of the formula (XXXVI), or a perfluoroalkene of the formula (XXXVII), in the presence of from 0 to 10 l of a solvent, if necessary in the presence of from 1.0 to 3.0 mols of a base.

The base and the solvent which can be used here, may, for example, be the same as used in Process 6. The reaction temperature is an optional temperature within a range of from 0° C. to the reflux temperature in the reaction system, preferably from 10° to 150° C.

By oxidizing the sulfide of the formula (XIII) or (XVIII) thus obtained by the same oxidizing method as used in Process 12, it is possible to obtain the corresponding sulfoxide or sulfone derivative.

The benzyl mercaptan of the formula (XXXV) to be used as the starting material, is already known or can be prepared in accordance with a conventional method (e.g. a method disclosed in Org. Synth., vol. 3, p. 363 (1955)) or a similar method. Namely, it can be obtained by reacting a benzyl halide of the formula (XXX) as the starting material in Process 12, with sodium sulfide, or reacting it in the presence of thiourea and a base, followed by hydrolysis.

Process 14

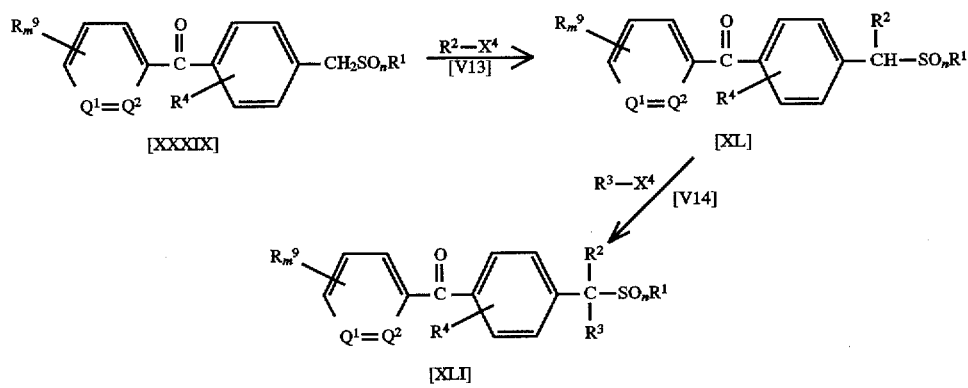

In the above formulas, $R^1$, R4, $R^9$, m, n, $Q^1$ and $Q^2$ are as defined above; each of $R^2$ and $R^3$ is an alkyl group or a haloalkyl group, and $X^4$ is a halogen atom, a $C_{1-4}$ alkylsulfonyloxy group or a benzene sulfonyloxy group (which may be substituted by a methyl group).

Namely, the compound of the formula (XL) or (XVI) can be prepared by reacting 1 mol of a compound of the formula (XXXIX) with from 1.0 to 5.0 mols of an alkylating agent of the formula (V13) or (V14) in the presence of from 0 to 5 l of a solvent and from 1.0 to 3.0 mols of a base. When $X^4$ is present in a side chain of $R^1$, $R^1$ and $R^2$ will form a from 3- to 8-membered ring having one or more hetero atoms, together with the sulfur and carbon atoms to which they are respectively bonded.

The base and the solvent which can be used here, may, for example, be the same as used in Process 6. The reaction temperature is an optional temperature within a range of from 0° C. to the reflux temperature in the reaction system, preferably from 10° to 150° C.

Process 15

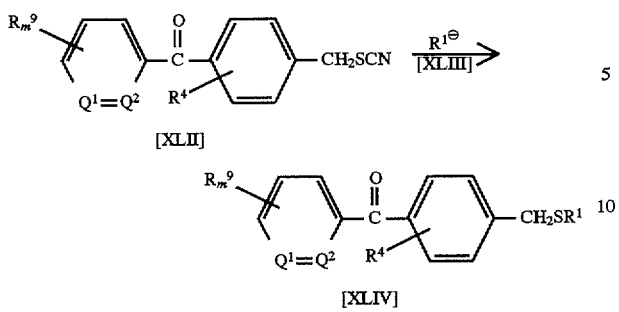

In the above formulas, $R^4$, $R^9$, m, n, $Q^1$ and $Q^2$ are as defined above; and $R^1$ is an alkyl group or a haloalkyl group.

Namely, a compound of the formula (XLIV) can be produced by reacting 1 mol of the compound of the formula (XLII) of the present invention with from 1.0 to 5.0 mols of a carbanion of the formula (XLIII) in the presence of from 0 to 10 l of a solvent. The method for generating the carbanion of the formula (XLIII), may, for example, be 1) a method of contacting from 1.0 to 15.0 mols of a trihalomethane with from 1.0 to 15.0 mols of a base, if necessary in the presence of from 0.01 to 1.0 mol of a phase transfer catalyst such as a tetraalkyl ammonium salt, a benzyltrialkylammonium salt, a tetraalkylphosphonium salt or a crown ether, 2) a method of contacting from 1.0 to 15.0 mols of a (trialkylsilyl)alkyl halide with from 1.0 to 15.0 mols of a fluoride such as potassium fluoride or tetrabutylammonium fluoride, or 3) a method of contacting from 1.0 to 5.0 mols of an alkyl halide or a haloalkyl halide with from 1.0 to 5.0 mols of a metal such as lithium, sodium, copper or zinc, or with an organometallic compound such as lithium diisopropylamide, phenyl lithium or butyl lithium.

The solvent which can be used, may, for example, be an ether, an aromatic hydrocarbon, an aprotic polar solvent, an alcohol, an aliphatic hydrocarbon or water, or a solvent mixture thereof.

The reaction temperature is an optional temperature within a range of from −70° C. to the reflux temperature in the reaction system, preferably from −50° to 50° C.

Process 16

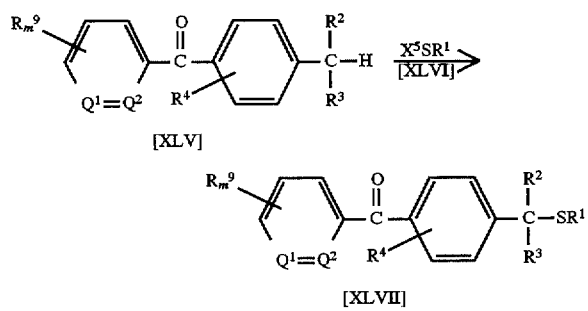

In the above formula, $R^2$, $R^3$, $R^4$, $R^9$, m, n, $Q^1$ and $Q^2$ are as defined above; $X^5$ is a halogen atom, a cyano group or a group of the formula $SR^1$; and $R^1$ is an alkyl group or a haloalkyl group.

Namely, a compound of the formula (XLVII) can be prepared by reacting 1 mol of a compound of the formula (XLV) of the present invention with from 1.0 to 5.0 mols of a compound of the formula (XLVI) in the presence of from 0 to 5 l of a solvent and from 1.0 to 5.0 mols of a base.

The base and the solvent which can be used here, may, for example, be the same as used in Process 6.

The reaction temperature is an optional temperature within a range of from −70° C. to the reflux temperature in the reaction system, preferably from −50° to 50° C.

Process 17

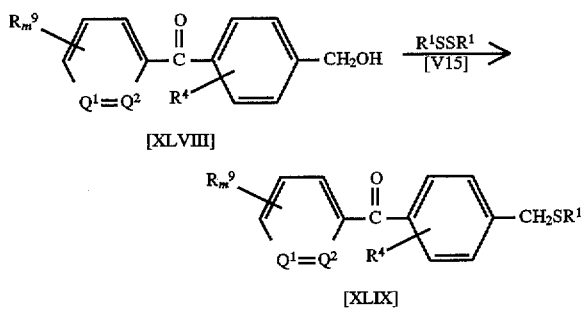

In the above formulas, $R^1$, $R^4$, $R^9$, m, n, $Q^1$ and $Q^2$ are as defined above.

Namely, a compound of the formula (XLIX) of the present invention can be obtained by reacting 1 mol of a benzyl alcohol of the formula (XLVIII) with from 1.0 to 3.0 mol of a dialkylaminochlorophosphine usually in the presence of a solvent and a base, i.e. in the presence of from 0.1 to 5 l of a solvent and from 1.0 to 3.0 mols of a base, to obtain a phosphite, followed by reacting from 1.0 to 5.0 mols of a disulfide of the formula (V15) in the presence of from 0 to 5 l of a solvent.

The solvent which can be used here, may, for example, be an ether such as diethyl ether, tetrahydrofuran or dioxane, an aromatic hydrocarbon such as benzene, toluene, xylene or chlorobenzene, an aprotic polar solvent such as N,N-dimethylformamide, N,N-dimethylacetamide, N-methyl-2-pyrrolidone, dimethylsulfoxide or sulfolane, a halogenated hydrocarbon such as methylene chloride or chloroform, a nitrile such as acetonitrile or propionitrile, an ester such as ethyl acetate or ethyl propionate, an aliphatic hydrocarbon such as pentane, hexane, cyclohexane or heptane, a pyridine such as pyridine or picoline, or a solvent mixture thereof.

The base may, for example, be an inorganic base e.g. an alkali metal hydroxide such as sodium hydroxide or potassium hydroxide, an alkaline earth metal hydroxide such as calcium hydroxide or magnesium hydroxide, an alkali metal carbonate such as sodium carbonate or potassium carbonate, or an alkali metal bicarbonate such as sodium hydrogen carbonate or potassium hydrogen carbonate, a metal hydride such as sodium hydride or potassium hydride, or an organic base such as triethylamine, N,N-dimethylaniline, pyridine, 4-N,N-dimethylaminopyridine or 1,8-diazabicyclo[5.4.0]-7-undecene.

The reaction temperature is an optional temperature within a range of from −40° C. to the reflux temperature in the reaction system, preferably from −30° to 50° C.

The reaction time varies depending upon the particular compound, but can be set within a range of from 10 minutes to 20 hours.

Process 18

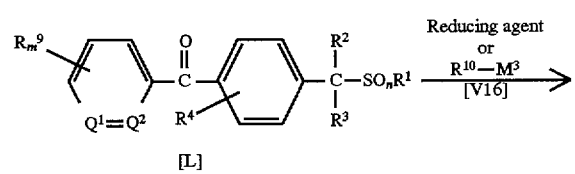

$$[\text{LI}]$$
(structure: Rm9–aryl–C(OH)(R10)–aryl(R4)(R2)–C(R3)(SO_nR^1))

In the above formulas, $R^1$, $R^2$, $R^3$, $R^4$, $R^9$, $R^{10}$, $Q^1$, $Q^2$, $M^3$, m and n are as defined above.

Namely, a compound of the formula (LI) of the present invention can be obtained by reacting a compound of the formula (L) of the present invention with from 1.0 to 50.0 mols of a reducing agent in the presence of from 0 to 5 l of a solvent, if necessary, in the presence of from 0.01 to 1.0 mol of a catalyst, or by reacting it with from 1.0 to 5.0 mols of an alkyl metal compound of the formula (V16).

The reducing agent may, for example, be molecular hydrogen, sodium borohydride, lithium aluminum hydride or aluminum hydride or diisobutylaluminum hydride.

The catalyst may, for example, be platinum, nickel, cobalt or palladium.

The solvent which can be used here, may, for example, be an ether, an aromatic hydrocarbon, an aprotic polar solvent, an alcohol, an aliphatic hydrocarbon, acetic acid or water, or a solvent mixture thereof.

The reaction temperature is an optional temperature within a range of from −20° C. to the reflux temperature in the reaction system, preferably from 10° to 100° C. The reaction time varies depending upon the particular compound, but can be set within a range of from 10 minutes to 20 hours.

Process 19

$$[\text{LI}] \xrightarrow{\text{Halogenating agent}} [\text{LII}]$$

In the above formulas, $R^1$, $R^2$, $R^3$, $R^4$, $R^9$, $R^{10}$, $Q^1$, $Q^2$, m and n are as defined above; and $X^3$ is a chlorine atom or a bromine atom.

A new compound of the formula (LII) of the present invention can be obtained by reacting 1 mol of a compound of the formula (LI) of the present invention with from 1.0 to 10.0 mols of a halogenating agent in the presence of from 0 to 5 l of a solvent.

The halogenating agent may, for example, be hydrogen chloride, hydrogen bromide, phosphorus trichloride, phosphorus tribromide, thionyl chloride, a mixture of triphenylphosphine/carbon tetrachloride or a mixture of triphenylphosphine/bromine.

The solvent which can be used here, may, for example, be an ether such as diethyl ether, tetrahydrofuran or dioxane, an aromatic hydrocarbon such as benzene, toluene, xylene or chlorobenzene, a halogenated hydrocarbon such as methylene chloride or chloroform, a nitrile such as acetonitrile or propionitrile, an aliphatic hydrocarbon such as pentane, hexane, cyclohexane or heptane, or a solvent mixture thereof. Further, the halogenating agent may serve as a solvent.

The reaction temperature is an optional temperature within a range of from 0° C. to the reflux temperature in the reaction system, preferably from 10° to 180° C. The reaction time varies depending upon the particular compound, but can be set within a rang of from 10 minutes to 20 hours.

Process 20

$$[\text{LIII}] \xrightarrow{H_2N-N(R^{12})R^{13} \; [\text{V1}]} [\text{III}]$$

In the above formulas, $R^2$, $R^3$, $R^4$, $R^9$, $R^{12}$, $R^{13}$, $R^{29}$, $Q^1$, $Q^2$ and m are as defined above.

Namely, a compound of the formula (III) of the present invention can be obtained by reacting 1 mol of a benzophenone of the formula (LIII) with from 1.0 to 10.0 mols of a hydrazine of the formula (V1) or its hydrate in the presence of from 0 to 5 l of a solvent, if necessary in the presence of from 0.01 to 1.0 mol of an acid catalyst.

The solvent and the acid catalyst which can be used here, may, for example, be the same as used in Process 1.

The reaction temperature is an optional temperature within a range of from −10° C. to the reflux temperature in the reaction system, preferably from 0° to 100° C.

BEST MODE FOR CARRYING OUT THE INVENTION

Now, the presence invention will be described in further detail with reference to Preparation Examples, Formulation Examples and Test Examples.

PREPARATION EXAMPLE 1

Preparation of 4-Chloro-4'-trifluoromethylsulfonylmethylbenzophenone-N'-ethoxycarbonylhydrazone (Compound No. I-175)

4-chloro-4'-trifluoromethylsulfonylmethylbenzophenone (0.5 g) and ethyl-carbazate (0.4 g) were added to ethanol (40 ml) and acetic acid (5 ml), and the mixture was stirred for 19 hours under reflux. The reaction mixture was concentrated, and the residue was extracted with ethyl acetate. The ethyl acetate layer was washed with water and then dried over anhydrous magnesium sulfate. Ethyl acetate was distilled off under reduced pressure. The residue was purified by silica gel column chromatography (n-hexane:ethyl acetate=4:1) to obtain the desired product (0.6 g, melting point: 148°–150° C., yield: 96%).

$^1$H-NMR data (60 MHz, CDCl$_3$ solvent, δ value) 1.30 (3H, t) 4.23 (2H, q) 4.35, 4.53 (2H, s, s) 7.03–7.80 (9H, m)

PREPARATION EXAMPLE 2

Preparation of 4-Chloro-4'-methylsulfonylmethyl-benzophenone-hydrazone (Compound No. I-2)

4-chloro-4'-methylsulfonylmethylbenzophenone (10.0 g) and hydrazine monohydrate (4.9 g) were added to ethanol (200 ml) and acetic acid (10 ml), and the mixture was stirred for 6 hours under reflux. The reaction mixture was concentrated, and the residue was extracted with ethyl acetate. The ethyl acetate layer was washed with water and then dried over anhydrous magnesium sulfate. Ethyl acetate was distilled off under reduced pressure. The residue was purified by silica gel column chromatography (n-hexane:ethyl acetate=2:1) to obtain the desired product (10.0 g, melting point: 52° to 54° C., yield: 97%)

$^1$H-NMR data (60 MHz, CDCl$_3$ solvent, δ value) 2.73 (3H, s, s) 4.20, 4.30 (2H, s, s) 5.50 (2H, br) 7.05–7.70 (8H, m)

PREPARATION EXAMPLE 3

Preparation of 4-Chloro-4'-methylsulfonylmethylbenzophenone-N'-propionylhydrazone (Compound No. I-15)

4-chloro-4'-methylsulfonylmethylbenzophenone-hydrazone (1.3 g), propionyl chloride (0.4 g) and potassium carbonate (0.7 g) were added to ethyl acetate (150 ml) and water (100 ml), and the mixture was stirred for 2 hours at room temperature. The reaction mixture was subjected to liquid separation, and the ethyl acetate layer was washed with water and then dried over anhydrous magnesium sulfate. Ethyl acetate was distilled off under reduced pressure. The residue was purified by silica gel column chromatography (n-hexane:ethyl acetate=2:1) to obtain the desired product (1.3 g, melting point: 159° to 160° C., yield: 86%).

$^1$H-NMR data (60 MHz, CDCl$_3$ solvent, δ value) 1.23 (3H, t) 2.85–3.00 (5H, m) 4.30 (2H, s) 7.00–8.00 (8H, m) 8.25 (1H, br)

PREPARATION EXAMPLE 4

Preparation of 4-Chloro-4'-trifluoromethylsulfonyl-methylbenzophenone-hydrazone (Compound No. I-136)

4-chloro-4'-trifluoromethylsulfonylmethylbenzophenone (2.5 g), hydrazine monohydrate (4.3 g) and p-toluene sulfonic acid monohydrate (0.2 g) were added to ethanol (30 ml), and the mixture was stirred for 3 hours under reflux. The reaction mixture was concentrated, and the residue was extracted with ethyl acetate. The ethyl acetate layer was washed with water and then dried over anhydrous magnesium sulfate. Ethyl acetate was distilled under reduced pressure. The residue was purified by silica gel column chromatography (n-hexane:ethyl acetate=2:1) to obtain the desired product (2.2 g, n$_D^{20}$=1.5871, yield: 85%)

$^1$H-NMR data (60 MHz, CDCl$_3$ solvent, δ value) 4.43, 4.53 (3H, s, s) 5.47, 5.53 (2H, s, s) 7.07–7.60 (8H, m)

PREPARATION EXAMPLE 5

Preparation of 4-Chloro-4'-trifluoromethylsulfonyl-methylbenzophenone-N'-propionylhydrazone (Compound No. I-149)

4-chloro-4'-trifluoromethylsulfonylmethylbenzophenone-hydrazone (0.9 g), propionyl chloride (0.22 g) and potassium carbonate (0.4 g) were added to a solvent comprising ethyl acetate (100 ml) and water (100 ml), and the mixture was stirred for 16 hours at room temperature. The reaction mixture was subjected to liquid separation, and the ethyl acetate layer was washed with water and then dried over anhydrous magnesium sulfate. Ethyl acetate was distilled off under reduced pressure. The residual solid was washed with n-hexane to obtain the desired product (0.75 g, melting point: 130° to 132° C., yield: 75%).

$^1$H-NMR data (60 MHz, CDCl$_3$ solvent, δ value) 1.20 (3H, t) 2.60–3.00 (2H, m) 4.47 (2H, d) 7.03–7.63 (8H, m) 8.22 (1H, d)

PREPARATION EXAMPLE 6

Preparation of 4-Chloro-4'-trifluoromethylsulfonyl-methylbenzophenone'-(1-chloropropylidene) hydrazone (Compound No. II-14)

4-chloro-4'-trifluoromethylsulfonylmethyl-benzophenone-propionylhydrazone (1.7 g), triphenylphosphine (1.5 g) and carbon tetrachloride (1.2 g) were added to acetonitrile (80 ml), and the mixture was stirred for 10 minuted under reflux. The reaction mixture was concentrated, and the residue was purified by silica gel column chromatography (n-hexane:ethyl acetate=10:1) to obtain the desired product (1.7 g, melting point: 108°–109° C., yield: 97%).

$^1$H-NMR data (60 MHz, CDCl$_3$ solvent, δ value) 1.05, 1.10 (3H, t, t) 2.50, 2.55 (2H, q, q) 4.47 (2H, s) 7.00–7.85 (8H, m)

PREPARATION EXAMPLE 7

Preparation of 4-Chloro-4'-trifluoromethylsulfonyl-methylbenzophenone'-[1-(1-H-1,2,4-triazole-1-yl) propylidene]hydrazone (Compound No. II-10)

4-chloro-4'-trifluoromethylsulfonyl-methylbenzophenone'-(1-chloropropylidene)hydrazone (1.0 g), 1-H-1,2,4-triazole (0.2 g), potassium carbonate (0.4 g) and sodium p-toluene sulfonate (0.3 g) were added to N,N-dimethylformamide (70 ml), and the mixture was stirred for 7 hours at a temperature of from 95° to 100° C. The reaction mixture was cooled to room temperature, and water was added thereto. The mixture was extracted with ethyl acetate. The ethyl acetate layer was washed with water and then dried over anhydrous magnesium sulfate. Ethyl acetate was distilled under reduced pressure. The residue was purified by silica gel column chromatography (n-hexane:ethyl acetate=6:1) to obtain the desired product (0.7 g, n$_D^{20}$=1.5978 yield: 66%)

$^1$H-NMR data (60 MHz, CDCl$_3$ solvent, δ value)

1.28 (3H, t)

3.28 (2H, q)

4.52 (2H, s) 7.05–7.86 (8H, m) 7.95 (1H, s) 8.40, 8.52 (1H, s, s)

PREPARATION EXAMPLE 8

Preparation of 4-Chloro-4'-trifluoromethylsulfonyl-methylbenzophenone'-[1-(N-methylamino) ethylidene]hydrazone (Compound No. II-8)

4-chloro-4'-trifluoromethylsulfonylmethyl-benzophenone'-(1-chloroethylidene)hydrazone (0.7 g) and a 40% methylamine aqueous solution (0.3 g). were added to xylene (50 ml), and the mixture was stirred for one hour under reflux. The reaction mixture was concentrated, and the residue was extracted with ethyl acetate. The ethyl acetate layer was washed with water and then dried over anhydrous magnesium sulfate. Ethyl acetate was distilled off under reduced pressure. The residue was purified by silica gel column chromatography (n-hexane:ethyl acetate=1:1) to obtain the desired product (0.6 g, melting point: 58° to 60° C., yield: 87%).

$^1$H-NMR data (60 MHz, CDCl$_3$ solvent, δ value) 2.00, 2.20 (3H, s, s) 2.67, 2.94 (3H, d, d) 4.46 (2H, s) 6.30 (1H, br) 6.95–7.78 (8H, m)

PREPARATION EXAMPLE 9

Preparation of 4-Chloro-4'-ethylsulfonylmethylbenzophenone-N'-isopropylidenehydrazone (Compound No. II-35)

4-chloro-4'-ethylsulfonylmethylbenzophenone hydrazone (0.7 g) was added to acetone (30 ml), and the mixture was stirred for 30 minutes under reflux. The reaction mixture was concentrated to obtain the desired product (0.7 g, $n_D^{20}$= 1.6163 yield: 88%).

$^1$H-NMR data (60 MHz, CDCl$_3$ solvent, δ value) 1.34 (3H, t) 2.00 (6H, s) 2.90 (2H, q) 4.20 (2H, s) 7.00–7.67 (8H, m)

PREPARATION EXAMPLE 10

Preparation of 4-Chloro-4'-methylthiomethylbenzophenone -N'-[1-(N,N-dimethylamino)ethylidene]hydrazone (Compound No. II-22)

4-chloro-4'-methylthiomethylbenzophenone-hydrazone (2.0 g) and methylacetamide-dimethylacetal (1.4 g) were added to ethanol (100 ml), and the mixture was stirred for 6 hours under reflux. The reaction mixture was concentrated and extracted with ethyl acetate. The ethyl acetate layer was washed with water and then dried over anhydrous magnesium sulfate. Ethyl acetate was distilled off under reduced pressure. The residue was purified by silica gel chromatography (n-hexane:ethyl acetate=6:1) to obtain the desired product as a slightly yellow transparent viscous liquid (2.0 g, yield: 81%).

$^1$H-NMR data (60 MHz, CDCl$_3$ solvent, δ value) 2.00 (3H, s) 2.35 (3H, s) 2.88 (6H, s) 3.66, 3.70 (2H, s, s) 7.03–7.75 (8H, m)

PREPARATION EXAMPLE 11

Preparation of 4-Chloro-4'-methylsulfonylmethylbenzophenone-semicarbazone (Compound No. I-42)

4-chloro-4'-methylsulfonylmethylbenzophenone-hydrazone (1.3 g) and chlorosulfonyl isocyanate (0.63 g) were added to ethyl acetate (100 ml), and the mixture was stirred for one hour at room temperature. Then, water (100 ml) was added, and the mixture was further stirred for 16 hours at room temperature. The reaction mixture was subjected to liquid separation, and the ethyl acetate layer was washed with water and then dried over anhydrous magnesium sulfate. Ethyl acetate was distilled off under reduced pressure. The residual solid was washed with a solvent mixture of ethyl acetate:n-hexane=4:1, to obtain the desired product (1.2 g, melting point: 189° to 191° C., yield: 80%).

$^1$H-NMR data (60 MHz, CDCl$_3$ solvent, δ value) 2.87, 2.97 (3H, s, s) 4.34, 4.50 (5H, m) 7.10–7.70 (8H, m)

PREPARATION EXAMPLE 12

Preparation of 4-Chloro-4'-methylthiomethylbenzophenone-N'-ethoxycarbonyl-N'-methylhydrazone (Compound No. I-47)

4-chloro-4'-methylthiomethylbenzophenone-N'-ethoxycarbonylhydrazone (4.3 g) was dissolved in N,N-dimethylformamide (100 ml). To this solution, 60% sodium hydride (0.6 g) was added, and the mixture was stirred for 30 minutes at room temperature. Then, methyl iodide (2.5 g) was added thereto, followed by stirring for 16 hours at room temperature. Water was added to the reaction mixture, and the mixture was extracted with ethyl acetate. The ethyl acetate layer was washed with water and then dried over anhydrous magnesium sulfate. Ethyl acetate was distilled off under reduced pressure. The residue was purified by silica gel column chromatography (n-hexane:ethyl acetate=5:1) to obtain the desired product (4.3 g, $n_D^{20}$:1.6042, yield: 89%).

$^1$H-NMR data (60 MHz, CDCl$_3$ solvent, δ value) 1.17 (3H, t) 2.00 (3H, s) 2.79, 3.00 (3H, s, s) 3.63, 3.67 (2H, s, s) 4.04 (2H, q) 7.07–7.57 (8H, m)

PREPARATION EXAMPLE 13

Preparation of 4-Chloro-4'-trifluoromethylsulfonylmethylbenzophenone-4-butylsemicarbazone (Compound No. I-171)

4-chloro-4'-trifluoromethylsulfonylmethylbenzophenonehydrazone (1.2 g), triethylamine (0.5 g) and butyl isocyanate (0.6 g) were added to tetrahydrofuran (30 ml), and the mixture was stirred for 16 hours at room temperature. The reaction mixture was concentrated, and the residue was extracted with ethyl acetate. The ethyl acetate layer was washed with 2N hydrochloric acid and water and then dried over anhydrous magnesium sulfate. Ethyl acetate was distilled off under reduced pressure. The residue was purified by silica gel chromatography (n-hexane:ethyl acetate=4:1) to obtain the desired product (0.6 g, melting point: 169° to 181° C., yield: 40%).

$^1$H-NMR data (60 MHz, CDCl$_3$ solvent, δ value) 0.75–1.65 (7H, m) 3.15–3.50 (2H, m) 4.50 (2H, s) 6.20 (1H, br) 6.90–7.70 (9H, m)

PREPARATION EXAMPLE 14

Preparation of 4-Chloro-4'-trifluoromethylsulfonylmethylbenzophenone-N'-methylsulfonyliminomethylhydrazone (Compound No. I-137)

4-chloro-4'-trifluoromethylsulfonylmethyl-benzophenonehydrazone (1.2 g) triethylamine (1.6 g) and N-methylsulfonylformimide acid ethyl (1.2 g) were added to dioxane (30 ml), and the mixture was stirred for 5 hours under reflux. The reaction mixture was concentrated, and the residue was purified by silica gel column chromatography (n-hexane:ethyl acetate=1:1) to obtain the desired product (0.8 g, melting point: 63° to 65° C., yield: 52%).

$^1$H-NMR data (60 MHz, CDCl$_3$ solvent, δ value) 2.95, 3.05 (3H, s, s) 4.45, 4.60 (2H, s, s) 4.95 (1H, br) 7.10–7.80 (8H, m) 8.80 (1H, br)

PREPARATION EXAMPLE 15

Preparation of 4-Chloro-4'-trifluoromethylsulfonylmethylbenzophenone-N'-methylsulfonylhydrazone (Compound No. I-182)

4-chloro-4'-trifluoromethylsulfonylmethylbenzophenonehydrazone (1.2 g) and triethylamine (0.4 g) were dissolved in ethyl acetate (30 ml). To this solution, methane sulfonyl chloride (0.4 g) was dropwise added at room temperature, and the mixture was stirred for one hour. The reaction mixture was washed with 2N hydrochloric acid and water and then and dried over anhydrous magnesium sulfate. Ethyl acetate was distilled off under reduced pressure. The residue was purified by silica gel column chromatography (n-hexane:ethyl acetate=4:1) to obtain the desired product (0.5 g, melting point: 64° to 65° C., yield: 36%).

$^1$H-NMR data (60 MHz, CDCl$_3$ solvent, δ value) 3.50 (3H, s) 4.50 (2H, d) 7.10–7.70 (9H, m)

PREPARATION EXAMPLE 16

Preparation of 4-Chloro-4'-methylsulfinylmethylbenzophenone-N'-propionylhydrazone (Compound No. I-14)

4-chloro-4'-methylthiomethylbenzophenone-N'-propionylhydrazone (0.8 g) and sodium periodide (0.5 g) were added to methanol (50 ml) and water (7 ml), and the mixture was stirred for 16 hours at room temperature. The reaction mixture was concentrated, and the residue was extracted with ethyl acetate. The ethyl acetate layer was washed with water and dried over anhydrous magnesium sulfate. Ethyl acetate was distilled off under reduced pressure. The residue was purified by silica gel column chromatography (n-hexane:ethyl acetate=10:1) to obtain the desired product (0.7 g, melting point: 153° to 156° C., yield: 84%).

$^1$H-NMR data (60 MHz, CDCl$_3$ solvent, δ value) 1.21 (3H, t) 2.43, 2.56 (3H, s, s) 2.85 (2H, q) 3.93, 4.00 (2H, s, s) 6.96–7.70 (8H, m) 8.23 (1H, br)

PREPARATION EXAMPLE 17

Preparation of 4-Chloro-4'-(2-methylsulfonyl-2-propyl) benzophenone-N'-hexanolyl-N'-methylhydrazone (Compound No. I-128)

4-chloro-4'-methylsulfonylmethylbenzophenone-N'-hexanolylhydrazone (1.4 g), methyl iodide (5.6 g) and 60% sodium hydride (0.15 g) were added to N,N-dimethylformamide (80 ml), and the mixture was stirred for 16 hours at room temperature. To the reaction mixture, water was added, and the mixture was extracted with ethyl acetate. The ethyl acetate layer was washed with water and then dried over anhydrous magnesium sulfate. Ethyl acetate was distilled off under reduced pressure. The residue was purified by silica gel chromatography (n-hexane:ethyl acetate= 2:1) to obtain the desired product (0.8 g, melting point: 94° to 96° C., yield: 53%).

$^1$H-NMR data (60 MHz, CDCl$_3$ solvent, δ value) 0.90 (3H, m) 1.10–1.93 (6H, m) 1.87 (6H, s) 2.16–2.67 (2H, m) 2.57, 2.76 (3H, s) 3.09 (3H, s) 7.05–7.73 (8H, m)

PREPARATION EXAMPLE 18

Preparation of 4-Chloro-4'-trifluoromethylsulfonylmethylbenzhydrylhydrazine (Compound No. V-8)

Hydrazine monohydrate (50 ml) and 4-chloro-4'-trifluoromethylfulfonylmethylbenzhydryl chloride were added to toluene (80 ml), and the mixture was gradually heated with stirring. The mixture was stirred at 80° C. for 2 hours, then left to cool and poured into water. 250 ml of ethyl acetate was added thereto for extraction, and the extract was washed with water and dried over anhydrous magnesium sulfate. Then, the solvent was distilled off under reduced pressure to obtain the product as a slightly yellow viscous substance (2.9 g, n$_D^{20}$: 1.5671, yield: 82.4%).

$^1$H-NMR data (60 MHz, CDCl$_3$ solvent, δ value) 3.83 (2H, br) 4.38 (2H, s) 4.83 (1H, s) 6.96–7.50 (8H, m)

PREPARATION EXAMPLE 19

Preparation of N-(4-Chloro-4'-trifluoromethylsulfonylmethylbenzhydryl)-N'-methoxycarbonylhydrazine Hydrochloride (Compound No. V-13)

N-(4-chloro-4'-trifluoromethylsulfonylmethylbenzhydryl)-N'-methoxycarbonylhydrazine (1.6 g) was added to methanol (80 ml), and hydrochloric acid (3 ml) was added thereto with stirring at room temperature. The mixture was gradually heated to the reflux temperature and stirred for 2 hours under reflux, and then it was left to cool. The solvent was distilled off under reduced pressure to obtain the desired product as a slightly yellow powder (1.6 g, melting point: 52° to 54° C., yield: 91.5%).

$^1$H-NMR data (60 MHz, CDCl$_3$ solvent, δ value)

3.6 (3H, s)

4.73 (2H, s)

5.23 (1H, s)

7.27–7.50 (8H, m)

PREPARATION EXAMPLE 20

Preparation of 4-Chloro-4'-ethylthiomethylbenzophenone -N'-ethoxycarbonylhydrazone (Compound No. I-114)

Ethane thiol (1.2 g) and sodium hydroxide (1 g) were suspended in N,N-dimethylformamide (50 ml), and then 4-chloro-4'-chloromethylbenzophenone-N'-ethoxycarbonylhydrazone (3.5 g) was added thereto. The mixture was stirred for 16 hours at room temperature. Water was added to the reaction mixture, and the mixture was extracted with ethyl acetate. The ethyl acetate layer was washed with water and then dried over anhydrous magnesium sulfate. Ethyl acetate was distilled off under reduced pressure. The residue was purified by silica gel column chromatography (n-hexane:ethyl acetate=4:1) to obtain the desired product (2.0 g, n$_D^{20}$:1.6198, yield: 53%).

$^1$H-NMR data (60 MHz, CDCl$_3$ solvent, δ value) 1.34 (6H, t) 2.53 (2H, q) 3.70, 3.80 (2H, q)

7.10–7.77 (8H, m)

PREPARATION EXAMPLE 21

Preparation of 4-Chloro-4'-difluoromethylthiomethylbenzophenone-N'-methoxycarbonylhydrazone (Compound No. I-187)

4-chloro-4'-mercaptomethylbenzophenone-N'-methoxycarbonylhydrazone (1.5 g) and potassium hydroxide (1.5 g) were added to a solvent comprising dioxane (30 ml) and water (30 ml). Difluoromethyl chloride was blown into this solution at 40° C. until the starting material 4-chloro-4'-mercaptomethylbenzophenone-N'-methoxycarbonylhydrazone disappeared. The reaction mixture was cooled to room temperature and subjected to filtration. The organic layer as the filtrate was dried over anhydrous magnesium sulfate and concentrated. The residue was purified by silica gel column chromatography (n-hexane:ethyl acetate=4:1) to obtain the desired product (0.3 g, n$_D^{20}$:1.6213, yield: 18%).

$^1$H-NMR data (60 MHz, CDCl$_3$ solvent, δ value)

3.78 (3H, s)

3.98, 4.10 (2H, s, s) 6.7, 6.8 (1H, t) 7.07–7.67 (8H, m) 7.77 (1H, s)

PREPARATION EXAMPLE 22

Preparation of 4-Chloro-4'-methylthiomethylbenzophenone-N'-methoxycarbonylhydrazone (Compound No. I-67)

4-chloro-4'-hydroxymethylbenzophenone-N'-methoxycarbonylhydrazone (1.2 g) and triethylamine (0.5 g) were added to tetrahydrofuran (30 ml). Chlorobis (diethylaminophosphine) (1.1 g) was dropwise added to this solution at −20° C. The mixture was stirred for 2 hours at room temperature, and then the solvent was distilled off under reduced pressure. Ice water and ethyl acetate were added thereto for liquid separation. The organic layer was dried over anhydrous magnesium sulfate and concentrated to obtain a phosphite. This phosphite was added to tetrahydrofuran (30 ml). Dimethyl sulfide (0.9 g) was dropwise added to this solution at 0° C., and the mixture was further stirred for 12 hours at room temperature. After confirming that the starting material phosphite disappeared, the solvent was distilled off under reduced pressure. The residue was purified by silica gel column chromatography (n-hexane:ethyl acetate=4:1) to obtain the desired product (0.3 g, melting point: 40° to 42° C., yield: 17%).

$^1$H-NMR data (60 MHz, CDCl$_3$ solvent, δ value)

1.93, 2.08 (3H, s, s)

3.67, 3.77 (2H, s, s)

3.8 (3H, s)

7.1–7.67 (8H, m) 7.85 (1H, br)

PREPARATION EXAMPLE 23

Preparation of 4-Chloro-4'-methylsulfonylmethyl-benzophenone (Compound No. VI-3)

4-bromomethyl-4'-chlorobenzophenone (3.1 g) and sodium methanesulfinate (1.5 g) were added to N,N-dimethylformamide (50 ml), and the mixture was stirred for 16 hours at room temperature. Water was added to the reaction mixture, and the mixture was extracted with ethyl acetate. The ethyl acetate layer was washed with water and dried over anhydrous magnesium sulfate. Ethyl acetate was distilled off under reduced pressure. The residual solid was washed with n-hexane to obtain the desired product (2.8 g, melting point: 164° to 166° C., yield: 90%).

$^1$H-NMR data (60 MHz, CDCl$_3$ solvent, δ value) 2.90 (3H, s) 4.47 (2H, s) 7.37–7.83 (8H, m)

PREPARATION EXAMPLE 24

Preparation of 4-Chloro-4'-ethylsulfonylethyl-benzophenone (Compound No. VI-6)

Sodium sulfite (24.5 g) and sodium hydrogen carbonate (33 g) were dissolved in water (200 ml). Ethane sulfonyl chloride (25 g) was dropwise added to this solution at room temperature in 30 minutes, and the mixture was stirred for one hour. This reaction mixture was concentrated, and the residue was suspended in N,N-dimethylformamide (200 ml). Then, 4-bromomethyl-4'-chlorobenzophenone (10.0 g) was added thereto, and the mixture was stirred for 16 hours at room temperature. Water was added to the reaction mixture, and the mixture was extracted with ethyl acetate. The ethyl acetate layer was washed with water and then dried over anhydrous magnesium sulfate. Ethyl acetate was distilled off under reduced pressure. The residual solid was washed with n-hexane to obtain the desired product (7.5 g, melting point: 117° to 118° C., yield: 72%).

$^1$H-NMR data (60 MHz, CDCl$_3$ solvent, δ value) 1.37 (3H, t) 2.93 (2H, q) 4.27 (2H, s) 7.20–7.83 (8H, m)

PREPARATION EXAMPLE 25

Preparation of 4-Chloro-4'-ethylthiomethylbenzophenone (Compound No. VI-4)

4-chloro-4'-mercaptomethylbenzophenone (16.0 g), ethyl bromide (7.4 g) and potassium hydroxide (4.3 g) were added to methanol (250 ml), and the mixture was stirred for 30 minutes under reflux. The reaction mixture was cooled to room temperature and then concentrated. Water was added to the residue, and the mixture was extracted with ethyl acetate. The ethyl acetate layer was washed with water and then dried over anhydrous magnesium sulfate and concentrated. The residue was purified by silica gel column chromatography (n-hexane:ethyl acetate=10:1) to obtain the desired product 14.0 g, melting point: 33° to 34° C., yield: 79%).

$^1$H-NMR data (60 MHz, CDCl$_3$ solvent, δ value) 2.23 (3H, t) 2.45 (2H, s) 3.75 (2H, s) 7.10–7.90 (8H, m)

PREPARATION EXAMPLE 26

Preparation of 4-Chloro-4'-difluoromethylthiomethyl-benzophenone (Compound No. VI-15)

4-chloro-4'-mercaptomethylbenzophenone (14.7 g) and potassium hydroxide (15 g) was added to a solvent comprising dioxane (100 ml) and water (100 ml). Difluoromethyl chloride was blown into this solution at 60° C. until the starting material 4-chloro-4'-mercaptomethylbenzophenone disappeared. The reaction product was cooled to room temperature and then subjected to filtration. The organic layer as the filtrate was dried over anhydrous magnesium sulfate add concentrated. The residue was purified by silica gel column chromatography (n-hexane:ethyl acetate=5:1) to obtain the desired product (6.4 g, melting point: 34° to 35° C., yield: 36%).

$^1$H-NMR data (60 MHz, CDCl$_3$ solvent, δ value) 4.03 (2H, s) 6.69 (1H, t) 7.15–7.71 (8H, m)

PREPARATION EXAMPLE 27

Preparation of 4-Chloro-4'-difluoromethylsulfonylmethyl-benzophenone (Compound No. VI-16)

4-chloro-4'-difluoromethylthiomethylbenzophenone (3.2 g) and m-chloroperbenzoic acid (5.3 g) were added to chloroform (150 ml). This suspension was stirred for 3 hours under reflux. The reaction mixture was concentrated, and water was added to the residue. The mixture was extracted with ethyl acetate. The ethyl acetate layer was washed with water and then dried over anhydrous magnesium sulfate. Ethyl acetate was distilled off under reduced pressure. The residual solid was washed with n-hexane to obtain the desired product (2.7 g, melting point: 154° to 157° C., yield: 78%).

$^1$H-NMR data (60 MHz, CDCl$_3$ solvent, δ value) 4.57 (2H, s) 6.41 (1H, t) 7.27–7.87 (8H, m)

PREPARATION EXAMPLE 28

Preparation of 4-Chloro-4'-trifluoromethylthiomethyl-benzophenone (Compound No. VI-12)

4-chloro-4'-mercaptomethylbenzophenone (4.5 g) was dissolved in tetrahydrofuran (150 ml). 60% sodium hydride (0.8 g) was added to this solution, and the mixture was stirred for 30 minutes at room temperature. Then, S-(trifluoromethyl)dibenzothiophenium-trifluoromethane sulfonate (6.4 g) was added thereto, and the mixture was further stirred for 30 minutes. The reaction mixture was concentrated, and water was added thereto. The mixture was extracted with ethyl acetate. The ethyl acetate layer was washed with water and then dried over anhydrous magnesium sulfate. Ethyl acetate was distilled off under reduced pressure. The residue was purified by silica gel column chromatography (n-hexane:ethyl acetate=4:1) to obtain the desired product (2.0 g, melting point: 63° to 65° C., yield: 35%).

$^1$H-NMR data (60 MHz, CDCl$_3$ solvent, δ value)
4.14 (2H, s)
7.30–7.77 (8H, m)

PREPARATION EXAMPLE 29

Preparation of 4-Chloro-4'-(1,1,2,2-tetrafluoroethyl-thiomethylbenzophenone (Compound No. VI-20)

4-chloro-4'-mercaptomethylbenzophenone (5.0 g) and potassium tert-butoxide (0.9 g) were added to ethanol (150 ml). Perfluoroethylene (2.9 g) were blown thereinto at room temperature, and the mixture was then stirred for 16 hours. The reaction mixture was filtered and concentrated. The residue was purified by silica gel column chromatography (n-hexane:ethyl acetate=4:1) to obtain the desired product 5.3 g, melting point: 48° to 50° C., yield: 77%).

$^1$H-NMR data (60 MHz, CDCl$_3$ solvent, δ value) 4.13 (2H, s) 5.77 (1H, tt) 7.23–7.73 (8H, m)

PREPARATION EXAMPLE 30

Preparation of 4-Chloro-4'-methylthiomethylbenzophenone (Compound No. VI-1)

4-bromomethyl-4'-chlorobenzophenone (3.1 g) and 15% methylmercaptan-sodium aqueous solution (5.6 g) were added to methanol (150 ml), and the mixture was stirred for 30 minutes under reflux. The reaction mixture was concentrated and extracted with ethyl acetate. The ethyl acetate layer was washed with water and then dried over anhydrous magnesium sulfate. Ethyl acetate was distilled off under reduced pressure. The residual solid was washed with n-hexane to obtain the desired product (2.3 g, melting point: 59° to 61° C., yield: 83%).

$^1$H-NMR data (60 MHz, CDCl$_3$ solvent, δ value) 2.00 (3H, s) 3.70 (2H, s) 7.13–7.74 (8H, m)

PREPARATION EXAMPLE 31

Preparation of 4-Chloro-4'-methylsulfinylmethylbenzophenone (Compound No. VI-2)

4-chloro-4'-methylthiomethylbenzophenone (4.2 g) was added to methanol (150 ml). Sodium periodate (3.6 g) dissolved in water (20 ml), was added to this solution, and the mixture was stirred for 16 hours at room temperature. The reaction mixture was concentrated, and water was added thereto. The mixture was extracted with ethyl acetate. The ethyl acetate layer was washed with water and then dried over anhydrous magnesium sulfate. Ethyl acetate was distilled off under reduced pressure. The residual solid was washed with n-hexane to obtain the desired product (4.1 g, melting point: 116° to 118° C., yield: 93%).

$^1$H-NMR data (60 MHz, CDCl$_3$ solvent, δ value)
2.50 (3H, s)
4.00 (2H, s)
7.30–7.80 (8H, m)

PREPARATION EXAMPLE 32

Preparation of 4-(3-Bromopropyl)sulfonylmethyl-4'-chlorobenzophenone (Compound No. VI-11)

4-(3-bromopropyl)thiomethyl-4'-chlorobenzophenone (5.1 g) and a 31% hydrogen peroxide aqueous solution (6 g) was added to acetic acid (200 ml), and the mixture was stirred for one hour at 80° C. and further for one hour under reflux. The reaction mixture was concentrated, and water was added thereto. The mixture was extracted with ethyl acetate. The ethyl acetate layer was washed with an aqueous potassium carbonate solution and water and dried over anhydrous magnesium sulfate. Ethyl acetate was distilled off under reduced pressure. The residual solid was washed with n-hexane to obtain the desired product (5.0 g, melting pint: 105° to 107° C., yield: 91%).

$^1$H-NMR data (60 MHz, CDCl$_3$ solvent, δ value)
2.17–2.60 (2H, m)
3.00–3.17 (2H, m)
3.53 (2H, t)
4.33 (2H, s)
7.23–7.87 (m, 8H)

PREPARATION EXAMPLE 33

Preparation of 4-Chloro-4'-(1,1-dioxothiolan-2-yl) benzophenone (Compound No. VI-36)

4-(3-bromopropyl)sulfonylmethyl-4'-chlorobenzophenone (2.5 g) and 60% sodium hydride (0.3 g) were added to N,N-dimethylacetamide (70 ml), and the mixture was stirred for 16 hours at room temperature. Water was added to the reaction mixture, and the mixture was extracted with ethyl acetate. The ethyl acetate layer was washed with water and then dried over anhydrous magnesium sulfate. Ethyl acetate was distilled off under reduced pressure. The residue was purified by silica gel column chromatography (n-hexane:ethyl acetate=1:1) to obtain the desired product as a slightly yellow viscous substance 1.0 g, yield: 50%).

$^1$H-NMR data (60 MHz, CDCl$_3$ solvent, δ value)
2.67–2.73 (4H, m).
2.87–3.33 (2H, m)
4.02–4.37 (1H, m) 7.23–7.97 (8H, m)

PREPARATION EXAMPLE 34

Preparation of 4-Chloro-4'-(2-trifluoromethylsulfonylpropyl)benzophenone (Compound No. VI-28)

4-chloro-4'-trifluoromethylsulfonylmethylbenzophenone (3.3 g) and 60% sodium hydride (0.8 g) were added to N,N-dimethylacetamide (150 ml), and the mixture was stirred for one hour at room temperature. Methyl iodide (0.8 g) was added to this solution, and the mixture was stirred for 16 hours at room temperature. Water was added to the reaction mixture, and the mixture was extracted with ethyl acetate. The ethyl acetate layer was washed with water and then dried over anhydrous magnesium sulfate. Ethyl acetate was distilled off under reduced pressure. The residue was purified by silica gel column chromatography (n-hexane:ethyl acetate=4:1) to obtain the desired product (3.1 g, melting point 107° to 109° C., yield: 86%).

$^1$H-NMR data (60 MHz, CDCl$_3$ solvent, δ value) 2.00 (6H, s) 7.20–7.70 (8H, m)

PREPARATION EXAMPLE 35

Preparation of 4-Chloro-4'-thiocyanatomethylbenzophenone (Compound No. VI-35)

4-bromomethyl-4'-chlorobenzophenone (5.7 g) and sodium thiocyanate (5.5 g) were added to ethanol (50 ml), and the mixture was stirred for one hour at 60° C. The reaction mixture was concentrated, and water was added to the residue. The mixture was extracted with ethyl acetate. The ethyl acetate layer was washed with water and then dried over anhydrous magnesium sulfate. Ethyl acetate was distilled off under reduced pressure. The residual solid was washed with a solvent mixture of n-hexane:ethyl acetate= 10:1 to obtain the desired product (2.2 g, melting point: 129° to 131° C., yield:42%).

$^1$H-NMR data (60 MHz, CDCl$_3$ solvent, δ value) 4.18 (2H, s) 7.23–7.87 (8H, m)

PREPARATION EXAMPLE 36

Preparation of Diethyl 2-{4-(4-chlorobenzoyl)phenyl}-2-trifluoromethylthiomalonate (Compound No. VI-80)

60% sodium hydride (0.5 g) was dispersed in tetrahydrofuran (150 ml), and diethyl 2-{4-(4-chlorobenzoyl)phenyl}malonate (4.4 g) was dropwise added thereto at 0° C. with stirring. After generation of hydrogen ceased, trifluoromethylsulphenyl chloride was blown thereinto at 0° C., and the mixture was then stirred for one hour at room temperature. The reaction mixture was concentrated, and water was added to the residue. The mixture was extracted with ethyl acetate. The ethyl acetate layer was washed with water and then dried over anhydrous magnesium sulfate. Ethyl acetate was distilled off under reduced pressure. The residue was purified by silica gel column chromatography (n-hexane:ethyl acetate=8:1) to obtain the desired product (4.7 g, n$_D^{20}$:1.5362, yield:87%).

$^1$H-NMR data (60 MHz, CDCl$_3$ solvent, δ value) 1.3 (6H, t) 4.35 (4H, q) 7.4 (2H, d) 7.75 (2H, d) 7.8 (4H, s)

PREPARATION EXAMPLE 37

Preparation of 4-Chloro-4'-trichloromethylthiomethylbenzophenone (Compound No. VI-81)

Methylbenzophenone 4-chloro-4'-thiocyanate (5.5 g) and triethylbenzylammonium chloride (0.5 g) were dispersed in chloroform (30 ml), and a 48% sodium hydroxide aqueous solution (4 ml) was added thereto at 40° C. Then, the mixture was stirred for 3 hours.

Cool water was added thereto, and the mixture was subjected to liquid separation. The organic layer was washed with water and dried over anhydrous magnesium sulfate. Then, chloroform was distilled off under reduced pressure. The residue was purified by silica gel column chromatography (n-hexane:ethyl acetate=9:1) to obtain the desired product (1.0 g, melting point: 103° to 105° C., yield: 13%).

$^1$H-NMR data (60 MHz, CDCl$_3$ solvent, δ value) 4.45 (2H, s) 7.15–7.8 (8H, m)

PREPARATION EXAMPLE 38

Preparation of 4-Chloro-4'-trifluoromethylsulfonylmethylbenzhydrol (Compound No. VIII-2)

4-chloro-4'-trifluoromethylsulfonylmethylbenzophenone (5.5 g) was dispersed in methanol (200 ml). Sodium borohydride was gradually added thereto at room temperature with stirring, and the mixture was further stirred overnight at room temperature. After completion of the reaction, methanol was distilled off under reduced pressure. The residue was extracted with ethyl acetate (250 ml). The extract was washed with water and dried over anhydrous magnesium sulfate. Then, ethyl acetate was distilled off under reduced pressure. The residue was purified by silica gel column chromatography (n-hexane:ethyl acetate=2:1) to obtain the desired product as a white powder (4.2 g, melting point: 113° to 115° C., yield: 77%).

$^1$H-NMR data (60 MHz, CDCl$_3$ solvent, δ value) 4.7 (2H, s) 5.77 (2H, s) 7.3 (4H, s) 7.47 (4H, s)

PREPARATION EXAMPLE 39

Preparation of 4-Chloro-4'-ethane Sulfonylmethylbenzhydryl Chloride (Compound No. VIII-5)

4-chloro-4'-ethane sulfonylmethylbenzhydrol (6.0 g), thionyl chloride (5.4 g), toluene (200 ml) and a catalytic amount of N,N-dimethylformamide were mixed and gradually heated with stirring to a refluxing temperature. The mixture was stirred for 4 hours under reflux and then left to cool. Then, the solvent was distilled off under reduced pressure. The residue was purified by silica gel column chromatography (n-hexane:ethyl acetate=2:1) to obtain the desired product as a slight yellow viscous substance (4.6 g, n$_D^{20}$: 1.6044, yield: 75%).

$^1$H-NMR data (60 MHz, CDCl$_3$ solvent, δ value) 1.33 (3H, t) 2.88 (2H, q) 4.37 (2H, s) 6.05 (1H, s) 7.27 (4H, s) 7.35 (4H, s)

PREPARATION EXAMPLE 40

Preparation of (6-Chloro-3-pyridyl)(4-trifluoromethylphenyl) ketone (Compound No. VII-3)

(6-chloro-3-pyridyl)(4-thicyanatemethylphenyl) ketone (5.0 g) was dissolved in tetrahydrofuran (300 ml), and trifluoromethyltrimethyl silane (5.0 g) was added thereto at room temperature. Then, the mixture was cooled to 5° C. Tetrabutylammonium fluoride (1.0M tetrahydrofuran solution, 23 g) was gradually dropwise added thereto under cooling, and then, the mixture was stirred over night. Tetrahydrofran was distilled off under reduced pressure, and the residue was extracted with ethyl acetate. The extract was washed with water and dried over anhydrous magnesium sulfate. Then, ethyl acetate was distilled off under reduced pressure. The residue was purified by silica gel column chromatography (n-hexane:ethyl acetate=4:1) to obtain the desired product (2.0 g, n$_D^{20}$: 1.5820, yield: 35%).

$^1$H-NMR data (60 MHz, CDCl$_3$ solvent, δ value) 4.15 (2H, s) 7.4 (3H, dd) 7.72 (2H, dd) 8.05 (2H, dd) 8.67 (2H, d)

PREPARATION EXAMPLE 41

Preparation of 4-Chloro-4'-hydroxymethylbenzophenone-N'-methoxcarbonylhydrazone (Compound No. IX-1)

4-chloro-4'-hydroxymethylbenzophenone (0.5 g) and methyl-carbazate (0.4 g) were added to ethanol (60 ml) and acetic acid (5 ml), and the mixture was stirred for 2 hours under reflux. The reaction mixture was concentrated, and the residue was extracted with ethyl acetate. The ethyl acetate layer was washed with water and then dried over anhydrous magnesium sulfate. Ethyl acetate was distilled off under reduced pressure. The residue was purified by silica gel column chromatography (n-hexane: ethyl acetate=4:1) to obtain the desired product (0.5 g, yield 83%).

$^1$H-NMR data (60 MHz, CDCl$_3$ solvent, δ value)

2.17 (1H, br)

3.77 (3H, s)

4.63, 4.73 (2H, s, s)

6.97–7.63 (8H, m)

7.73 (1H, br)

When the compound of the present invention is to be used as the active component of a pesticide, it may be used by itself. However, it can be formulated into various formulations such as an emulsifiable concentrate, a suspension, a dust, a granule, a tablet, a wettable powder, a water-soluble concentrate, a solution, a flowable suspension, a water dispersible granule, an aerosol, a paste, an oil formulation, a concentrated emulsion in water in combination with various carriers, surfactants and other adjuvants which are commonly used for formulation as agricultural adjuvants. They are blended usually in such proportions that the active ingredient is from 0.1 to 90 parts by weight and the agricultural adjuvants are from 10 to 99.9 parts by weight.

The carriers to be used for such formulation may be classified into solid carriers and liquid carriers. The solid carriers include, for example, animal and plant powders such as starch, active carbon, soybean powder, wheat powder, wood powder, fish powder and powdered milk, and mineral powders such as talc, kaolin, bentonite, calcium carbonate, zeolite, diatomaceous earth, fine silica powder, clay and alumina. The liquid carries include, for example, water, alcohols such as isopropyl alcohol and ethylene glycol, ketones such as cyclohexanone and methyl ethyl ketone, ethers such as dioxane and tetrahydrofuran, aliphatic hydrocarbons such as kerosene and light oil, aromatic hydrocarbons such as xylene, trimethylbenzene, tetramethylbenzene, methylnaphthalene and solvent naphtha, halogenated hydrocarbons such as chlorobenzene, acid amides such as dimethylacetamide, esters such as glycerin esters of fatty acids, nitriles such as acetonitrile, and sulfur-containing compounds such as dimethylsulfoxide.

The surfactants include, for example, metal salts of alkylbenzene sulfonic acids, metal salts of dinaphthylmethanedisulfonic acid, alcohol sulfuric acid esters, alkylarylsulfonates, lignin sulfonates, polyoxyethylene glycol ethers, polyoxyethylene alkyl aryl ethers and polyoxyethylene sorbitan monoalkylates.

Others adjuvants include, for example, an adhesive or thickener such as carboxymethylcellulose, gum arabic, sodium arignate, guar gum, tragacanth gum or polyvinyl alcohol, an antifoaming agent such as metal soap, a physical property-improving agent such as a fatty acid, an alkyl phosphate, silicone or paraffin, and a coloring agent.

When these formulations are to be practically used, they may be used as they are or as diluted with a diluting agent such as water to a predetermined concentration. Various formulations containing the compounds of the present invention or their diluted solutions may be applied by conventional methods i.e. application methods (such as spraying, misting, atomizing, dusting, granule application, paddy water application or seeding box treatment), soil treatment (such as mixing or drenching), surface application (such as painting, dressing or covering), dipping or poison bait. Further, the above active component may be fed as mixed in feeds to domestic animals, so that infestation or growth of pests, particularly injurious insects can be prevented by the excrements. Otherwise, it can also be applied by a so-called super high concentration low volume application method, whereby the active component may be contained up to 100%.

The pesticide of the present invention is applied usually in a concentration of the active ingredient of from 0.1 to 50,000 ppm, preferably from 1 to 10,000 ppm.

The concentration of the active ingredient can be suitably changed depending upon the type of the formulation, the method, the purpose, the season or the site of application and the state of infestation of pests. For example, in the case of aquatic pests, they can be controlled by applying a formulation having a concentration within the above mentioned range to the infested site, and therefore, the range of the active ingredient in water is lower than the above range. The dose per unit area is usually from 0.1 to 5,000 g, preferably from 1 to 1,000 g, per 1 ha of the active compound. However, the dose is not limited to such a specific range.

The compound of the present invention is sufficiently effective when used alone. However, as a case requires, it may be used in combination or in admixture with fertilizers or other agricultural chemicals such as insecticides, acaricides, nematicides, fungicides, antivirus agents, attractants, herbicides or plant growth regulants, and further improved effects may sometimes be obtained by such combined use.

Typical examples of the insecticides, fungicides and acaricides which can bemused in combination with the compound of the present invention, will be given below.

Organophosphorus compounds and carbamate insecticides: fenthion, fenitrothion, diazinon, chlorpyriphos, oxydeprofos, vamidothion, phenthoate (fentoat), dimethoate, formothion, malathion, trichlorphon, thiometon, phosmet, dichlorvos, acephate, EPBP (0-2,4-dichlorophenyl 0-ethylphenylphosphonothioate), methyl-parathion, oxydemeton-methyl, ethion, dioxabezofos, cyanophos (cyanofos), isoxathion, pyridafenthion, phosalone, metidation, sulprophos (sulprofos), chlorfenvinphos, tetrachlorvinphos, dimethylvinphos, propahos, isofenphos, disulfoton, profenofos, pyraclofos, monocrotophos, azinphos-methyl, aldikarb, methomyl, thiodicarb, carbofuran, carbosulfan, benfuracarb, furathiocarb, propoxur, fenobcarb, metolcarb, isoprocarb, carbaryl (carbaril), pirimicarb, ethiofencarb, dichlophenthion, pirimiphos-methyl, quinalphos, chlorpyriphos-methyl, prothiophos, naled, bendiocarb, oxamyl, alanycarb, chlorethoxyfos, etc.

Pyrethroid insecticides: permethrin, cypermethrin, deltamethrin, fenvalerate, fenpropathrin, piretrine, allethrin, tetramethrin, resmethrin, dimethrin, proparthrin, phenothrin, prothrin, fluvalinate, cyfluthrin, cyhalothrin, flucythrinate, etofenprox, cycloprothrin, tralomethrin, silafluofen, tefluthrin, bifenthrin, acrinathrin, etc.

Acylurea type and other insecticides: diflubenzuron, chlorfluazuron, hexaflumuron, triflumuron, teflubenzuron, flufenoksuron, flucycloxuron, buprofezin, pyriproxyfen, lufenuron, cyromazine, methoprene, endosulphan, diafenthiuron, imidacloprid, fipronil, nicotin-sulfate, rotenone, metaldehyde, machine oil, fenoxycarb, cartap, thiocyclam, bensultap, tebufenozide, chlorphenapyr, emamectin-benzoate, acetamiprid, nitenpyram, pymetrozine, sodium oleate, rapeseed oil, etc.

Nematicides: phenamiphos, fosthiazate, ethoprophos, methyl isothiocyanate, 1,3-dichloropropene, DCIP, etc.

Acaricides: chlororbenzilate, phenisobromolate, dicofol, amitraz, propargit, benzomate, hexythiazox, fenbutatin oxide, polynactins, quinomethionate, chlorfenson, tetradifon, avermectin, milbemectin, clofentezine, pyridaben, fenpyroximate, tebufenpyrad, pyrimidifen, fenothiocarb, dienochlor, etoxazole, halfenprox, etc.

Fungicides: thiophanate-methyl, benomil, carbendazol, thiabendazol, folpet, thiuram, diram, zineb, maneb, manzeb, polycarbamate, iprobenfos, edifenphos, fthalide, probenazole, isoprothiolane, chlorothalonil, captan, polyoxin, blasticidin-S, kasugamycin, streptomycin, validamycin, tricyclazole, pyroquilone, phenazine oxide, mepronil, flutolanil, pencycuron, iprodione, hymexazol, metalaxyl, triflumizole, triforine, triadimefone, bitertanol, fenarimol, propikonazol, cymoxanil, prochloraze, pefurazoate, hexaconazole, myclobutanil, diclomezine, tecloftalam, propineb, dithianon, phosethyl, vinclozolin, procymidone, oxadixyl, guazatine, propamocarb-hydrochloride, fluazinam, oxolinic acid, hydroxyisoxazole, imibenconazole, difenoconazole, mepanipyrim.

The compounds of the present invention exhibit excellent pesticidal activities against pests such as hemipteran insects, lepidopteran insects, coleopteran insects, dipteran insects, hymenopteran insects, orthopteran insects, isopteran insects, thysanopteran insects, mites and plant-parasitic nematodes. The following pests may be mentioned as such pests.

Hemipteran insects: bugs (HETEROPTERA) such as bean bug (*Riptortus clavatus*), southern green stink bug (*Nezara viridula*), lygus bugs (Lygus sp.), hairy chinch bug (*Blissus leucopterus*) and pear lace bug (*Stephanitis nashi*); leafhoppers (Circulifer sp.) such as green rice leafhopper (*Nephotettix cincticeps*) and leafhoppers (Empoasca sp., Erythroneura sp., Circulifer sp.); planthoppers (Delphacidae) such as brown rice planthopper (*Nilaparvata lugens*), whitebacked planthopper (*Sogatella furcifera*) and small brown planthopper (*Laodelphax striatellus*); jumping plantlice (Psyllidae) such as Psyllids (Psylla sp.); whiteflies (Aleyrodidae) such as sweetpotato whitefly (*Bemisia tabaci*) and greenhouse whitefly (*Trialeurodes vaporariorum*); aphides (Aphididae) such as grapeleaf louse (*Viteus vitifolii*), green peach aphid (*Myzus persicae*), green apple aphid (*Aphis pomi*), cotton aphid (*Aphis gossypii*), *Aphis fabae*, turnip aphid (*Rhopalosiphum psedobrassicas*), glasshouse-potato aphid (*Aulacorthum solani*) and greenbug (*Schizaphis graminum*); mealy bugs or scales such as comstock mealybug (*Pseudococcus comstocki*), red wax scale (*Ceroplastes rubens*), San Jose scale (*Comstockaspis perniciosa*) and arrowhead scale (*Unaspis yanonensis*).

Lepidopteran insects: tortricids (Tortricidae) such as oriental tea tortrix (*Homona magnanima*), summer fruit tortrix (*Adoxophyes orana*), torticids (*Sparganothis pilleriana*), oriental fruit moth (*Grapholitha molesta*), soybean pod borer (*Leguminivora glycinivorella*), codling moth (*Laspeyresia pomonella*), tortricids (Eucosma sp.) and grape berry moth (*Lobesia botrana*); Cochylidae such as grape cochylid (*Eupoecillia ambiguella*); bagworm moths (Psychidae) such as Bambalina sp.; tineids (Tineidae) such as European grain moth (*Nemapogon granellus*) and case-making clothes moth (*Tinea translucens*); lyonetiid moths (Lyonetiidae) such as *Lyonetia prunifoliella*; leafblotch miners such as apple leafminer (*Phyllonorycter rigoniella*); Phyllocnistidae such as citrus leafminer (*Phyllocnistis citrella*); yponomeutids such as diamondback moth (*Plutella xylostella*) and yponomeutid moths (*Prays citri*); clearwing moths (Synanthedon sp.) such as grape clearwing moth (*Paranthrene regalis*) and Synanthedon sp.; gelechiid moths (Gelechiidae) such as pink bollworm (*Pectinophora gossypiella*), potato tuberworm (*Phthorimaea operculella*) and Stomopteryx sp.; Carposinidae such as peach fruit moth (*Carposina niponensis*); slug caterpillarmoths such as oriental moth (*Monema flavescens*); pyralid moths such as rice stem borer (*Chilo suppressalis*), rice leafroller (*Cnaphalocrocis medinalis*), European corn borer (*Ostrinia nubilalis*), oriental corn borer (*Ostrinia furnacalis*), cabbage webworm (*Hellula undalis*), greater wax moth (*Galleria mellonella*), lesser cornstalk borer (*Elasmopalpus lignosellus*) and beet webworm (*Loxostege sticticalis*); whites such as common cabbage worm (*Pieris rapae*); geometrid moths such as mugwort looper (*Ascotis selenaria*); tent caterpillar moths such as tent caterpillar (*Malacosoma neustria*); sphinx moths such as tobacco hornworm (*Manduca sexta*); tussock moths such as tea tussock moth (*Euproctis pseudoconspersa*) and gypsy moth (*Lymantria dispar*); tiger moths such as fall webworm (*Hyphantria cunea*); owlet moths such as tobacco budworm (*Heliothis virescens*), bollworm (*Helicoverpa zea*), beet armyworm (*Spodoptera exigua*), cotton bollworm (*Helicoverpa armigera*), common cutworm (*Spodoptera litura*), cabbage armyworm (*Mamestra brassicae*), black cutworm (*Agrotis ipsiron*), rice armyworm (*Pseudaletia separata*) and cabbage looper (*Trichoplusia ni*).

Coleopteran insects: chafers such as cupreous chafer (*Anomala cuprea*), Japanese beetle (*Popillia japonica*), soybean beetle (*Anomala rufocuprea*) and *Eutheola rugiceps*; click beetles (Conodeus sp.) such as wireworm (Agriotes sp.) and Conodeus sp.; ladybird beetles such as twenty-eight-spotted ladybird (*Epilachna vigintioctopunctata*) and Mexican bean beetle (*Epilachna varivestis*); darkling beetles such as red-brown rice-flour beetle (*Tribolium castaneum*); longicorn beetles such as whitespotted longicorn beetle (*Anoplophora malasiaca*) and Japanese pine sawyer (*Monochamus alternatus*); seed beetles such as bean weevil (*Acanthoscelides obtectus*) and adzuki bean weevil (*Callosobruchus chinensis*); leaf beetles such as colorado potato beetle (*Leptinotarsa decemlineata*), corn rootworm (Diabrotica sp.), rice leaf beetle (*Oulema oryzae*), beet flea beetle (*Chaetocnema concinna*), mustard beetle (*Phaedon cochlearias*), cereal leaf beetle (*Oulema melanopus*) and *Dicladispa armigera*; Apionidae such as *Apion godmani*; weevils such as rice water weevil (*Lissorhoptrus oryzophilus*) and cotton boll weevil (*Anthonomus grandis*); Rhynchophoridae such as maize weevil (*Sitophilus zeamais*); bark beetles; skin beetles; drugstore beetles.

Dipteran insects: rice crane fly (*Tipra ano*), rice midge (*Tanytarsus oryzae*), *Orseolia oryzae*, *Ceratitis capitata*, rice leafminer (*Hydrellia griseola*), cherry drosophila (*Drosophila suzukii*), frit fly (*Oscinella frit*), rice stem maggot (*Chlorops oryzae*), French bean miner (*Ophiomyia phaseoli*), legume leafminer (*Liriomyza trifolii*), beet leafminer (*Pegomya hyoscyami*), seedcorn maggot (*Hylemia platura*), sorghum fly (*Atherigona soccata*), muscid fly (*Musca domestica*), *Gastrophilus* sp., stomoxiid flies (*Stomoxys* sp.), *Aedes aegypti*, *Culex pipiens*, *Anopheles slnensis* and *Culex tritaeniorhynchus*.

Hymenopteran insects: stem sawflies (Cephus sp.); eurytomids (Harmolita sp.); cabbage sawfly (Athalia sp.), hornets (Vespa sp.) and fire ants.

Orthopteran insects: German cockroach (*Blatella germanica*); American cockroach (*Periplaneta americana*); mole crichet (*Gryllotalpa africana*); Asiatic locust (*Locusta migratoria migratoriodes*); and *Melanoplus sanguinipes*.

Termites insects: termites (*Reticulitermes speratus*) and formosan subterranean termite (*Coptotermes formosanus*).

Thrips insects: yellow tea thrips (*Scirtothrips dorsalis*); thrips (*Thrips palmi*); greenhouse thrips (*Heliothrips* haemorrholidalis); western flower thrips (*Frankliniella occidentalis*) and rice aculeated thrips (*Haplothrips aculeatus*).

Mites: twospotted spider mite (*Tetranychus urticae*); Kanzawa spider mite (*Tetranychus kanzawai*); citrus red mite (*Panonychus citri*); European red mite (*Panonychus ulmi*), yellow spider mite (*Eotetranychus carpini*); Texas citrus mite (*Eotetranychus banksi*); citrus rust mite (*Phyllocoptruta oleivora*); broad mite (*Polyphagotarsonemus latus*); false spider mites (Brevipalpus sp.); bulb mite (*Rhizoglyphus robini*) and mold mite (*Tyrophagus putrescentiae*).

Plant-parasitic nematodes: southern root-knot nematode (*Meloidogyne incognita*); root-lesion nematode (Pratylenchus sp.); soybean cyst nematode (*Heterodera glycines*); rice white-tip nematode (*Aphelenchoides besseyi*) and pine wood nematode (*Bursaphelenchus xylophilus*).

Other pests and parasites: Gastropoda such as apple snails (*Pomacea canaliculata*); slugs (Incilaria sp.) and giant African snail (*Achatina fulica*); pillbugs (Isopoda) such as sow bug and centipede; booklice (Liposcelis sp.); oriental siverfish (Ctenolepisma sp.); Pulex sp.; Trichodectes sp.; Cimex sp.; aminal-parasitic mites such as *Boophilus microplus* and aemaphysalis longicornis and Epidermoptidae.

Further, the compounds of the present invention are effective also against pests which show resistance to organophosphorus compounds, carbamate compounds, synthetic pyrethroid compounds, acylurea compounds or conventional insecticides.

Thus, compounds of the present invention exhibit excellent pesticidal effects against a wide range of pests including hemipteran insects, lepidoteran insects, coleopteran insects, dipteran insects, hymenopteran insects, orthopteran insects, isopteran insects, thysanopteran insects, mites and plant-parastic nematodes, and they are also capable of controlling pests which acquired resistance to conventional pesticides.

Now, formulation methods will be described in detail with reference to typical Formulation Examples. However, it should be understood that the types and the proportions of the compounds and the adjuvants are not restricted by these specific Examples and may be varied within wide ranges. In the following examples, "%" means "% by weight".

FORMULATION EXAMPLE 1

Emulsifiable Concentrate

30% of compound (I-22), 20% of cyclohaxanone, 11% of polyoxyethylene alkylaryl ether, 4% of calcium alkylbenzene sulfonate and 35% of methylnaphthalene were uniformly dissolved to obtain an emulsifiable concentrate.

FORMULATION EXAMPLE 2

Wettable Powder

10% of compound (I-22), 0.5% of a sodium salt of a naphthalene sulfonic acid/formalin condensation product, 0.5% of polyoxyethylene alkylaryl ether, 24% of diatomaceous earth and 65% of clay were uniformly mixed and pulverized to obtain a wettable powder.

FORMULATION EXAMPLE 3

Dust

2% of compound (I-22), 5% of diatomaceous earth and 93% of clay were uniformly mixed and pulverized to obtain a dust.

FORMULATION EXAMPLE 4

Granule

5% of compound (I-22), 2% of sodium lauryl alcohol sulfate, 5% of sodium lignin sulfonate, 2% of carboxymethylcellulose and 86% of clay were uniformly mixed and pulverized. 100 parts by weight of this mixture was kneaded with 20 parts by weight of water and formed into granules of from 14 to 32 mesh by an extrusion-type granulator, followed by drying to obtain a granule formulation.

Now, the effects of the pesticides containing the compounds of the present invention as active ingredients will be described with reference to Test Examples. Comparative Compounds a and b are compounds disclosed in Example 165 and Example 6 in Japanese Unexamined Patent Publication No. 122261/1979; Comparative Compound c is a compound disclosed in Example 88 in Japanese Unexamined Patent Publication No. 45452/1981; and Comparative Compound d is a compound disclosed in Example 6 in U.S. Pat. No. 3,732,3067. These Comparative Compounds were formulated and used in the same manner as the compounds of the present invention.

Comparative Compound a: 4-chloro4'-isopropylthiobenzophenone-N'-ethoxycarbonylhydrazone Comparative Compound b: 4-chloro-4'-propylsulfonylbenzophenone-N'-propionylhydrazone Comparative Compound c: 4-chloro-4'-methylsulfinylbenzophenone-N'-ethoxycabonylhydrazone Comparative Compound d: 4-trifluoromethylbenzophenonehydrazone

TEST EXAMPLE 1

Insecticidal test for diamondback moth

The wettable powder prepared according to Formulation Example 2 was diluted with water so that the concentration of the active ingredient was 500 ppm. Cabbage leaves were immersed in the resulting diluted solution, dried in air and then placed in a polyvinyl chloride cup. Ten larvae of diamondback moth were released in the cup, and thereafter a cover was placed thereon. Then, the cup was placed in a thermostatic chamber of 25° C. for 6 days, and the number of insects died was counted to calculate the mortality (%) according to a calculation formula (A). The results are shown in Table 36. The test was carried out in two series.

$$\text{Mortality } (\%) = \frac{\text{Number of insects died}}{\text{Number of insects released}} \times 100 \qquad (A)$$

TABLE 36

| Compound No. | Mortality |
| --- | --- |
| I-1 | 100 |
| I-2 | 100 |
| I-10 | 100 |
| I-11 | 100 |
| I-12 | 100 |
| I-13 | 100 |
| I-14 | 100 |
| I-15 | 100 |
| I-16 | 100 |
| I-17 | 100 |
| I-18 | 100 |
| I-19 | 100 |
| I-20 | 100 |
| I-21 | 100 |

TABLE 36-continued

| Compound No. | Mortality |
|---|---|
| I-22 | 100 |
| I-23 | 100 |
| I-24 | 100 |
| I-25 | 100 |
| I-26 | 100 |
| I-31 | 100 |
| I-32 | 100 |
| I-34 | 100 |
| I-35 | 100 |
| I-40 | 100 |
| I-41 | 100 |
| I-42 | 100 |
| I-43 | 100 |
| I-44 | 100 |
| I-45 | 100 |
| I-46 | 100 |
| I-47 | 100 |
| I-48 | 100 |
| I-40 | 100 |
| I-51 | 100 |
| I-52 | 100 |
| I-53 | 100 |
| I-54 | 100 |
| I-55 | 100 |
| I-56 | 100 |
| I-57 | 100 |
| I-58 | 100 |
| I-59 | 100 |
| I-60 | 100 |
| I-61 | 100 |
| I-62 | 100 |
| I-63 | 100 |
| I-64 | 100 |
| I-65 | 100 |
| I-66 | 100 |
| I-67 | 100 |
| I-68 | 100 |
| I-69 | 100 |
| I-70 | 100 |
| I-71 | 100 |
| I-72 | 100 |
| I-73 | 100 |
| I-74 | 100 |
| I-75 | 100 |
| I-76 | 100 |
| I-77 | 100 |
| I-78 | 100 |
| I-81 | 100 |
| I-83 | 100 |
| I-84 | 100 |
| I-88 | 100 |
| I-89 | 100 |
| I-90 | 100 |
| I-91 | 100 |
| I-92 | 100 |
| I-93 | 100 |
| I-94 | 100 |
| I-95 | 100 |
| I-96 | 100 |
| I-97 | 100 |
| I-98 | 100 |
| I-99 | 100 |
| I-100 | 100 |
| I-101 | 100 |
| I-102 | 100 |
| I-106 | 100 |
| I-114 | 100 |
| I-115 | 100 |
| I-116 | 100 |
| I-117 | 100 |
| I-118 | 100 |
| I-119 | 100 |
| I-121 | 100 |
| I-122 | 100 |
| I-124 | 100 |
| I-125 | 100 |
| I-128 | 100 |
| I-129 | 100 |
| I-130 | 100 |
| I-132 | 100 |
| I-133 | 100 |
| I-134 | 100 |
| I-135 | 100 |
| I-136 | 100 |
| I-137 | 100 |
| I-138 | 100 |
| I-140 | 100 |
| I-141 | 100 |
| I-148 | 100 |
| I-149 | 100 |
| I-150 | 100 |
| I-151 | 100 |
| I-153 | 100 |
| I-154 | 100 |
| I-155 | 100 |
| I-156 | 100 |
| I-157 | 100 |
| I-158 | 100 |
| I-159 | 100 |
| I-160 | 100 |
| I-161 | 100 |
| I-162 | 100 |
| I-163 | 100 |
| I-164 | 100 |
| I-165 | 100 |
| I-166 | 100 |
| I-168 | 100 |
| I-169 | 100 |
| I-171 | 100 |
| I-173 | 100 |
| I-174 | 100 |
| I-175 | 100 |
| I-176 | 100 |
| I-177 | 100 |
| I-178 | 100 |
| I-179 | 100 |
| I-181 | 100 |
| I-182 | 100 |
| I-183 | 100 |
| I-184 | 100 |
| I-185 | 100 |
| I-186 | 100 |
| I-187 | 100 |
| I-188 | 100 |
| I-189 | 100 |
| I-190 | 100 |
| I-191 | 100 |
| I-192 | 100 |
| I-193 | 100 |
| I-194 | 100 |
| I-195 | 100 |
| I-196 | 100 |
| I-197 | 100 |
| I-206 | 100 |
| I-207 | 100 |
| I-209 | 100 |
| I-210 | 100 |
| I-211 | 100 |
| I-212 | 100 |
| I-213 | 100 |
| I-214 | 100 |
| I-216 | 100 |
| I-217 | 100 |
| I-218 | 100 |
| I-220 | 100 |
| I-221 | 100 |
| I-222 | 100 |
| I-223 | 100 |
| I-224 | 100 |
| I-225 | 100 |
| I-226 | 100 |
| I-238 | 100 |

TABLE 36-continued

| Compound No. | Mortality |
|---|---|
| I-247 | 100 |
| I-250 | 100 |
| I-251 | 100 |
| I-252 | 100 |
| I-253 | 100 |
| I-254 | 100 |
| I-255 | 100 |
| I-256 | 100 |
| I-257 | 100 |
| I-258 | 100 |
| I-259 | 100 |
| I-260 | 100 |
| I-261 | 100 |
| I-263 | 100 |
| I-264 | 100 |
| I-265 | 100 |
| I-266 | 100 |
| I-268 | 100 |
| I-269 | 100 |
| I-274 | 100 |
| I-277 | 100 |
| I-278 | 100 |
| I-380 | 100 |
| I-281 | 100 |
| I-282 | 100 |
| I-283 | 100 |
| I-284 | 100 |
| I-285 | 100 |
| I-286 | 100 |
| I-290 | 100 |
| I-291 | 100 |
| I-292 | 100 |
| I-293 | 100 |
| I-294 | 100 |
| I-295 | 100 |
| I-296 | 100 |
| I-297 | 100 |
| I-298 | 100 |
| I-299 | 100 |
| I-300 | 100 |
| I-301 | 100 |
| I-302 | 100 |
| I-303 | 100 |
| I-305 | 100 |
| I-306 | 100 |
| I-307 | 100 |
| I-308 | 100 |
| I-309 | 100 |
| I-310 | 100 |
| I-311 | 100 |
| I-312 | 100 |
| I-313 | 100 |
| I-314 | 100 |
| I-315 | 100 |
| I-316 | 100 |
| I-317 | 100 |
| I-318 | 100 |
| I-319 | 100 |
| I-320 | 100 |
| I-321 | 100 |
| I-322 | 100 |
| I-323 | 100 |
| I-324 | 100 |
| I-326 | 100 |
| I-328 | 100 |
| I-329 | 100 |
| I-330 | 100 |
| I-331 | 100 |
| I-332 | 100 |
| I-333 | 100 |
| I-334 | 100 |
| I-335 | 100 |
| I-336 | 100 |
| I-337 | 100 |
| I-338 | 100 |
| I-339 | 100 |
| I-340 | 100 |
| I-341 | 100 |
| I-342 | 100 |
| I-343 | 100 |
| I-344 | 100 |
| I-345 | 100 |
| I-346 | 100 |
| I-347 | 100 |
| I-348 | 100 |
| I-349 | 100 |
| I-350 | 100 |
| I-351 | 100 |
| I-352 | 100 |
| I-353 | 100 |
| I-354 | 100 |
| I-355 | 100 |
| I-356 | 100 |
| I-357 | 100 |
| I-358 | 100 |
| I-359 | 100 |
| I-360 | 100 |
| I-361 | 100 |
| I-362 | 100 |
| I-363 | 100 |
| I-364 | 100 |
| I-365 | 100 |
| I-366 | 100 |
| I-367 | 100 |
| I-368 | 100 |
| I-370 | 100 |
| I-371 | 100 |
| I-372 | 100 |
| I-373 | 100 |
| I-374 | 100 |
| I-376 | 100 |
| I-377 | 100 |
| I-379 | 100 |
| I-380 | 100 |
| I-381 | 100 |
| I-382 | 100 |
| I-383 | 100 |
| I-384 | 100 |
| I-385 | 100 |
| I-386 | 100 |
| I-387 | 100 |
| I-388 | 100 |
| I-389 | 100 |
| I-390 | 100 |
| I-391 | 100 |
| I-392 | 100 |
| I-393 | 100 |
| I-394 | 100 |
| I-395 | 100 |
| I-396 | 100 |
| I-397 | 100 |
| I-398 | 100 |
| I-399 | 100 |
| I-400 | 100 |
| I-401 | 100 |
| I-402 | 100 |
| I-403 | 100 |
| I-404 | 100 |
| I-405 | 100 |
| I-407 | 100 |
| I-408 | 100 |
| I-409 | 100 |
| I-410 | 100 |
| I-411 | 100 |
| I-412 | 100 |
| I-414 | 100 |
| I-415 | 100 |
| I-416 | 100 |
| I-417 | 100 |
| I-418 | 100 |
| I-419 | 100 |
| I-420 | 100 |

TABLE 36-continued

| Compound No. | Mortality |
|---|---|
| I-421 | 100 |
| I-423 | 100 |
| I-424 | 100 |
| I-425 | 100 |
| I-426 | 100 |
| I-428 | 100 |
| I-429 | 100 |
| I-431 | 100 |
| I-432 | 100 |
| I-435 | 100 |
| I-436 | 100 |
| I-437 | 100 |
| I-438 | 100 |
| I-439 | 100 |
| I-440 | 100 |
| I-441 | 100 |
| I-442 | 100 |
| I-443 | 100 |
| I-444 | 100 |
| I-445 | 100 |
| I-447 | 100 |
| I-448 | 100 |
| I-449 | 100 |
| I-450 | 100 |
| I-451 | 100 |
| I-452 | 100 |
| I-453 | 100 |
| I-455 | 100 |
| I-456 | 100 |
| I-457 | 100 |
| I-458 | 100 |
| I-459 | 100 |
| I-460 | 100 |
| I-461 | 100 |
| I-462 | 100 |
| I-463 | 100 |
| I-464 | 100 |
| I-465 | 100 |
| I-466 | 100 |
| I-467 | 100 |
| I-468 | 100 |
| I-469 | 100 |
| I-470 | 100 |
| I-471 | 100 |
| I-472 | 100 |
| I-473 | 100 |
| I-474 | 100 |
| I-475 | 100 |
| I-476 | 100 |
| I-477 | 100 |
| I-478 | 100 |
| I-480 | 100 |
| I-481 | 100 |
| I-482 | 100 |
| I-483 | 100 |
| I-484 | 100 |
| I-485 | 100 |
| I-486 | 100 |
| I-487 | 100 |
| I-488 | 100 |
| I-489 | 100 |
| I-490 | 100 |
| I-491 | 100 |
| I-492 | 100 |
| I-494 | 100 |
| I-495 | 100 |
| I-496 | 100 |
| I-497 | 100 |
| I-498 | 100 |
| I-499 | 100 |
| I-500 | 100 |
| I-501 | 100 |
| I-502 | 100 |
| I-504 | 100 |
| I-509 | 100 |
| I-510 | 100 |
| I-516 | 100 |
| I-517 | 100 |
| I-518 | 100 |
| I-519 | 100 |
| I-520 | 100 |
| I-521 | 100 |
| I-522 | 100 |
| I-523 | 100 |
| I-524 | 100 |
| I-525 | 100 |
| I-526 | 100 |
| I-527 | 100 |
| I-528 | 100 |
| I-529 | 100 |
| I-530 | 100 |
| I-531 | 100 |
| I-532 | 100 |
| I-533 | 100 |
| I-534 | 100 |
| I-535 | 100 |
| I-536 | 100 |
| I-537 | 100 |
| I-538 | 100 |
| I-539 | 100 |
| I-540 | 100 |
| II-5 | 100 |
| II-6 | 100 |
| II-8 | 100 |
| II-10 | 100 |
| II-11 | 100 |
| II-12 | 100 |
| II-13 | 100 |
| II-14 | 100 |
| II-15 | 100 |
| II-16 | 100 |
| II-22 | 100 |
| II-23 | 100 |
| II-24 | 100 |
| II-29 | 100 |
| II-30 | 100 |
| II-32 | 100 |
| II-35 | 100 |
| II-36 | 100 |
| II-37 | 100 |
| II-38 | 100 |
| II-39 | 100 |
| II-40 | 100 |
| II-41 | 100 |
| II-42 | 100 |
| II-43 | 100 |
| II-44 | 100 |
| II-45 | 100 |
| II-46 | 100 |
| II-47 | 100 |
| II-48 | 100 |
| II-49 | 100 |
| II-50 | 100 |
| II-51 | 100 |
| II-52 | 100 |
| III-1 | 100 |
| III-2 | 100 |
| III-3 | 100 |
| III-4 | 100 |
| III-5 | 100 |
| III-6 | 100 |
| III-7 | 100 |
| III-8 | 100 |
| III-9 | 100 |
| III-10 | 100 |
| III-11 | 100 |
| IV-1 | 100 |
| V-1 | 100 |
| V-2 | 100 |
| V-3 | 100 |
| V-4 | 100 |
| V-5 | 100 |

TABLE 36-continued

| Compound No. | Mortality |
| --- | --- |
| V-6 | 100 |
| V-7 | 100 |
| V-8 | 100 |
| V-9 | 100 |
| V-10 | 100 |
| V-11 | 100 |
| V-12 | 100 |
| V-13 | 100 |
| V-14 | 100 |
| V-15 | 100 |
| V-16 | 100 |
| V-17 | 100 |
| V-18 | 100 |
| V-19 | 100 |
| VI-2 | 100 |
| VI-15 | 100 |
| VI-17 | 100 |
| VI-22 | 100 |
| Comparative d | 0 |

TEST EXAMPLE 2

Insecticidal test for brown rice planthopper

The wettable powder prepared according to Formulation Example 2 was diluted with water so that the concentration of the active ingredient was 500 ppm. In the resulting diluted wettable powder were immersed rice stems and leaves, which were then dried in air and placed in a test tube. In the test tube were released 5 larvae of brown rice planthopper, and then the opening of the test tube was plugged with absorbent wadding. Thereafter, the test tube was placed in a thermostatic chamber of 25° C. for 6 days, and then the number of insects died was counted to calculate the mortality (%) according to the calculation formula (A). The test was carried out in two series. The results are shown in Table 37.

TABLE 37

| Compound No. | Mortality |
| --- | --- |
| I-10 | 100 |
| I-11 | 100 |
| I-12 | 100 |
| I-13 | 100 |
| I-14 | 100 |
| I-15 | 100 |
| I-32 | 100 |
| I-41 | 100 |
| I-45 | 100 |
| I-46 | 100 |
| I-47 | 100 |
| I-50 | 100 |
| I-51 | 100 |
| I-52 | 100 |
| I-53 | 100 |
| I-55 | 100 |
| I-61 | 100 |
| I-62 | 100 |
| I-64 | 100 |
| I-65 | 100 |
| I-66 | 100 |
| I-67 | 100 |
| I-68 | 100 |
| I-69 | 100 |
| I-70 | 100 |
| I-71 | 100 |
| I-72 | 100 |

TABLE 37-continued

| Compound No. | Mortality |
| --- | --- |
| I-73 | 100 |
| I-74 | 100 |
| I-75 | 100 |
| I-77 | 100 |
| I-81 | 100 |
| I-83 | 100 |
| I-88 | 100 |
| I-89 | 100 |
| I-90 | 100 |
| I-91 | 100 |
| I-92 | 100 |
| I-93 | 100 |
| I-96 | 100 |
| I-97 | 100 |
| I-98 | 100 |
| I-99 | 100 |
| I-100 | 100 |
| I-101 | 100 |
| I-102 | 100 |
| I-106 | 100 |
| I-114 | 100 |
| I-115 | 100 |
| I-116 | 100 |
| I-117 | 100 |
| I-118 | 100 |
| I-121 | 100 |
| I-122 | 100 |
| I-132 | 100 |
| I-135 | 100 |
| I-136 | 100 |
| I-150 | 100 |
| I-151 | 100 |
| I-157 | 100 |
| I-158 | 100 |
| I-163 | 100 |
| I-164 | 100 |
| I-165 | 100 |
| I-174 | 100 |
| I-176 | 100 |
| I-177 | 100 |
| I-179 | 100 |
| I-180 | 100 |
| I-183 | 100 |
| I-184 | 100 |
| I-185 | 100 |
| I-186 | 100 |
| I-187 | 100 |
| I-188 | 100 |
| I-190 | 100 |
| I-194 | 100 |
| I-211 | 100 |
| I-212 | 100 |
| I-213 | 100 |
| I-214 | 100 |
| I-216 | 100 |
| I-217 | 100 |
| I-218 | 100 |
| I-220 | 100 |
| I-221 | 100 |
| I-222 | 100 |
| I-224 | 100 |
| I-225 | 100 |
| I-249 | 100 |
| I-250 | 100 |
| I-252 | 100 |
| I-253 | 100 |
| I-254 | 100 |
| I-255 | 100 |
| I-256 | 100 |
| I-257 | 100 |
| I-259 | 100 |
| I-260 | 100 |
| I-264 | 100 |
| I-285 | 100 |
| I-290 | 100 |
| I-291 | 100 |

TABLE 37-continued

| Compound No. | Mortality |
|---|---|
| I-293 | 100 |
| I-294 | 100 |
| I-295 | 100 |
| I-296 | 100 |
| I-297 | 100 |
| I-298 | 100 |
| I-299 | 100 |
| I-300 | 100 |
| I-301 | 100 |
| I-302 | 100 |
| I-304 | 100 |
| I-305 | 100 |
| I-306 | 100 |
| I-308 | 100 |
| I-313 | 100 |
| I-314 | 100 |
| I-317 | 100 |
| I-318 | 100 |
| I-319 | 100 |
| I-320 | 100 |
| I-328 | 100 |
| I-329 | 100 |
| I-330 | 100 |
| I-333 | 100 |
| I-334 | 100 |
| I-335 | 100 |
| I-336 | 100 |
| I-337 | 100 |
| I-338 | 100 |
| I-339 | 100 |
| I-340 | 100 |
| I-341 | 100 |
| I-344 | 100 |
| I-346 | 100 |
| I-347 | 100 |
| I-348 | 100 |
| I-349 | 100 |
| I-350 | 100 |
| I-351 | 100 |
| I-352 | 100 |
| I-353 | 100 |
| I-354 | 100 |
| I-355 | 100 |
| I-356 | 100 |
| I-357 | 100 |
| I-358 | 100 |
| I-359 | 100 |
| I-360 | 100 |
| I-361 | 100 |
| I-362 | 100 |
| I-363 | 100 |
| I-364 | 100 |
| I-366 | 100 |
| I-367 | 100 |
| I-368 | 100 |
| I-388 | 100 |
| I-390 | 100 |
| I-392 | 100 |
| I-394 | 100 |
| I-395 | 100 |
| I-399 | 100 |
| I-402 | 100 |
| I-403 | 100 |
| I-414 | 100 |
| I-415 | 100 |
| I-416 | 100 |
| I-418 | 100 |
| I-436 | 100 |
| I-437 | 100 |
| I-438 | 100 |
| I-439 | 100 |
| I-440 | 100 |
| I-444 | 100 |
| I-445 | 100 |
| I-446 | 100 |
| I-447 | 100 |
| I-450 | 100 |
| I-451 | 100 |
| I-452 | 100 |
| I-453 | 100 |
| I-454 | 100 |
| I-466 | 100 |
| I-467 | 100 |
| I-468 | 100 |
| I-470 | 100 |
| I-472 | 100 |
| I-473 | 100 |
| I-474 | 100 |
| I-475 | 100 |
| I-480 | 100 |
| I-481 | 100 |
| I-482 | 100 |
| I-483 | 100 |
| I-484 | 100 |
| I-485 | 100 |
| I-486 | 100 |
| I-487 | 100 |
| I-488 | 100 |
| I-489 | 100 |
| I-490 | 100 |
| I-491 | 100 |
| I-494 | 100 |
| I-496 | 100 |
| I-497 | 100 |
| I-502 | 100 |
| I-510 | 100 |
| I-516 | 100 |
| I-517 | 100 |
| I-520 | 100 |
| I-521 | 100 |
| I-522 | 100 |
| I-524 | 100 |
| I-525 | 100 |
| I-526 | 100 |
| I-527 | 100 |
| I-528 | 100 |
| I-529 | 100 |
| I-530 | 100 |
| I-531 | 100 |
| I-532 | 100 |
| I-533 | 100 |
| I-534 | 100 |
| I-535 | 100 |
| I-536 | 100 |
| I-537 | 100 |
| I-538 | 100 |
| I-539 | 100 |
| I-540 | 100 |
| II-10 | 100 |
| II-12 | 100 |
| II-13 | 100 |
| II-14 | 100 |
| II-23 | 100 |
| II-29 | 100 |
| II-30 | 100 |
| II-36 | 100 |
| II-37 | 100 |
| II-51 | 100 |
| II-52 | 100 |
| III-2 | 100 |
| III-4 | 100 |
| III-6 | 100 |
| III-7 | 100 |
| III-8 | 100 |
| III-9 | 100 |
| III-10 | 100 |
| III-11 | 100 |
| IV-1 | 100 |
| V-1 | 100 |
| V-3 | 100 |
| V-4 | 100 |
| V-5 | 100 |

TABLE 37-continued

| Compound No. | Mortality |
|---|---|
| V-6 | 100 |
| V-7 | 100 |
| V-9 | 100 |
| V-19 | 100 |
| VI-22 | 100 |
| VI-43 | 100 |
| VI-80 | 100 |
| Comparative a | 10 |
| Comparative b | 20 |
| Comparative c | 20 |

TEST EXAMPLE 3

Insecticidal test for adzuki bean weevil

The wettable powder prepared according to Formulation Example 2 was diluted with water to a concentration of 100 ppm. 0.75 ml of this diluted solution was dropped on a filter paper having diameter of 6 cm placed in a polyvinyl chloride cup having a capacity of 60 ml. Five female adults of adzuki bean weevil were released in the cup, and a cover was placed thereon. Then, the cup was placed in a thermostatic chamber of 25° C. for 4 days, and the number of insects died was counted to calculate the mortality (%) according to calculation formula (A). The test was carried out in two series. The results are shown in Table 38.

TABLE 38

| Compound No. | Mortality |
|---|---|
| I-11 | 100 |
| I-44 | 100 |
| I-67 | 100 |
| I-69 | 100 |
| I-88 | 100 |
| I-89 | 100 |
| I-90 | 100 |
| I-94 | 100 |
| I-96 | 100 |
| I-97 | 100 |
| I-99 | 100 |
| I-102 | 100 |
| I-106 | 100 |
| I-114 | 100 |
| I-115 | 100 |
| I-116 | 100 |
| I-118 | 100 |
| I-140 | 100 |
| I-141 | 100 |
| I-149 | 100 |
| I-150 | 100 |
| I-151 | 100 |
| I-153 | 100 |
| I-155 | 100 |
| I-156 | 100 |
| I-157 | 100 |
| I-160 | 100 |
| I-161 | 100 |
| I-162 | 100 |
| I-165 | 100 |
| I-173 | 100 |
| I-174 | 100 |
| I-175 | 100 |
| I-176 | 100 |
| I-177 | 100 |
| I-178 | 100 |
| I-179 | 100 |
| I-180 | 100 |
| I-183 | 100 |

TABLE 38-continued

| Compound No. | Mortality |
|---|---|
| I-185 | 100 |
| I-186 | 100 |
| I-187 | 100 |
| I-188 | 100 |
| I-189 | 100 |
| I-191 | 100 |
| I-192 | 100 |
| I-194 | 100 |
| I-195 | 100 |
| I-196 | 100 |
| I-197 | 100 |
| I-206 | 100 |
| I-218 | 100 |
| I-222 | 100 |
| I-253 | 100 |
| I-254 | 100 |
| I-257 | 100 |
| I-258 | 100 |
| I-263 | 100 |
| II-5 | 100 |
| II-6 | 100 |
| II-10 | 100 |
| II-11 | 100 |
| II-12 | 100 |
| II-13 | 100 |
| II-15 | 100 |
| II-16 | 100 |
| Comparative b | 0 |
| Comparative d | 0 |

We claim:

1. A benzylsulfide derivative of the formula (I) or its salt:

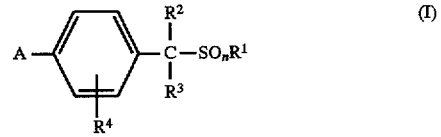

(I)

wherein $R^1$ is a $C_{1-6}$ alkyl group, a $C_{1-4}$ cyanoalkyl group, a $C_{1-4}$ hydroxyalkyl group, a $C_{3-6}$ cycloalkyl group, a $C_{1-6}$ haloalkyl group, a $C_{2-4}$ alkenyl group, a $C_{2-4}$ alkynyl group, a phenyl group (which may be substituted by a halogen atom or a $C_{1-4}$ alkyl group), a cyano group, a benzyl group (which may be substituted by a halogen atom), a thiazolyl group, a $C_{1-4}$ alkylcarbamoyl group or a group of the formula —$N(R^5)R^6$; each of $R^2$ and $R^3$ which are independent of each other, is a hydrogen atom, a halogen atom, a cyano group, a $C_{1-4}$ alkyl group, a $C_{1-3}$ haloalkyl group, a $C_{1-4}$ alkylthio group, a $C_{1-4}$ alkylcarbonyl group, a carboxyl group, or a $C_{1-4}$ alkoxycarbonyl group; or $R^2$ and $R^3$ may form a 3- to 6-membered ring together with the carbon atom to which they are bonded; or $R^1$ and $R^2$ may form a 3- to 8-membered ring having one or more hetero atoms, together with the sulfur and carbon atoms to which they are respectively bonded; $R^4$ is a hydrogen atom, a halogen atom, a $C_{1-4}$ alkyl group, a $C_{1-4}$ haloalkyl group, a $C_{1-4}$ alkoxy group or a $C_{1-4}$ haloalkoxy group; each of $R^5$ and $R^6$ which are independent of each other, is a hydrogen atom, a $C_{1-6}$ alkyl group or a $C_{1-4}$ haloalkyl group; or $R^5$ and $R^6$ may together form a group of the formula =$CR^7R^8$; or $R^5$ and $R^6$ may form a 4- to 8-membered ring having one or more hetero atoms, together with the nitrogen atom to which they are bonded; $R^7$ is a hydrogen atom, a $C_{1-3}$ alkyl group or a $C_{1-3}$ alkylthio group; $R^8$ is a $C_{1-3}$ alkylthio group or a $C_{1-3}$ alkylamino group; or $R^7$ and $R^8$ may form a saturated or unsaturated 4- to 8-membered ring together with the carbon atom to which they are bonded; A is a hydrazinoaralkyl or hydrazonoaralkyl group of the formula (A1) or (A2);

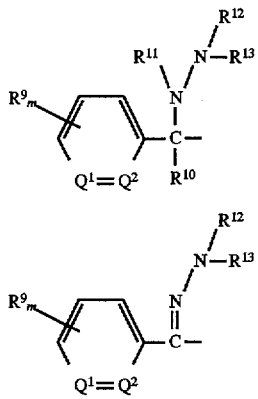

R⁹ is a hydrogen atom, a halogen atom, a nitro group, a cyano group, a $C_{1-4}$ alkyl group, a $C_{1-4}$ haloalkyl group, a $C_{1-4}$ alkoxy group, a $C_{1-4}$ haloalkoxy group, a $C_{1-4}$ alkylthio group, a $C_{1-4}$ haloalkylthio group, a $C_{1-4}$ alkylsulfonyl group, a $C_{2-4}$ alkylsulfonylmethyl group, a $C_{1-4}$ haloalkylsulfonyloxy group, a phenyl group (which may be substituted by a halogen atom) or a phenoxy group (which may be substituted by a halogen atom); or two R⁹ may together form a 5- or 6-membered ring; $R^{10}$ is a hydrogen atom or a $C_{1-4}$ alkyl group; each of $R^{11}$, $R^{12}$ and $R^{13}$ which are independent of one another, is a hydrogen atom, a cyano group, a $C_{1-6}$ alkyl group, a $C_{1-4}$ haloalkyl group, a $C_{2-10}$ alkoxyalkyl group, a $C_{3-8}$ alkoxyalkoxyalkyl group, a $C_{2-6}$ alkylthioalkyl group, a $C_{2-6}$ alkenyl group, a $C_{2-4}$ alkynyl group, a $C_{1-4}$ cyanoalkyl group, a benzyl group (which may be substituted by a halogen atom, a $C_{1-4}$ haloalkyl group or a $C_{1-4}$ alkyl group), a group of the formula —COR¹⁴, a group of the formula —CSR¹⁴, a group of the formula —COOR¹⁵, a group of the formula —COSR¹⁵, a group of the formula —CON(R¹⁶)R¹⁷, a group of the formula —CSN(R¹⁶)R¹⁷, a group of the formula —SN(R¹⁸)R¹⁹, a group of the formula —SO₂R²⁰ or a group of the formula —C(R²¹)=CHR²²; or $R^{12}$ and $R^{13}$ may together form a group of the formula =CR²³R²⁴; or $R^{12}$ and $R^{13}$ may form a 4- to 8-membered ring having one or more hetero atoms, together with the nitrogen atom to which they are bonded; $R^{14}$ is a hydrogen atom, a $C_{1-20}$ alkyl group, a $C_{1-8}$ haloalkyl group, a $C_{2-12}$ alkoxyalkyl group, a $C_{2-10}$ haloalkoxyalkyl group, a $C_{3-16}$ alkoxyalkoxyalkyl group, a $C_{4-22}$ alkoxyalkoxyalkoxyalkyl group, a $C_{2-6}$ alkylthioalkyl group, a $C_{3-6}$ cycloalkyl group, a $C_{1-6}$ hydroxyalkyl group, a $C_{1-6}$ aminoalkyl group, a $C_{1-6}$ amidoalkyl group, a $C_{1-8}$ cyanoalkyl group, a $C_{3-12}$ alkoxycarbonylalkyl group, a $C_{2-6}$ alkenyl group, a $C_{2-4}$ alkynyl group, a phenyl group (which may be substituted by a halogen atom, a nitro group, a $C_{1-4}$ alkyl group, a $C_{1-4}$ haloalkyl group, a phenoxy group or a $C_{1-4}$ alkoxy group), a naphthyl group (which may be substituted by a halogen atom or a $C_{1-4}$ alkyl group) or a hetero aromatic ring group (which may be substituted by a halogen atom or a $C_{1-4}$ alkyl group); $R^{15}$ is a $C_{1-20}$ alkyl group, a $C_{2-8}$ haloalkyl group, a $C_{2-12}$ alkoxyalkyl group, a $C_{2-6}$ alkenyl group, a $C_{2-4}$ alkynyl group, a benzyl group (which may be substituted by a halogen atom, a $C_{1-4}$ alkoxy group or a $C_{1-4}$ alkyl group) or a phenyl group (which may be substituted by a halogen atom); $R^{16}$ is a hydrogen atom or a $C_{1-4}$ alkyl group; $R^{17}$ is a hydrogen atom, a $C_{1-6}$ alkyl group or a phenyl group (which may be substituted by a halogen atom, a $C_{1-4}$ haloalkoxy group or a $C_{1-4}$ alkyl group); each of $R^{18}$ and $R^{19}$ which are independent of each other, is a $C_{1-4}$ alkyl group (which may be substituted by a $C_{1-4}$ alkoxycarbonyl group), or a $C_{2-5}$ alkoxyalkyl group; or $R^{18}$ and $R^{19}$ may form a 5- or 6-membered ring together with the nitrogen atom to which they are bonded; $R^{20}$ is a $C_{1-4}$ alkyl group, a $C_{1-4}$ haloalkyl group or a $C_{2-4}$ dialkylamino group; $R^{21}$ is a hydrogen atom or a $C_{1-6}$ alkyl group; $R^{22}$ is a $C_{2-4}$ acyl group or a $C_{2-6}$ alkoxycarbonyl group; each of $R^{23}$ and $R^{24}$ which are independent of each other, is a hydrogen atom, a halogen atom, a $C_{1-6}$ alkyl group or a group of the formula —N(R²⁵)R²⁶; each of $R^{25}$ and $R^{26}$ which are independent of each other, is a hydrogen atom, a $C_{1-4}$ alkyl group, a $C_{1-4}$ alkoxy group, a $C_{2-12}$ alkoxyalkyl group or a group of the formula —SO₂R²⁷; or $R^{25}$ and $R^{26}$ may form a 5- or 6-membered ring together with the nitrogen atom to which they are bonded; $R^{27}$ is a $C_{1-8}$ alkyl group or a phenyl group (which may be substituted by a halogen atom or a $C_{1-4}$ alkyl group); each of $Q^1$ and $Q^2$ is a nitrogen atom or a group of the formula —CR⁹; m is an integer of from 1 to 3; and n is 0, 1 or 2.

2. A benzylsulfide derivative of the formula (II):

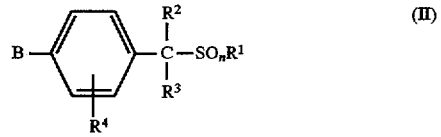

wherein $R^1$ is a $C_{1-4}$ alkyl group, a $C_{1-4}$ cyanoalkyl group, a $C_{1-4}$ hydroxyalkyl group, a $C_{3-6}$ cycloalkyl group, a $C_{1-6}$ haloalkyl group, a $C_{2-4}$ alkynyl group, a phenyl group (which may be substituted by a halogen atom or a $C_{1-4}$ alkyl group), a cyano group, a benzyl group (which may be substituted by a halogen atom), a thiazolyl group, a $C_{1-4}$ alkylcarbamoyl group or a group of the formula —N(R⁵)R⁶; each of $R^2$ and $R^3$ which are independent of each other, is a hydrogen atom, a halogen atom, a cyano group, a $C_{1-4}$ alkyl group, a $C_{1-3}$ haloalkyl group, a $C_{1-4}$ alkylthio group, a $C_{1-4}$ alkylcarbonyl group, a carboxyl group, or a $C_{1-4}$ alkoxycarbonyl group; or $R^2$ and $R^3$ may form a 3- to 6-membered ring together with the carbon atom to which they are bonded; or $R^1$ and $R^2$ may form a 3- to 8-membered ring having one or more hetero atoms, together with the sulfur and carbon atoms to which they are respectively bonded; $R^4$ is a hydrogen atom, a halogen atom, a $C_{1-4}$ haloalkyl group, a $C_{1-4}$ alkoxy group or a $C_{1-4}$ haloalkoxy group; and n is 0, 1 or 2; and B is an aralkyl or arylcarbonyl group of the formula (B1) or (B2):

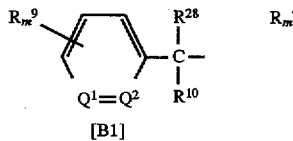 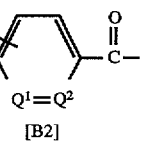

wherein R⁹ is a hydrogen atom, a halogen atom, a nitro group, a cyano group, a $C_{1-4}$ alkyl group, a $C_{1-4}$ haloalkyl group, a $C_{1-4}$ alkoxy group, a $C_{1-4}$ haloalkoxy group, a $C_{1-4}$ alkylthio group, a $C_{1-4}$ haloalkylthio group, a $C_{1-4}$ alkylsulfonyl group, a $C_{2-4}$ alkylsulfonylmethyl group, a $C_{1-4}$ haloalkylsulfonyloxy group, a phenyl group (which may be substituted by a halogen atom) or a phenoxy group (which may be substituted by a halogen atom); or two R⁹ may be together form a 5- or 6-membered ring; $R^{10}$ is a hydrogen atom or a $C_{1-4}$ alkyl group; each of $Q^1$ and $Q^2$ is a nitrogen atom or a group of the formula —CR⁹; m is an integer of from 1 to 3, and $R^{28}$ is a halogen atom or a hydroxyl group, and excluding the compound wherein B has the formula (B2), $Q^1$ and $Q^2$ are CH, m=1, $R^4$ and $R^9$ are hydrogen, $R^1$, $R^2$ and $R^3$ are methyl, and n=0.

3. A benzophenonehydrazone derivative of the formula (III):

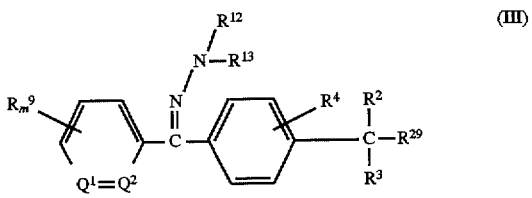

wherein $R^4$ is a hydrogen atom, a halogen atom, a $C_{1-4}$ alkyl group, a $C_{1-4}$ haloalkyl group, a $C_{1-4}$ alkoxy group or a $C_{1-4}$ haloalkoxy group; $R^9$ is a hydrogen atom, a halogen atom, a nitro group, a cyano group, a $C_{1-4}$ alkyl group, a $C_{1-4}$ haloalkyl group, a $C_{1-4}$ alkoxy group, a $C_{1-4}$ haloalkoxy group, a $C_{1-4}$ alkylthio group, a $C_{1-4}$ haloalkylthio group, a $C_{1-4}$ alkylsulfonyl group, a $C_{2-4}$ alkylsulfonylmethyl group, a $C_{1-4}$ haloalkylsulfonyloxy group, a phenyl group (which may be substituted by a halogen atom) or a phenoxy group (which may be substituted by a halogen atom); or two $R^9$ may together form a 5- or 6-membered ring; each of $R^{12}$ and $R^{13}$ which are independent of one another, is a hydrogen atom, a cyano group, a $C_{1-6}$ alkyl group, a $C_{1-4}$ haloalkyl group, a $C_{2-10}$ alkoxyalkyl group, a $C_{3-8}$ alkoxyalkoxyalkyl group, a $C_{2-6}$ alkylthioalkyl group, a $C_{2-6}$ alkenyl group, a $C_{2-4}$ alkynyl group, a $C_{1-4}$ cyanoalkyl group, a benzyl group (which may be substituted by a halogen atom, a $C_{1-4}$ haloalkyl group or a $C_{1-4}$ alkyl group), a group of the formula —$COR^{14}$, a group of the formula —$CSR^{14}$, a group of the formula —$COOR^{15}$, a group of the formula —$COSR^{15}$, a group of the formula —$CON(R^{16})R^{17}$, a group of the formula —$CSN(R^{16})R^{17}$, a group of the formula —$SN(R^{18})R^{19}$, a group of the formula —$SO_2R^{20}$ or a group of the formula —$C(R^{21})$=$CHR^{22}$; or $R^{12}$ and $R^{13}$ may together form a group of the formula =$CR^{23}R^{24}$; or $R^{12}$ and $R^{13}$ may form a 4- to 8-membered ring having one or more hetero atoms, together with the nitrogen atom to which they are bonded; $R^{14}$ is a hydrogen atom, a $C_{1-20}$ alkyl group, a $C_{1-8}$ haloalkyl group, a $C_{2-12}$ alkoxyalkyl group, a $C_{2-10}$ haloalkoxyalkyl group, a $C_{3-16}$ alkoxyalkoxyalkyl group, a $C_{4-22}$ alkoxyalkoxyalkoxyalkyl group, a $C_{2-6}$ alkylthioalkyl group, a $C_{3-6}$ cycloalkyl group, a $C_{1-6}$ hydroxyalkyl group, a $C_{1-6}$ aminoalkyl group, a $C_{1-6}$ amidoalkyl group, a $C_{1-8}$ cyanalkyl group, a $C_{3-12}$ alkoxycarbonylalkyl group, a $C_{2-6}$ alkenyl group, a $C_{2-4}$ alkynyl group, a phenyl group (which may be substituted by a halogen atom, a nitro group, a $C_{1-4}$ alkyl group, a $C_{1-4}$ haloalkyl group, a phenoxy group or a $C_{1-4}$ alkoxy group), a naphthyl group (which may be substituted by a halogen atom or a $C_{1-4}$ alkyl group) or a hetero aromatic ring group (which may be substituted by a halogen atom or a $C_{1-4}$ alkyl group); $R^{15}$ is a $C_{1-20}$ alkyl group, a $C_{2-8}$ haloalkyl group, a $C_{2-12}$ alkoxyalkyl group, a $C_{2-6}$ alkenyl group, a $C_{2-4}$ alkynyl group, a benzyl group (which may be substituted by a halogen atom, a $C_{1-4}$ alkoxy group or a $C_{1-4}$ alkyl group) or a phenyl group (which may be substituted by a halogen atom); $R^{16}$ is a hydrogen atom or a $C_{1-4}$ alkyl group; $R^{17}$ is a hydrogen atom, a $C_{1-6}$ alkyl group or a phenyl group (which may be substituted by a halogen atom, a $C_{1-4}$ haloalkoxy group or a $C_{1-4}$ alkyl group); each of $R^{18}$ and $R^{19}$ which are independent of each other, is a $C_{1-4}$ alkyl group (which may be substituted by a $C_{1-4}$ alkoxycarbonyl group), or $C_{2-5}$ alkoxyalkyl group; or $R^{18}$ and $R^{19}$ may form a 5- or 6-membered ring together with the nitrogen atom to which they are bonded; $R^{20}$ is a $C_{1-4}$ alkyl group, a $C_{1-4}$ haloalkyl group or a $C_{2-4}$ dialkylamino group; $R^{21}$ is a hydrogen atom or a $C_{1-6}$ alkyl group; $R^{22}$ is a $C_{2-4}$ acyl group or a $C_{2-6}$ alkoxycarbonyl group; each of $R^{23}$ and $R^{24}$ which are independent of each other, is a hydrogen atom, a halogen atom, a $C_{1-6}$ alkyl group or a group of the formula —$N(R^{25})R^{26}$; each of $R^{25}$ and $R^{26}$ which are independent of each other, is a hydrogen atom, a $C_{1-4}$ alkyl group, a $C_{1-4}$ alkoxy group, $C_{2-12}$ alkoxyalkyl group or a group of the formula —$SO_2R^{27}$; or $R^{25}$ and $R^{26}$ may form a 5- or 6-membered ring together with the nitrogen atom to which they are bonded; $R^{27}$ is a $C_{1-8}$ alkyl group or a phenyl group (which may be substituted by a halogen atom or a $C_{1-4}$ alkyl group); each of $Q^1$ and $Q^2$ is a nitrogen atom or a group of the formula —$CR^9$; m is an integer of from 1 to 3; each of $R^2$ and $R^3$ which are independent of each other, is a hydrogen atom or a $C_{1-4}$ alkyl group, and $R^{29}$ is a halogen atom, a mercapto group or a hydroxyl group.

4. A process for producing the benzylsulfide derivative of claim 1, wherein A is a group of the formula (A2), which comprises reacting a compound of the formula (IV):

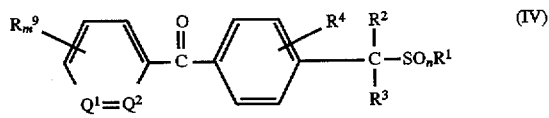

wherein $R^1$, $R^2$, $R^3$, $R^4$, $R^9$, m, n, $Q^1$ and $Q^2$ are as defined in claim 1, with a compound of the formula (VI):

wherein $R^{12}$ and $R^{13}$ are as defined in claim 1.

5. A process for producing the benzylsulfide derivative of claim 1, wherein A is a group of the formula (A2), which comprises reacting a compound of the formula (III);

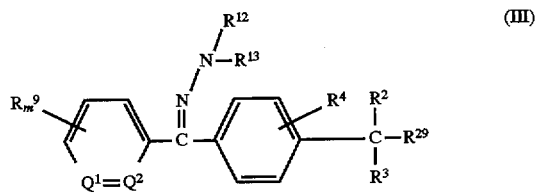

wherein $R^2$, $R^3$, $R^4$, $R^9$, $R^{12}$, $R^{13}$, m, $Q^1$ and $Q^2$ are as defined in claim 1, and $R^{29}$ is a halogen atom, a mercapto group or a hydroxyl group with a compound of the formula (V2):

wherein Z is a halogen atom, a $C_{1-4}$ alkylsulfonyl group or a benzenesulfonyloxy group (which may be substituted by a methyl group) when $R^{29}$ is a mercapto group, or a group of the formula a —$S(O)_nM$ when $R^{29}$ is a halogen atom, or a group of the formula —$SSR^1$ when $R^{29}$ is a hydroxyl group; $R^1$ is a $C_{1-6}$ alkyl group, a $C_{1-4}$ cyanoalkyl group, a $C_{3-6}$ cycloalkyl group, a $C_{1-6}$ haloalkyl group, a $C_{2-4}$ alkenyl group or a benzyl group (which may be substituted by a halogen atom); M is an alkali metal; and n is 0 or 2.

6. A process for producing the benzylsulfide derivative of claim 1, wherein A is a group of the formula (A1), which comprises reacting a compound of the formula (VI):

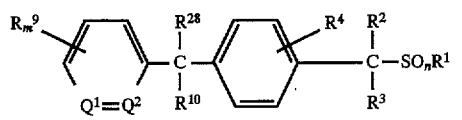 (VI)
wherein $R^1$, $R^2$, $R^3$, $R^4$, $R^9$, $R^{10}$, m, n, $Q^1$ and $Q^2$ are as defined in claim 1, and $R^{28}$ is a halogen atom, with a compound of the formula (VI):
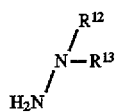 (VI)
wherein $R^{12}$ and $R^{13}$ are as defined in claim 1.
7. A pesticide comprising a pesticidally effective amount of the benzylsulfide derivative as defined in claim 1 and an agriculturally acceptable carrier.
* * * * *